US007151164B2

(12) United States Patent
Hansen et al.

(10) Patent No.: US 7,151,164 B2
(45) Date of Patent: Dec. 19, 2006

(54) ANTI-CD20 ANTIBODIES AND FUSION PROTEINS THEREOF AND METHODS OF USE

(75) Inventors: Hans Hansen, Picayune, MS (US); Zhengxing Qu, Warren, NJ (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 356 days.

(21) Appl. No.: 10/366,709

(22) Filed: Feb. 14, 2003

(65) Prior Publication Data

US 2003/0219433 A1 Nov. 27, 2003

Related U.S. Application Data

(60) Provisional application No. 60/356,132, filed on Feb. 14, 2002, provisional application No. 60/416,232, filed on Oct. 7, 2002.

(51) Int. Cl.
*C12P 21/08* (2006.01)
*C07H 21/04* (2006.01)
*A61K 39/395* (2006.01)
*C12N 15/00* (2006.01)
*C07K 16/00* (2006.01)
*C07H 21/02* (2006.01)
*G01N 33/574* (2006.01)
*A61K 49/00* (2006.01)

(52) U.S. Cl. .............. 530/387.3; 530/388.1; 530/388.22; 530/388.73; 530/388.8; 536/23.53; 424/133.1; 424/141.1; 424/143.1; 424/155.1; 435/69.6; 435/320.1

(58) Field of Classification Search ............ 530/387.1, 530/387.3, 388.1, 388.22, 388.8, 391.5, 391.7, 530/388.73; 424/130.1, 133.1, 141.1, 143.1, 424/155.1, 179.1; 536/23.53; 435/69.6, 435/320.1
See application file for complete search history.

(56) References Cited

U.S. PATENT DOCUMENTS

| 4,036,945 | A | | 7/1977 | Haber |
|---|---|---|---|---|
| 4,046,722 | A | | 9/1977 | Rowland |
| 4,331,647 | A | | 5/1982 | Goldenberg |
| 4,699,784 | A | | 10/1987 | Shih |
| 4,704,692 | A | | 11/1987 | Ladner |
| 4,824,659 | A | | 4/1989 | Hawthorne |
| 4,946,778 | A | | 8/1990 | Ladner |
| 5,057,313 | A | | 10/1991 | Shih |
| 5,229,275 | A | | 7/1993 | Goroff |
| 5,443,953 | A | | 8/1995 | Hansen |
| 5,530,101 | A | * | 6/1996 | Queen et al. |
| 5,567,610 | A | | 10/1996 | Borrebaeck |
| 5,633,425 | A | | 5/1997 | Lonberg |
| 5,734,033 | A | | 3/1998 | Reed |
| 5,736,137 | A | * | 4/1998 | Anderson et al. |
| 5,776,456 | A | | 7/1998 | Anderson et al. |
| 5,798,554 | A | | 8/1998 | Grimaldi |
| 5,827,690 | A | | 10/1998 | Meade |
| 6,077,499 | A | | 6/2000 | Griffiths |
| 6,183,744 | B1 | | 2/2001 | Goldenberg |
| 6,187,287 | B1 | | 2/2001 | Leung |
| 6,254,868 | B1 | | 7/2001 | Leung |
| 6,331,175 | B1 | | 12/2001 | Goldenberg |
| 2002/0004587 | A1 | * | 1/2002 | Miller et al. |
| 2002/0009427 | A1 | | 1/2002 | Wolin et al. |
| 2002/0009444 | A1 | | 1/2002 | Grillo-Lopez |

FOREIGN PATENT DOCUMENTS

| WO | WO 88/04936 A1 | | 7/1988 |
|---|---|---|---|
| WO | WO 92/07466 A1 | | 5/1992 |
| WO | WO 9411026 A2 | * | 5/1994 |
| WO | WO 00/29584 A1 | | 5/2000 |
| WO | WO 00/63403 A2 | | 10/2000 |

OTHER PUBLICATIONS

Longo D. L. Current Opinion in Immunology, 8:353-359, 1994.*
William E. Paul. Fundamental Immunology, 3rd Edition, pp. 292-295, 1993.*
Rudikoff et al. Proc. Natl. Acad. Sci. USA, 79:1979-1983, 1982.*
Kazkaz et al. Current Opinion in Pharmacology, 4:398-402, 2004.*
Gorman et al. Arthritis Research therapy, 5(Suppl 4):S17-S21, 2003.*
Eisenberg et al. Clinical Immunology, 117:207-213, 2005.*
Maloney et al., "New Treatments for Non-Hodgkin's Lymphoma: Monoclonal Antibodies," *Onocology* (Oct. 1998), Supplement No. 8, pp. 63-76, XP 002935647, ISSN: 0030-2414.
Gopal et al., "Clinical applications of anti-CD20 antibodies," *Journal of Laboratory and Clinical Medicine* (1999), vol. 134, No. 5, pp. 445-450, XP 002935646, ISSN: 022-2143.
"An Extended Primer Set for PCR Amplification of Murine Kappa Variable Regions," *Bio Techniques*, Aug. 1993, vol. 15, No. 2.

(Continued)

*Primary Examiner*—Sheela J Huff
*Assistant Examiner*—David J. Blanchard
(74) *Attorney, Agent, or Firm*—Rossi, Kimms & McDowell LLP

(57) ABSTRACT

The present invention provides humanized, chimeric and human anti-CD20 antibodies and CD 20 antibody fusion proteins that bind to a human B cell marker, referred to as CD20, which is useful for the treatment and diagnosis of B-cell disorders, such as B-cell malignancies and autoimmune diseases, and methods of treatment and diagnosis.

16 Claims, 19 Drawing Sheets

OTHER PUBLICATIONS

Ansel, et al., Pharmaceutical Dosage Forms and Drug Delivery Systems, Fifth Edition.

Appelbaum, "Radiolabeled Monoclonal Antibodies in the Treatment of Non-Hodgkin's Lymphoma," *Hematology/Oncology Clinics of North America*, Oct. 1991, pp. 1013-1025, vol. 5, No. 5, W.B. Saunders Company, Harcourt Brace Jovanovich, Inc., Philadelphia London Toronto Montreal Sydney Tokyo.

Frederick M. Ausubel, et al. (EDS.), "Current Protocols In Molecular Biology," 1994, vol. 1, John Wiley & Sons, Inc. & Current Protocols, Published simultaneously in Canada.

Baines, et al., "Purification of Immunoglobulin G (IgG)," *Methods in Molecular Biology*, 1992, pp. 79-105, vol. 10, chapter 8, Immunochemical Protocols, The Humana Press, Inc., Totowa, New Jersey.

Barnes, et al., "Advances in animal cell recombinant protein production: GS-NS0 expression system," *Cytotechnology*, 2000, 109-123, 32, 2000 Kluwer Academic Publishers, Netherlands.

Bird, et al., "Single chain antiboby variable regions," *Tibtech*, Apr. 1991, pp. 132-137, vol. 9, Elsevier Science Publishers Ltd., United Kingdom.

Caron, et al., " Brief Definitive Report Engineered Humanized Dimeric Forms of IgG Are More Effective Antibodies," *J. Exp. Med.*, Oct. 1992, pp. 1191-1195, vol. 176, The Rockefeller University Press.

Carter, et al., "Humanization of an anti-p185$^{HER2}$ antibody for human cancer therapy," *Proc. Natl. Acad. Sci. USA*, Immunology, May 1992, pp. 4285-4289, vol. 89.

Cochlovius, et al., "Advances in Brief Cure of Burkitt's Lymphoma in Severe Combined Immunodeficiency Mice by T Cells, Tetravalent CD3×CD19 Tandem Diabody, and CD28 Costimulation[1]," *Cancer Research*, Aug. 15, 2000, pp. 4336-4341, vol. 60, Germany.

Colman, "Production of therapeutic protiens in the milk of transgenic livestock," *Biochem. Soc. Symp.*, pp. 141-147, 63, Portland Press, United Kingdom.

Coloma, et al., "Design and production of novel tetravalent bispecific antibodies," *Nature Biotechnology*, Feb. 1997, pp. 159-163, vol. 15.

Courtenay-Luck, "Genetic manipulation of monoclonal antibodies," *Genetic manipulation of monoclonal antibodies*, 1995, pp. 166-179, First published University Press, Cambridge, United Kingdom, Press Syndicate of the University of Cambridge, New York.

Devesa, et al., "Cancer Incidence and Mortality Trends Among Whites in the United States, 1947-48," *JNCI*, Oct. 1987, pp. 701-770, vol. 79, No. 4, National Cancer Institute, U.S. Department of Health and Human Services, Public Health Service, National Institutes of Health.

Eary, et al., "Imaging and Treatment of B-Cell Lymphoma," *The Journal of Nuclear Medicine*, Aug. 1990, pp. 1257-1268, vol. 31, No. 8, The Official Publication of The Society of Nuclear Medicine, Inc.

Fitzgerald, et al., "Improved tumour targeting by disulphide stabilized diabodies expressed in *Pichia pastoris*," *Protein Engineering*, 1997, pp. 1221-1225, vol. 10, No. 10, Oxford University Press, United Kingdom.

Foon, et al., "Chronic Lymphocytic Leukemia: New Insights into Biology and Therapy," *Annals of Internal Medicine*, Oct. 1, 1990, pp. 525-539, vol. 113, No. 7, Published twice monthly by the American College of Physicians.

Freedman, "Immunobiology of Chronic Lymphocytic Leukemia," *Hematology/Oncology Clinics* of North America, Apr. 1990, vol. 4, No. 2, W.B. Saunders Company, Harcourt Brace Jovanovich, Inc., Philadelphia London Toronto Montreal Sydney Tokyo.

Freedman, et al., "XXXVI-10 Non-Hodgkin's Lymphomas," *Cancer Medicine—Third Edition*, 1993, pp. 2028-2068, vol. 2, Lea & Febiger, Philadelphia, London.

Gennaro, "Remington: Practice of," 19th Edition, *The Science and Pharmacy*, 1995, Mack Publishing Company, United States.

Ghetie, et al., "Homodimerization of tumor-reactive monoclonal antibodies markedly increases their ability to induce growth arrest or apoptosis of tumor cells," Immunology, *Proc. Natl. Acad. Sci. USA*, Jul. 1997, pp. 7509-7514, vol. 94, The National Academy of Sciences, USA.

Ghetie, et al., "Homodimers but not monomers of Rituxan (chimeric anti-CD20) induce apoptosis in human B-lymphoma cells and synergize with a chemotherapeutic agent and an immunotoxin," *Blood*, Mar. 1, 2001, pp. 1392-1398, vol. 97, No. 5, The American Society of Hematology, USA.

Ghetie, et al., "Evaluation of Ricin A Chain-containing Immunotoxins Directed against CD19 and CD22 Antigens on Normal and Malignant Human B-Cells as Potential Reagents for *in Vivo* Therapy[1]," *Cancer Research*, 1988, pp. 2610-2617, vol. 48, No. 9.

Gillies, et al., "High-level expression of chimeric antibodies using adapted cDNA variable region cassettes," *Journal of Immunological Methods*, 1989, pp. 191-202, vol. 125, Elsevier Science Publishers B.V. (Biomedical Division), USA.

Goldenberg, "New Developments in Monoclonal Antibodies for Cancer Detection and Therapy," *CA-A Cancer Journal for Clinicians*, Jan./Feb. 1994, pp. 43-64, vol. 44, No. 1, Ortho Biotech, Inc., USA.

Goldenberg, et al., "Targeting, Dosimetry, and Radioimmunotherapy of B-Cell Lymphomas With Iodine-131-Labelled LL2 Monoclonal Antibody," *Journal of Clinical Oncology*, Apr. 1991, pp. 548-564, vol. 9, No. 4, W.B. Saunders Company, Harcourt Brace Jovanovich, Inc., Philadelphia London Toronto Montreal Sydney Tokyo.

Goodman, et al., "The Pharmacological Basis of Therapeutics," Fifth Edition, 1975, MacMillan Publishing Co., Inc. USA.

Goodman, et al., "New Perspectives on the Approach to Chronic Lymphocytic Leukemia," *Leukemia and Lymphoma*, 1996, pp. 1-10, vol. 22, Nos. 1 / 2, Hardwood Acedemic Publishers, The Netherlands.

Green, et al., "Antigen-specific human monoclonal antibodies from mice engineered with human Ig heavy and light chain YACs," *Nature Genetics*, May 1994, pp. 13-21, vol. 7, No. 1, USA.

Hasan, et al., "Laser-Induced Selective Cytotoxicity Using Monoclonal Antibody-Chromophore Conjugates," *Immunity to Cancer*, 1989, pp. 471-477, vol. II, Alan R. Liss, Inc., USA.

Hekman, et al., "Initial experience with treatment of human B cell lymphoma with anti-CD19 monoclonal antibody," *Cancer Immunology Immunotherapy*, 1991, pp. 364-372, vol. 32, No. 6, Springer-Verlag, The Netherlands.

Hugues, et al., Conjugation of methotrexate to poly(L-lysine) increases drug transport and overcomes drug resistance in cultured cells, *Proc. Natl. Acad. Sci. USA*, Aug. 1978, pp. 3867-3870, vol. 75.

Huse, et al., "Generation of a Large Combination Library of the Immunoglobulin Repertoire in Phage Lambda," *Research Article*, Dec. 8, 1989, pp. 1275-1281, vol. 246.

Johnson, et al., "Human antibody engineering," *Current Opinion in Structural Biology*, 1993, pp. 564-571, vol. 3, Cambridge Antibody Technology Ltd., United Kingdom.

Jones, et al., "Replacing the complementarity-determining regions in a human antibody with those from a mouse," *Nature*, May 29, 1986, pp. 522-525, vol. 321, No. 6069, Laboratory of Molecular Biology, Medical Research Council, United Kingdom.

Giulio Jori, et al., (EDS.), "Photodynamic Therapy of Tumors and Other Diseases," Lectures/paper given at the meeting hold at Alghero (Italy), May 1-4, 1985.

Kaminski, et al., "Radioimmunotherapy of B-Cell Lymphoma with [131I] Anti-B1 (Anti-CD20) Antibody," *The New England Journal of Medicine*, Aug. 12, 1993, pp. 459-465, vol. 329, No. 7, Massachusetts Medical Society, USA.

"Continuous cultures of fused cells secreting antibdy of predefined specificity," *Nature*, Aug. 7, 1975, pp. 495-497, vol. 256, No. 5517, MRC Laboratory of Molecular Biology, United Kingdom.

Larrick, et al., "PCR Amplification of Antibody Genes," *Methods*, Apr. 1991, pp. 106-110, vol. 2, No. 2, Academic Press, Inc., Harcourt Brace Jovanovich, Publishers, San Diego New York Boston London Sydney Tokyo Toronto.

Leung, et al., "Chimerization of LL2, a Rapidly Internalizing Antibody Specific for B Cell Lymphoma," *Hydridoma*, Dec. 1994, pp. 469-476, vol. 13, No. 6, Mary Ann Liebert, Inc., New Jersey, USA.

Leung, et al., "Engineering a Unique Glycosylation Site for Site-Specific Conjugation of Haptens to Antibody Fragments," *The Journal of Immunology*, Jun. 1, 1995, pp. 5919-5926, vol. 154, No. 11, The American Association of Immunologists, USA.

Leung, et al., "Construction and Characterization of a Humanized, Internalizing, B-Cell (CD22)-Specific, Leukemia/Lymphoma Antibody, LL2," *Molecular Immunology*, 1995, pp. 1413-1427, vol. 32, No. 17/18, Elsevier Science Ltd., Great Britain.

Liu, et al., "Production of a Mouse-Human Chimeric Monoclonal Antibody to CD20 with Potent Fc-Dependent Biologic Activity," *The Journal of Immunology*, Nov. 15, 1987, pp. 3521-3526, vol. 139, No. 10, The American Association of Immunologists, USA.

Lonberg, et al., "Antigen-specific human antibodies from mice comprising four distinct genetic modifications," *Nature*, Apr. 28, 1994, pp. 856-859, vol. 368.

Longo, "Immunotherapy for non-Hodgkin's Lymphoma," *Current Opinion in Oncology*, Sep. 1996, pp. 353-359, vol. 8, No. 5, Rapid Science Publishers, USA.

Losman, et al., Generation of a High-Producing Clone of a Humanized Anti-B-Cell Lymphoma Monoclonal Antibody (hLL2), *Cancer Supplement*, Dec. 15, 1997, pp. 2660-2666, vol. 80, No. 12, Published for the American Cancer Society by John Wiley & Sons, Inc., USA.

Majolino, et al., "High-dose cyclophosphamide, etoposide and BCNU (CVB) with autologous stem cell rescue in malignant lymphomas," *European Journal of Haematology*, Jul. 1993, pp. 18-24, vol. 51, No. 1.

Mew, et al., "Ability of Specific Monoclonal Antibodies and Conventional Antisera Conjugated to Hematoporphyrin to Label and Kill Selected Cell Lines Subsequent to Light Activation," *Cancer Research*, Sep. 1985, pp. 4380-4386, vol. 45.

McCafferty, et al., "Phage antibodies: filamentous phage displaying antibody variable domains," *Nature*, Dec. 6, 1990, pp. 552-554, vol. 348, No. 6301.

Mack, et al., "A small bispecific antibody construct expressed as a functional single-chain molecule with high tumor cell cytotoxicity,"*Proc. Natl. Acad. Sci. USA*, Jul. 1995, pp. 7021-7025, vol. 92.

Maloney, et al., "Phase I Clinical Trial Using Escalating Single-Dose Infusion of Chimeric Anti-CD20 Monoclonal Antibody (IDEC-C2B8) in Patients With Recurrent B-Cell Lymphoma," *Blood*, Oct. 15, 1994, pp. 2457-2466, vol. 84, No. 8.

Mendez, et al., "Functional transplant of megabase human immunoglobulin loci recapitulates human antibody response in mice," *Nature Genetics*, Feb. 15, 1997, pp. 146-156, vol. 15, No. 2.

Mew, et al., "Photoimmunotherapy: Treatment of Animal Tumors with Tumor-Specific Monoclonai Antibody-Hematoporphyrin Conjugates," *The Journal of Immunology*, Mar. 1983, pp. 1473-1477, vol. 130, No. 3.

Nisonoff, et al., "Separation of Univalent Fragments from the Bivalent Rabbit Antibody Molecule by Reduction of Disulfide Bonds," *Archives of Biochemistry and Biophysics*, 1960, pp. 130-244, vol. 89, No. 2.

Orlandi, et al., "Cloning immunoglobulin variable domains for expression by the polymerase chain reaction," *Proc. Natl. Acad. Sci. USA*, May 1989, pp. 3833-3837, vol. 86.

Oseroff, et al., "Strategies for selective cancer photochemotherapy: antibody-targeted and selective carcinoma cell photolysis," *Photochemistry and Photobiology*, 1987, pp. 83-96, vol. 46, No. 1.

Oseroff, et al., Antibody-targeted photolysis: Selective photodestruction of human T-cell leukemia cells using monoclonal antibody-chlorin $e_6$ conjugates, *Proc. Natl. Acad. Sci, USA*, Nov. 1986, pp. 8744-8748, vol. 83.

Pastan, et al., "Immunotoxins," *Cell*, Dec. 5, 1986, pp. 641-648, vol. 47, No. 5.

Pelegrin, et al., "Antibody-Fluorescein Conjugates for Photoimmunodiagnosis of Human Colon Carcinoma in Nude Mice," *Cancer*, May 15, 1991, pp. 2529-2537, vol. 67, No. 10.

Porter, "The Hydrolysis of Rabbit γ-Globulin and Antibodies with Crystalline Papain," *The Biochemical Journal*, Sep. 1959, pp. 119-126, vol. 73, No. 1.

Press, et al., "Radiolabeled-Antibody Therapy of B-Cell Lymphoma With Autologous Bone Marrow Support," Oct. 21, 1993, pp. 1219-1224, vol. 329, No. 17.

Press, et al., "Phase II trial of $^{131}$I-B1 (anti-CD20) antibody therapy with autologous stem cell transplanation for relapsed B cell lymphomas," Aug. 5, 1995, pp. 336-340, vol. 346, No. 8791.

Press, et al., "Monoclonal Antibody 1F5 (Anti-CD20) Serotherapy of Human B Cell Lymphomas," *Blood*, Feb. 1987, pp. 584-591, vol. 69, No. 2.

Press, et al., "Treatment of Refractory Non-Hodgkin's Lymphoma With Radiolabeled MB-1 (Anti-CD37) Antibody," *Journal of Clinical Oncology*, Aug. 1989, pp. 1027-1038, vol. 7, No. 8.

Price, "Production and characterization of synthetic peptide-derived antibodies," pp. 60-85.

Raag, et al., "Single-chain Fvs," *The FASEB Journal*, Jan. 1995, pp. 73-80, vol. 9.

Riechmann, et al., "Reshaping human antibodies for therapy," *Nature*, Mar. 1988, pp. 323-327, vol. 332, No. 6162.

Robinson, et al., "Chimeric mouse-human anti-carcinoma antibodies that mediate different anti-tumor cell biological activities," *Human Antibodies and Hybridomas*, Apr. 1991, pp. 84-93, vol. 2, No. 2.

Saltzman, et al., "Transport rates of proteins in porous materials with known microgeometry," *Biophysical Journal*, Jan. 1989, pp. 163-171, vol. 55, No. 1, Published for the Biophysical Society by The Rockefeller University Press, USA.

Sambrook, et al., "Molecular Cloning," *A Laboratory Manual, Second Edition*, 1989, Cold Spring Harbor Laboratory Press, USA.

Sanger, et al., "DNA sequencing with chain-terminating inhibitors," *Proc. Natl. Acad. Sci USA*, Biochemistry, Dec. 1977, pp. 5463-5467, vol. 74, No. 12, Medical Research Council Laboratory of Molecular Biology, England.

Shan, et al., "Signaling events involved in anti-CD20-induced apoptosis of malignant human B cells," *Cancer Immunology Immunother*, 2000, pp. 673-683, Springer-Verlag, OW Press, USA.

Sherwood, et al., "Controlled Antibody Delivery Systems," *Biotechnology*, Nov. 1992, pp. 1446-1449, vol. 10.

Shih, et al., "A Fluorouridine-Anti-Cea Immunoconjugate Is Therapeutically Effective In A Human Colonic Cancer Xenograft Model," *International Journal of Cancer*, Dec. 15, 1990, pp. 1101-1106, vol. 46, No. 6, Publication of the International Union Against Cancer, Wiley-Liss, Inc., USA.

Shih, et al., "Site-Specific Linkage Of Methotrexate To Monoclonal Antibodies Using An Intermediate Carrier," *International Journal of Cancer*, May 15, 1988, pp. 832-839, vol. 41, No. 5, Publication of the International Union Against Cancer, Alan R. Liss, Inc., USA.

Shopes, "A Genetically Engineered Human IgG Mutant With Enhanced Cytolytic Activity," *The Journal Of Immunology*, May 1, 1992, pp. 2918-2922, vol. 148, No. 9, The American Association of Immunologists, USA.

Singer, et al., "Optimal Humanization of 1B4, an Anti-CD18 Murine Monoclonal Antibody, Is Achieved by Correct Choice of Human V-Region Framework Sequences," *The Journal Of Immunology*, Apr. 1, 1993, pp. 2844-2857, vol. 150, No. 7, The American Association of Immunologists, USA.

Tatsuta, et al., "Diagnosis of Gastric Cancers With Fluorescein-Labeled Monoclonal Antibodies to Carcinoembryonic Antigen," *Lasers in Surgery and Medicine*, 1989, pp. 422-426, vol. 9, No. 4, Alan R. Liss, Inc., USA.

Taylor, et al., "Human immunoglobulin transgenes undergo rearrangement, somatic mutation and class switching in mice that lack endogenous Igm," *International Immunology*, 1994, pp. 579-591, vol. 6, No. 4, Oxford University Press, USA.

Tempest, et al., "Reshaping A Human Monoclonal Antibody To Inhibit Human Respiratory Syncytial Virus Infection *In Vivo*," *Bio/Technology*, Mar. 1991, pp. 266-271, vol. 9.

Upeslacis, et al., "Modification Of Antibodies By Chemical Methods," *Monoclonal Antibodies: Principles and Applications*, 1995, pp. 187-230, Chapter 4, Wiley-Liss, Inc., USA.

Van Den Bergh, "Light and porphyrins in cancer therapy," *Chemistry in Britain*, May 1986, pp. 430-439.

Verhoeyen, et al., "Reshaping Human Antibodies: Grafting an Antilysozyme Activity," *Science*, Mar. 25, 1988, pp. 1534-1536, vol. 239, Medical Research Council Laboratory of Molecular Biology, England.

Ward, et al., "Genetic Manipulation And Expression Of Antibodies," *Monoclonal Antibodies: Principles and Applications*, 1995, pp. 137-185, Chapter 3, Wiley-Liss, Inc., USA.

Werner, et al., "Appropriate Mammalian Expression Systems for Biopharmaceuticals," *Arzneimittel Forschung Drug Research*, Aug. 1998, pp. 789-880, vol. 48, Germany.

Wong, "Chemistry of Protein Conjugation and Cross-Linking," 1991, CRC Press, Inc., USA.

Yu, et al."Peptide-Antibody Conjugates For Tumour Therapy: A MHC-Class-II-Restricted Tetanus Toxin Peptide Coupled To An Anti-Ig Light Chain Antibody Can Induce Cytotoxic Lysis Of A Human B-Cell Lymphoma By Specific CD4 T Cells," *International Journal of Cancer*, Jan. 15, 1994, pp. 244-248, vol. 56, No. 2, Publication of the International Union Against Cancer, Wiley-Liss, Inc., USA.

\* cited by examiner

A20Vk

```
GACATTCAGCTGACCCAGTCTCCAGCAATCCTGTCTGCATCTCCAGGGGAGAAGGTCACAATGACTTGCAGGGCCAGCTCAAGTGTAAGT      90
---------+---------+---------+---------+---------+---------+---------+---------+---------+
CTGTAAGTCGACTGGGTCAGAGGTCGTTAGGACAGACGTAGAAGTCCCCTCTTCCAGTGTTACTGAACGTCCGGTCGAGTTCACATTCA
         1         10                  20                        27 29 30
         D  I  Q  L  T  Q  S  P  A  I  L  S  A  S  P  G  E  K  V  T  M  T  C  R  A  S  S  S  V  S    30
                                                                           CDR1

TACATCCACTGGTTCCAGCAGAAGCCAGGATCCTCCCCCAAACCCTGGATTTATGCCACATCCAACCTGGCTTCTGGAGTCCCTGTTCGC      180
---------+---------+---------+---------+---------+---------+---------+---------+---------+
ATGTAGGTGACCAAGGTCGTCTTCGGTCCTAGGAGGGGGTTTGGGACCTAAATACGGTGTAGGTTGGACCGAAGACCTCAGGGACAAGCG
                          40                            50
 Y  I  H  W  F  Q  Q  K  P  G  S  S  P  K  P  W  I  Y  A  T  S  N  L  A  S  G  V  P  V  R    60
                                                   CDR2

TTCAGTGGCAGTGGGTCTGGGACTTCTTACTCTCTCTCACAATCAGCAGAGTGGAGGCTGAAGATGCTGCCACTTATTACTGCCAGCAGTGG      270
---------+---------+---------+---------+---------+---------+---------+---------+---------+
AAGTCACCGTCACCCAGACCCTGAAGAATGAGAGAGAGTGTTAGTCGTCTCACCTCCGACTTCTACGACGGTGAATAATGACGGTCGTCACC
                          70                            80                            90
 F  S  G  S  G  T  S  Y  S  L  T  I  S  R  V  E  A  E  D  A  A  T  Y  Y  C  Q  Q  W    90

ACTAGTAACCCACCCACGTTCGGAGGGGGACCAAGCTGGAGATCTAAC                                              359
---------+---------+---------+---------+-------
TGATCATTGGGTGGGTGCAAGCCTCCCCCCTGGTTCGACCTCTAGATTG
                          100
 T  S  N  P  P  T  F  G  G  G  T  K  L  E  I                                                 105
 CDR3
```

```
GTACAACTGCAGCAGCCTGGGGCTGAGCTGGTGAAGCCTGGGGCCTCAGTGAAGATGTCCTGCAAGGCTTCTGGCTACACATTTACCAGT
------+---------+---------+---------+---------+---------+---------+---------+---------+   90
CATGTTGACGTCGTCGGACCCCGACTCGACCACTTCGGACCCCGGAGTCACTTCTACAGGACGTTCCGAAGACCGATGTGTAAATGGTCA
 2                  10                  20                  30
 V  Q  L  Q  Q  P  G  A  E  L  V  K  P  G  A  S  V  K  M  S  C  K  A  S  G  Y  T  F  T  S

TACAATATGCACTGGGTAAAACAGACACCTGGTCGGGGCCTGGAATGGATTGGAGCTATTTATCCCGGAAATGGTGATACTTCCTACAAT
------+---------+---------+---------+---------+---------+---------+---------+---------+  180
ATGTTATACGTGACCCATTTTGTCTGTGGACCAGCCCCGGACCTTACCTAACCTCGATAAATAGGGCCTTTACCACTATGAAGGATGTTA
                    40                  50    52 A              60
 Y  N  M  H  W  V  K  Q  T  P  G  R  G  L  E  W  I  G  A  I  Y  P  G  N  G  D  T  S  Y  N
 CDR1                                                    CDR 2

CAGAAGTTCAAAGGCAAGGCCACATTGACTGCAGACAAATCCTCCAGCACAGCCTACATGCAGCTCAGCAGCCTGACATCTGAGGACTCT
------+---------+---------+---------+---------+---------+---------+---------+---------+  270
GTCTTCAAGTTTCCGTTCCGGTTCCGGTGTAACTGACGTCTGTTTAGGAGGTCGTGTGGATGTACGTCGAGTCGTCGAGTCGTCCTGAGA
                    70                  80    82 A B C
 Q  K  F  K  G  K  A  T  L  T  A  D  K  S  S  S  T  A  Y  M  Q  L  S  S  L  T  S  E  D  S
 Q  K  F  K  G

GCGGTCTATTACTGTGCAAGATCGACTTACTACGGCGGTGACTGGTACTTCGATGTCTGGGGCCAAGGGACCACGGTCACCGTCTCCTCA
------+---------+---------+---------+---------+---------+---------+---------+---------+  360
CGCCAGATAATGACACGTTCTAGCTGAATGATGCCGCCACTGACCATGAAGCTACAGACCCCGGTTCCCTGGTGCCAGTGGCAGAGGAGT
                    90                100 A B C D                 110
 A  V  Y  Y  C  A  R  S  T  Y  Y  G  G  D  W  Y  F  D  V  W  G  Q  G  T  T  V  T  V  S  S
                  CDR3
```

```
GACATCCAGCTGACCCAGTCTCCAGCAATCCTGTCTGCATCTCCAGGGGAGAAGGTCACAATGACTTGCAGGGCCAGCTCAAGTGTAAGT    90
  1                                              10                               20                  27 29 30
  D   I   Q   L   T   Q   S   P   A   I   L   S   A   S   P   G   E   K   V   T   M   T   C   R   A   S   S   S   V   S
                                                                                              CDR1

TACATCCACTGGTTCCAGCAGAAGCCAGGATCCTCCCCCAAACCCTGGATTTATGCCACATCCAACCTGGCTTCTGGAGTCCCTGTTCGC    180
                        40                               50                               60
  Y   I   H   W   F   Q   Q   K   P   G   S   S   P   K   P   W   I   Y   A   T   S   N   L   A   S   G   V   P   V   R
                                                           CDR2

TTCAGTGGCAGTGGGTCTGGGACTTCTTACTCTCTCACAATCAGCAGAGTGGAGGCTGAAGATGCTGCCACTTATTACTGCCAGCAGTGG    270
                        70                               80                               90
  F   S   G   S   G   S   G   T   S   Y   S   L   T   I   S   R   V   E   A   E   D   A   A   T   Y   Y   C   Q   Q   W

ACTAGTAACCCACCCACGTTCGGAGGGGGGACCAAGCTGGAGATCAAA    318
                        100                  107
  T   S   N   P   P   T   F   G   G   G   T   K   L   E   I   K
  CDR3
```

```
CAGGTCCAACTGCAGCAGCCTGGGGCTGAGCTGGTGAAGCCTGGGGCCTCAGTGAAGATGTCCTGCAAGGCTTCTGGCTACACATTTACC     90
  1                                  10                         20                      30
  Q  V  Q  L  Q  Q  P  G  A  E  L  V  K  P  G  A  S  V  K  M  S  C  K  A  S  G  Y  T  F  T

AGTTACAATATGCACTGGGTAAAACAGACACCTGGTCGGGGCCTGGAATGGATTGGAGCTATTTATCCCGGAAATGGTGATACTTCCTAC    180
              40                              50     52 A
  S  Y  N  M  H  W  V  K  Q  T  P  G  R  G  L  E  W  I  G  A  I  Y  P  G  N  G  D  T  S  Y
         CDR1                                           CDR 2

AATCAGAAGTTCAAAGGCAAGGCCACATTGACTGCAGACAAATCCTCCAGCACAGCCTACATGCAGCTCAGCAGCCTGACATCTGAGGAC    270
 60                        70                         80   82 A B C
  N  Q  K  F  K  G  K  A  T  L  T  A  D  K  S  S  S  T  A  Y  M  Q  L  S  S  L  T  S  E  D

TCTGCGGTCTATTACTGTGCAAGATCGACTTACTACGGGGTGACTGGTACTTCGATGTCTGGGGCCAAGGGACCACGGTCACCGTCTCC    360
                      90          100 A B C D                  110
  S  A  V  Y  Y  C  A  R  S  T  Y  Y  G  D  W  Y  F  D  V  W  G  Q  G  T  T  V  T  V  S
                           CDR3

TCA                                                                                          363
113
 S
```

Figure 2B.

```
           1        10        20        30       40
EU_VH      PVQLVQSGAEVKKPGSSVKVSCKASGGTFSRSAIIWVRQA
cA20VH     Q···Q·P···LV···A···M······Y··TSYNMH··K·T
hA20VH1    Q···Q·····················Y··TSYNMH··K··
hA20VH2    Q···Q·····················Y···SYNMH·····

50 52 A      60        70
EU_VH      PGQGLEWMGGIVPMFGPPNYAQKFQGRVTITADESTNTAY
cA20VH     ··R····I·A·Y·GN·DTS·N···K·KA·L···K·SS···
hA20VH1    ········I·A·Y·GN·DTS·N···K·KA·L··········
hA20VH2    ··········A·Y·GN·DTS·N···K··A············

80 82 A B C      90        100 A B C D
EU_VH      MELSSLRSEDTAFYFCAGGYGIYS----PEEYNGGLVTVS
cA20VH     ·Q····T···S·V·Y··RSTYYGGDWYFDV
hA20VH1    ················Y··RSTYYGGDWYFDV
hA20VH2    ···················RSTYYGGDWYFDV 103    110 113
NEWM_VH    WGQGSLVTVSS
cA20VH     ····TT·····
hA20VH1    ····TT·····
hA20VH2    ····TT·····
```

Figure 4A.

```
              1                    10                  20                  30                40
REIVk    DIQMTQSPSSLSASVGDRVTITCQASQDIIKYLNWYQQTP
cA20Vk   ...L...AI....P.EK..M...R..S-SVS.IH..F..K.
hA20Vk   ...L...........M...R..S-SVS.IH..F..K.

50                  60                  70                80
REIVk    GKAPKLLIYEASNLQAGVPSRFSGSGSGTDYTFTISSLQP
cA20Vk   .SS..PW...AT...AS....V.......S.SL...RVEA
hA20Vk   .....PW...AT...AS....V..................

90                 100           107
REIVk    EDIATYYCQQYQSLPYTFGQGTKLQIT
cA20Vk   ...A.......WT.N.P....G....E..K
hA20Vk   ...........WT.N.P....G....E..K
```

Figure 4B.

```
                XbaI
                tctagacacaggacctcaccATGGGATGGAGCTGTATCATCCTCTTCTTGGTAGCAACAGCTACAggta    -91
                                     M  G  W  S  C  I  I  L  F  L  V  A  T  A  T       -5

AggggctcacagtagcaggcttgaggtctggacatatatgggtgacaatgacatccacttgcctttctctccacAGGTGTCCACTCC    -1
                                                                          G  V  H  S     -1
     PvuII
GACATCCAGCTGACCCAGTCTCCATCATCTCTGAGCGCGATCTGTTGGAGATAGGGTCACTATGACTTGTAGGGCCAGCTCAAGTGTAAGT    90
 D  I  Q  L  T  Q  S  P  S  S  L  S  A  S  V  G  D  R  V  T  M  T  C  R  A  S  S  V  S      30
                                                                         ‾‾‾‾‾‾‾‾‾‾‾‾‾‾
                                                                               CDR1

TACATCCACTGGTTCCAGCAGAAACCAGGGAAAGCACCTAAACCCTGGATTTATGCCACTTCGAACCTGGCTTCTGGTGTCCCTGTCCGA    180
 Y  I  H  W  F  Q  Q  K  P  G  K  A  P  K  P  W  I  Y  A  T  S  N  L  A  S  G  V  P  V  R     61
 ‾‾‾‾                                              ‾‾‾‾‾‾‾‾‾‾‾‾‾‾‾‾‾‾‾‾‾‾‾‾
                                                            CDR2

TTCTCTGGCAGCGGATCTGGGACAGATTACACTTTCACCATCAGCTCTCTTCAACCAGAAGACATTGCAACATATTATTGTCAGCAGTGG    270
 F  S  G  S  G  S  G  T  D  Y  T  F  T  I  S  L  Q  P  E  D  I  A  T  Y  Y  C  Q  Q  W       91
                              BglII/BclI                                        BamHI
ACTAGTAACCCACCCACGTTCGGTGGAGGGACCAAGCTGGAGATCAAACgtgagtagagaatttaaactttgcttcctcagttggatcc    357
 T  S  N  P  P  T  F  G  G  G  T  K  L  E  I  K                                              107
 ‾‾‾‾‾‾‾‾‾‾‾‾
    CDR3
```

Figure 5A.

```
                                                                                    XhoI
ctcgagcacacaggacctcaccATGGGATGGAGCTGTATCATCCTCTTCTTGGTAGCAACAGCTACAggta      -91
                      M   G   W   S   C   I   I   L   F   L   V   A   T        -5

AggggctcacagtagcaggcttgaggtctggacatatatgggtgacaatgacatccactttgcctttctctccacAGGTGTCCACTCC   -1
                                                                    G V H S    -1
              PstI
CAGGTCCAACTGCAGCAATCAGGGGCTGAAGTCAAGAAACCTGGGTCATCGGTCTCCTGCAAGGCTTCTGGCTACACCTTTACT      90
 Q   V   Q   L   Q   Q   S   G   A   E   V   K   K   P   G   S   S   V   K   V   S   C   K   A   S   G   Y   T   F   T    30

AGTTACAATATGCACTGGGTCAAGCAGGCACCTGGACAGGGTCTGGAATGGATTGGAGCTATTATCCCGAAATGGTGATACTTCCTAC      180
 S   Y   N   M   H   W   V   K   Q   A   P   G   Q   G   L   E   W   I   G   A   I   Y   P   G   N   G   D   T   S   Y    59
 —————CDR1——————                                                 ————————————CDR2————————

AATCAGAAGTTCAAGGGTAAAGCCACACTGACTGCCGACGAATCCACCAATACAGCCTACATGGAGCTGAGCAGCCTGAGGTCTGAGGAC     270
 N   Q   K   F   K   G   K   A   T   L   T   A   D   E   S   T   N   T   A   Y   M   E   L   S   S   L   R   S   E   D    86

BstEII
ACGGCATTTTATTACTGTGCAAGATCGACTTACTACGGGGTGGTGACTTTGATGTCTGGGGCCAAGGCACCACGGTCACCGTCTCC       360
 T   A   F   Y   Y   C   A   R   S   T   Y   Y   G   G   D   W   Y   F   D   V   W   G   Q   G   T   T   V   T   V   S    112
                         ————————————————CDR3————————————————

TCAGgtgagtccttacaacctctctctctttctattcagcttaaatagatttactgcatttgttgggggaaatgtgtgtctgaatttc      450
 S                                                                                              113

Aggtcatgaaggactaggacaccttgggagtcagaaaggtcattgggagcccgggctgatgcagacagacatcctcagctcccagact     540

BamHI
tcatggccagagatttataggatcc                                                                   565

Figure 5B.
```

```
      XhoI
      ctcgagcacacaggacctcaccATGGGATGGAGCTGTATCATCCTCTTCTTGGTAGCAACAGCTACAggta           -91
             M  G  W  S  C  I  I  L  F  L  V  A  T  A  T                               -5

AggggctcacagtagcaggcttgaggtctgagtgacatatatgggtgacaatgacatcccactttgccttctctccaCAGGTGTCCACTCC    -1
                                                                         G  V  H  S    -1

CAGGTCCAACTGCAGCAATCAGGGCTGAAGTCAAGAAACCTGGGTCATCAGTGAAGGTCTCCTGCAAGGCTTCTGGCTACACCTTTAGT    90
 Q  V  Q  L  Q  Q  S  G  A  E  V  K  K  P  G  S  S  V  K  V  S  C  K  A  S  G  Y  T  F  S     30

AGTTACAATATGCACTGGGTCAGAGACAGGCCACCTGGACAGGGTCTGGAATGGATGGGAGCTATTTATCCCGGAAATGGTGATACTTCCTAC  180
 S  Y  N  M  H  W  V  R  Q  A  P  G  Q  G  L  E  W  M  G  A  I  Y  P  G  N  G  D  T  S  Y     59
 CDR1                                                CDR2

AATCAGAAGTTCAAGGGTAGAGCCACAATAACTGCCGACGAATCCACCAATACAGCCTACATGGAGCTGAGCAGCCTGAGGTCTGAGGAC   270
 N  Q  K  F  K  G  R  A  T  I  T  A  D  E  S  T  N  T  A  Y  M  E  L  S  S  L  R  S  E  D     86

ACGGCATTTTATTTTGTGCAAGATCGACTTACTACGGCGGTGACTTGATGTCTGGGGCCAAGGCACCACGGTCACCGTCTCC           360
 T  A  F  Y  F  C  A  R  S  T  Y  Y  G  G  D  W  Y  F  D  V  W  G  Q  G  T  T  V  T  V  S    112
                      CDR3

TCAGgtgagtccttacaacctctctctcttctattcagcttaaatagatttactgcatttgttgtggggaaatgtgtgtatctgaattc     450
  S                                                                                          113

Aggtcatgaaggactagggacaccttgggagtcagaaagggtcattgggagcccgggctgatgcagacagacatcctcagctcccagact   540
      BamHI
Tcatggccagagatttataggatcc                                                                    565
```

Figure 5C.

```
      GCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCG   120
118   A   S   T   K   G   P   S   V   F   P   L   A   P   S   S   K   S   T   S   G   G   T   A   A   L   G   C   L   V   K   D   Y   F   P   E   P   V   T   V   S

TGGAACTCAGGCGCCCTGACCAGCGGCGTGCACACCTTCCCGGCTGTCCTACAGTCCTCAGGACTCTACTCCCTCAGCAGCGTTGTGACCGTGCCCTCCAGCAGCTTGGGCACCCAGACC   240
158   W   N   S   G   A   L   T   S   G   V   H   T   F   P   A   V   L   Q   S   S   G   L   Y   S   L   S   S   V   V   T   V   P   S   S   S   L   G   T   Q   T

TACATCTGCAACGTGAATCACAAGCCCAGCAACACCAAGGTGGACAAGAGAGTTGAGCCCAAATCTTGTGACAAAACTCACACATGCCCACCGTGCCCAGCACCTGAACTCCTGGGGGGA   360
198   Y   I   C   N   V   N   H   K   P   S   N   T   K   V   D   K   R   V   E   P   K   S   C   D   K   T   H   T   C   P   P   C   P   A   P   E   L   L   G   G

CCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGG   480
238   P   S   V   F   L   F   P   P   K   P   K   D   T   L   M   I   S   R   T   P   E   V   T   C   V   V   V   D   V   S   H   E   D   P   E   V   K   F   N   W

TACGTGGACGGCGTGGAGGTGCATAATGCCAAGACAAAGCCGCGGGAGGAGCAGTACAACAGCACGTACCGTGTGGTCAGCGTCCTCACCGTCCTGCACCAGGACTGGCTGAATGGCAAG   600
278   Y   V   D   G   V   E   V   H   N   A   K   T   K   P   R   E   E   Q   Y   N   S   T   Y   R   V   V   S   V   L   T   V   L   H   Q   D   W   L   N   G   K

GAGTACAAGTGCAAGGTCTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAG   720
318   E   Y   K   C   K   V   S   N   K   A   L   P   A   P   I   E   K   T   I   S   K   A   K   G   Q   P   R   E   P   Q   V   Y   T   L   P   P   S   R   E   E

ATGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTG   840
358   M   T   K   N   Q   V   S   L   T   C   L   V   K   G   F   Y   P   S   D   I   A   V   E   W   E   S   N   G   Q   P   E   N   N   Y   K   T   T   P   P   V

CTGGACTCCGACGGCTCCTTCTTCCTCTATAGCAAGCTCACCGTGGACAAGAGCAGGTGGCAGCAGGGGAACGTCTTCTCATGCTCCGTGATGCATGAGGCTCTGCACAACCACTACACG   960
398   L   D   S   D   G   S   F   F   L   Y   S   K   L   T   V   D   K   S   R   W   Q   Q   G   N   V   F   S   C   S   V   M   H   E   A   L   H   N   H   Y   T

CAGAAGAGCCTCTCCCTGTCTCCGGGTAAATGA                                                                                          993
438   Q   K   S   L   S   L   S   P   G   K   *
```

Fig. 7A. The CH sequence of hIgG1.

108 CGAACTGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAG 120
    R  T  V  A  A  P  S  V  F  I  F  P  P  S  D  E  Q  L  K  S  G  T  A  S  V  V  C  L  L  N  N  F  Y  P  R  E  A  K  V  Q

148 TGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAG 240
    W  K  V  D  N  A  L  Q  S  G  N  S  Q  E  S  V  T  E  Q  D  S  K  D  S  T  Y  S  L  S  S  T  L  T  L  S  K  A  D  Y  E

188 AAACACAAAGTCTACGCCTGCGAAGTCACCCATCAGGGCCTGAGTTCGCCCGTCACAAAGAGCTTCAACAGGGGAGAGTGTTGA 324
    K  H  K  V  Y  A  C  E  V  T  H  Q  G  L  S  S  P  V  T  K  S  F  N  R  G  E  C  *

Fig. 7B. The constant region sequence of human kappa chain.

SEQUENCE LISTING

<160> NUMBER OF SEQ ID NOS: 55

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ala Ser Ser Ser Val Ser Tyr Ile His
 1               5                  10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ala Ser Ser Ser Leu Ser Phe Met His
 1               5                  10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Ala Ser Ser Ser Val Ser Tyr Met His
 1               5                  10

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Thr Ser Asn Leu Ala Ser
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Gln Trp Thr Ser Asn Pro Pro Thr
 1               5

```
<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

His Gln Trp Ser Ser Asn Pro Leu Thr
 1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Gln Ser Phe Ser Asn Pro Pro Thr
 1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Tyr Asn Met His
 1               5

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ile Tyr Pro Gly Asn Gly Asp Thr Ser Tyr Asn Gln Lys Phe Lys
 1               5                  10                  15

Gly

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Thr Tyr Tyr Gly Gly Asp Trp Tyr Phe Asp Val
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
```

-continued

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Thr Tyr Tyr Gly Gly Asp Trp Tyr Phe Asn Val
 1               5                  10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser His Tyr Gly Ser Asn Tyr Val Asp Tyr Phe Asp Val
 1               5                  10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Val Tyr Tyr Ser Asn Ser Tyr Trp Tyr Phe Asp Val
 1               5                  10

<210> SEQ ID NO 14
<211> LENGTH: 120
<212> TYPE: DNA
<213> ORGANISM: Artificial Sequence
<220> FEATURE:
<223> OTHER INFORMATION: Description of Artificial Sequence: Primer

<400> SEQUENCE: 14
catctctgag cgcatctgtt ggagataggg tcactatgac ttgtagggcc agctcaagtg      60
taagttacat ccactggttc cagcagaaac cagggaaagc acctaaaccc tggatttatg     120

<210> SEQ ID NO 15
<211> LENGTH: 130
<212> TYPE: DNA
<213> ORGANISM: Artificial Sequence
<220> FEATURE:
<223> OTHER INFORMATION: Description of Artificial Sequence: Primer

<400> SEQUENCE: 15
ggtgtccctg tccgattctc tggcagcgga tctgggacag attacacttt caccatcagc      60
tctcttcaac cagaagacat tgcaacatat tattgtcagc agtggactag taacccaccc     120
acgttcggtg                                                            130

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 16
cagctgaccc agtctccatc atctctgagc gcatctgttg                            40

<210> SEQ ID NO 17

```
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 17
aggttcgaag tggcataaat ccagggttta ggtgct                           36

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 18
cacttcgaac ctggcttctg gtgtccctgt ccgattctc                        39

<210> SEQ ID NO 19
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 19
acgttagatc tccagcttgg tccctccacc gaacgtgggt gggtta                46

<210> SEQ ID NO 20
<211> LENGTH: 121
<212> TYPE: DNA
<213> ORGANISM: Artificial Sequence
<220> FEATURE:
<223> OTHER INFORMATION: Description of Artificial Sequence: Primer

<400> SEQUENCE: 20
ctgaagtcaa gaaacctggg tcatcggtga aggtctcctg caaggcttct ggctacacct    60
ttactagtta caatatgcac tgggtcaagc aggcacctgg acagggtctg gaatggattg   120
g                                                                  121

<210> SEQ ID NO 21
<211> LENGTH: 151
<212> TYPE: DNA
<213> ORGANISM: Artificial Sequence
<220> FEATURE:
<223> OTHER INFORMATION: Description of Artificial Sequence: Primer

<400> SEQUENCE: 21
atcagaagtt caagggtaaa gccacactga ctgccgacga atccaccaat acagcctaca    60
tggagctgag cagcctgagg tctgaggaca cggcatttta ttactgtgca agatcgactt   120
actacggcgg tgactggtac ttcgatgtct g                                 151

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 22
cagctgcagc aatcaggggc tgaagtcaag aaacctggg                         39
```

```
<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 23
ttccgggata aatagctcca atccattcca gaccctg                              37

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 24
atcccggaaa tggtgatact tcctacaatc agaagttcaa gggtaaagcc a              51

<210> SEQ ID NO 25
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 25
ggagacggtg accgtggtgc cttggcccca gacatcgaag taccag                    46

<210> SEQ ID NO 26
<211> LENGTH: 121
<212> TYPE: DNA
<213> ORGANISM: Artificial Sequence
<220> FEATURE:
<223> OTHER INFORMATION: Description of Artificial Sequence: Primer

<400> SEQUENCE: 26
ctgaagtcaa gaaacctggg tcatcagtga aggtctcctg caaggcttct ggctacacct     60
ttagtagtta caatatgcac tgggtcagac aggcacctgg acagggtctg gaatggatgg    120
g                                                                    121

<210> SEQ ID NO 27
<211> LENGTH: 151
<212> TYPE: DNA
<213> ORGANISM: Artificial Sequence
<220> FEATURE:
<223> OTHER INFORMATION: Description of Artificial Sequence: Primer

<400> SEQUENCE: 27
atcagaagtt caagggtaga gccacaataa ctgccgacga atccaccaat acagcctaca     60
tggagctgag cagcctgagg tctgaggaca cggcatttta tttttgtgca agatcgactt    120
actacggcgg tgactggtac ttcgatgtct g                                   151

<210> SEQ ID NO 28
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 28
ttccgggata aatagctccc atccattcca gaccctg                              37
```

```
<210> SEQ ID NO 29
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 29
atcccggaaa tggtgatact tcctacaatc agaagttcaa gggtagagcc a            51

<210> SEQ ID NO 30
<211> LENGTH: 13
<212> TYPE: DNA
<213> ORGANISM: Artificial Sequence
<220> FEATURE:
<223> OTHER INFORMATION: Description of Artificial Sequence: Synthetic
      HNB linker

<400> SEQUENCE: 30
agcttgcggc cgc                                                       13

<210> SEQ ID NO 31
<211> LENGTH: 13
<212> TYPE: DNA
<213> ORGANISM: Artificial Sequence
<220> FEATURE:
<223> OTHER INFORMATION: Description of Artificial Sequence: Synthetic
      HNB linker

<400> SEQUENCE: 31
gatcgcggcc gca                                                       13

<210> SEQ ID NO 32
<211> LENGTH: 319
<212> TYPE: DNA
<213> ORGANISM: Artificial Sequence
<220> FEATURE:
<223> OTHER INFORMATION: Description of Artificial Sequence: Synthetic
      DNA encoding light chain A20Vk sequence
<220> FEATURE:
<221> NAME/KEY: CDS
<222> LOCATION: (1)..(315)

<400> SEQUENCE: 32 gac att cag ctg acc cag tct cca gca atc ctg tct gca tct cca ggg       48
Asp Ile Gln Leu Thr Gln Ser Pro Ala Ile Leu Ser Ala Ser Pro Gly
  1               5                  10                  15 gag aag gtc aca atg act tgc agg gcc agc tca agt gta agt tac atc      96
Glu Lys Val Thr Met Thr Cys Arg Ala Ser Ser Ser Val Ser Tyr Ile
                 20                  25                  30 cac tgg ttc cag cag aag cca gga tcc tcc ccc aaa ccc tgg att tat     144
His Trp Phe Gln Gln Lys Pro Gly Ser Ser Pro Lys Pro Trp Ile Tyr
             35                  40                  45 gcc aca tcc aac ctg gct tct gga gtc cct gtt cgc ttc agt ggc agt     192
Ala Thr Ser Asn Leu Ala Ser Gly Val Pro Val Arg Phe Ser Gly Ser
         50                  55                  60 ggg tct ggg act tct tac tct ctc aca atc agc aga gtg gag gct gaa     240
Gly Ser Gly Thr Ser Tyr Ser Leu Thr Ile Ser Arg Val Glu Ala Glu
 65                  70                  75                  80 gat gct gcc act tat tac tgc cag cag tgg act agt aac cca ccc acg     288
Asp Ala Ala Thr Tyr Tyr Cys Gln Gln Trp Thr Ser Asn Pro Pro Thr
                 85                  90                  95 ttc gga ggg ggg acc aag ctg gag atc taac                            319
Phe Gly Gly Gly Thr Lys Leu Glu Ile
            100                 105
```

<210> SEQ ID NO 33
<211> LENGTH: 105
<212> TYPE: PRT
<213> ORGANISM: Artificial Sequence
<220> FEATURE:
<223> OTHER INFORMATION: Description of Artificial Sequence: Synthetic
      light chain A20Vk amino acid sequence

<400> SEQUENCE: 33

Asp Ile Gln Leu Thr Gln Ser Pro Ala Ile Leu Ser Ala Ser Pro Gly
 1               5                  10                  15

Glu Lys Val Thr Met Thr Cys Arg Ala Ser Ser Val Ser Tyr Ile
             20                  25                  30

His Trp Phe Gln Gln Lys Pro Gly Ser Ser Pro Lys Pro Trp Ile Tyr
         35                  40                  45

Ala Thr Ser Asn Leu Ala Ser Gly Val Pro Val Arg Phe Ser Gly Ser
     50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile
            100                 105

<210> SEQ ID NO 34
<211> LENGTH: 360
<212> TYPE: DNA
<213> ORGANISM: Artificial Sequence
<220> FEATURE:
<223> OTHER INFORMATION: Description of Artificial Sequence: Synthetic
      DNA encoding heavy chain A20VH sequence
<220> FEATURE:
<221> NAME/KEY: CDS
<222> LOCATION: (1)..(360)

<400> SEQUENCE: 34 gta caa ctg cag cag cct ggg gct gag ctg gtg aag cct ggg gcc tca      48
Val Gln Leu Gln Gln Pro Gly Ala Glu Leu Val Lys Pro Gly Ala Ser
 1               5                  10                  15 gtg aag atg tcc tgc aag gct tct ggc tac aca ttt acc agt tac aat      96
Val Lys Met Ser Cys Lys Ala Ser Gly Tyr Thr Phe Thr Ser Tyr Asn
             20                  25                  30 atg cac tgg gta aaa cag aca cct ggt cgg ggc ctg gaa tgg att gga     144
Met His Trp Val Lys Gln Thr Pro Gly Arg Gly Leu Glu Trp Ile Gly
         35                  40                  45 gct att tat ccc gga aat ggt gat act tcc tac aat cag aag ttc aaa     192
Ala Ile Tyr Pro Gly Asn Gly Asp Thr Ser Tyr Asn Gln Lys Phe Lys
     50                  55                  60 ggc aag gcc aca ttg act gca gac aaa tcc tcc agc aca gcc tac atg     240
Gly Lys Ala Thr Leu Thr Ala Asp Lys Ser Ser Ser Thr Ala Tyr Met
 65                  70                  75                  80 cag ctc agc agc ctg aca tct gag gac tct gcg gtc tat tac tgt gca     288
Gln Leu Ser Ser Leu Thr Ser Glu Asp Ser Ala Val Tyr Tyr Cys Ala
                 85                  90                  95 aga tcg act tac tac ggc ggt gac tgg tac ttc gat gtc tgg ggc caa     336
Arg Ser Thr Tyr Tyr Gly Gly Asp Trp Tyr Phe Asp Val Trp Gly Gln
                100                 105                 110 ggg acc acg gtc acc gtc tcc tca                                     360
Gly Thr Thr Val Thr Val Ser Ser
            115                 120

```
<210> SEQ ID NO 35
<211> LENGTH: 120
<212> TYPE: PRT
<213> ORGANISM: Artificial Sequence
<220> FEATURE:
<223> OTHER INFORMATION: Description of Artificial Sequence: Synthetic
      heavy chain A20VH amino acid sequence

<400> SEQUENCE: 35

Val Gln Leu Gln Gln Pro Gly Ala Glu Leu Val Lys Pro Gly Ala Ser
 1               5                  10                  15

Val Lys Met Ser Cys Lys Ala Ser Gly Tyr Thr Phe Thr Ser Tyr Asn
             20                  25                  30

Met His Trp Val Lys Gln Thr Pro Gly Arg Gly Leu Glu Trp Ile Gly
         35                  40                  45

Ala Ile Tyr Pro Gly Asn Gly Asp Thr Ser Tyr Asn Gln Lys Phe Lys
     50                  55                  60

Gly Lys Ala Thr Leu Thr Ala Asp Lys Ser Ser Thr Ala Tyr Met
 65                  70                  75                  80

Gln Leu Ser Ser Leu Thr Ser Glu Asp Ser Ala Val Tyr Tyr Cys Ala
                 85                  90                  95

Arg Ser Thr Tyr Tyr Gly Gly Asp Trp Tyr Phe Asp Val Trp Gly Gln
            100                 105                 110

Gly Thr Thr Val Thr Val Ser Ser
        115                 120

<210> SEQ ID NO 36
<211> LENGTH: 318
<212> TYPE: DNA
<213> ORGANISM: Artificial Sequence
<220> FEATURE:
<223> OTHER INFORMATION: Description of Artificial Sequence: Synthetic
      DNA encoding light chain cA20Vk sequence
<220> FEATURE:
<221> NAME/KEY: CDS
<222> LOCATION: (1)..(318)

<400> SEQUENCE: 36 gac atc cag ctg acc cag tct cca gca atc ctg tct gca tct cca ggg      48
Asp Ile Gln Leu Thr Gln Ser Pro Ala Ile Leu Ser Ala Ser Pro Gly
 1               5                  10                  15 gag aag gtc aca atg act tgc agg gcc agc tca agt gta agt tac atc      96
Glu Lys Val Thr Met Thr Cys Arg Ala Ser Ser Ser Val Ser Tyr Ile
             20                  25                  30 cac tgg ttc cag cag aag cca gga tcc tcc ccc aaa ccc tgg att tat     144
His Trp Phe Gln Gln Lys Pro Gly Ser Ser Pro Lys Pro Trp Ile Tyr
         35                  40                  45 gcc aca tcc aac ctg gct tct gga gtc cct gtt cgc ttc agt ggc agt     192
Ala Thr Ser Asn Leu Ala Ser Gly Val Pro Val Arg Phe Ser Gly Ser
     50                  55                  60 ggg tct ggg act tct tac tct ctc aca atc agc aga gtg gag gct gaa     240
Gly Ser Gly Thr Ser Tyr Ser Leu Thr Ile Ser Arg Val Glu Ala Glu
 65                  70                  75                  80 gat gct gcc act tat tac tgc cag cag tgg act agt aac cca ccc acg     288
Asp Ala Ala Thr Tyr Tyr Cys Gln Gln Trp Thr Ser Asn Pro Pro Thr
                 85                  90                  95 ttc gga ggg ggg acc aag ctg gag atc aaa                             318
Phe Gly Gly Gly Thr Lys Leu Glu Ile Lys
            100                 105

<210> SEQ ID NO 37
```

-continued

```
<211> LENGTH: 106
<212> TYPE: PRT
<213> ORGANISM: Artificial Sequence
<220> FEATURE:
<223> OTHER INFORMATION: Description of Artificial Sequence: Synthetic
      light chain cA20Vk amino acid sequence

<400> SEQUENCE: 37

Asp Ile Gln Leu Thr Gln Ser Pro Ala Ile Leu Ser Ala Ser Pro Gly
 1               5                  10                  15

Glu Lys Val Thr Met Thr Cys Arg Ala Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 38
<211> LENGTH: 363
<212> TYPE: DNA
<213> ORGANISM: Artificial Sequence
<220> FEATURE:
<223> OTHER INFORMATION: Description of Artificial Sequence: Synthetic
      DNA encoding heavy chain cA20VH sequence
<220> FEATURE:
<221> NAME/KEY: CDS
<222> LOCATION: (1)..(363)

<400> SEQUENCE: 38 cag gtc caa ctg cag cag cct ggg gct gag ctg gtg aag cct ggg gcc      48
Gln Val Gln Leu Gln Gln Pro Gly Ala Glu Leu Val Lys Pro Gly Ala
 1               5                  10                  15 tca gtg aag atg tcc tgc aag gct tct ggc tac aca ttt acc agt tac      96
Ser Val Lys Met Ser Cys Lys Ala Ser Gly Tyr Thr Phe Thr Ser Tyr
                20                  25                  30 aat atg cac tgg gta aaa cag aca cct ggt cgg ggc ctg gaa tgg att     144
Asn Met His Trp Val Lys Gln Thr Pro Gly Arg Gly Leu Glu Trp Ile
            35                  40                  45 gga gct att tat ccc gga aat ggt gat act tcc tac aat cag aag ttc     192
Gly Ala Ile Tyr Pro Gly Asn Gly Asp Thr Ser Tyr Asn Gln Lys Phe
        50                  55                  60 aaa ggc aag gcc aca ttg act gca gac aaa tcc tcc agc aca gcc tac     240
Lys Gly Lys Ala Thr Leu Thr Ala Asp Lys Ser Ser Ser Thr Ala Tyr
 65                  70                  75                  80 atg cag ctc agc agc ctg aca tct gag gac tct gcg gtc tat tac tgt     288
Met Gln Leu Ser Ser Leu Thr Ser Glu Asp Ser Ala Val Tyr Tyr Cys
                85                  90                  95 gca aga tcg act tac tac ggc ggt gac tgg tac ttc gat gtc tgg ggc     336
Ala Arg Ser Thr Tyr Tyr Gly Gly Asp Trp Tyr Phe Asp Val Trp Gly
            100                 105                 110 caa ggg acc acg gtc acc gtc tcc tca                                 363
Gln Gly Thr Thr Val Thr Val Ser Ser
        115                 120

<210> SEQ ID NO 39
<211> LENGTH: 121
```

```
<212> TYPE: PRT
<213> ORGANISM: Artificial Sequence
<220> FEATURE:
<223> OTHER INFORMATION: Description of Artificial Sequence: Synthetic
      heavy chain cA20VH amino acid sequence

<400> SEQUENCE: 39

Gln Val Gln Leu Gln Gln Pro Gly Ala Glu Leu Val Lys Pro Gly Ala
  1               5                  10                  15

Ser Val Lys Met Ser Cys Lys Ala Ser Gly Tyr Thr Phe Thr Ser Tyr
             20                  25                  30

Asn Met His Trp Val Lys Gln Thr Pro Gly Arg Gly Leu Glu Trp Ile
         35                  40                  45

Gly Ala Ile Tyr Pro Gly Asn Gly Asp Thr Ser Tyr Asn Gln Lys Phe
     50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Thr Tyr Tyr Gly Gly Asp Trp Tyr Phe Asp Val Trp Gly
            100                 105                 110

Gln Gly Thr Thr Val Thr Val Ser Ser
            115                 120

<210> SEQ ID NO 40
<211> LENGTH: 116
<212> TYPE: PRT
<213> ORGANISM: Homo sapiens

<400> SEQUENCE: 40

Pro Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Arg Ser
             20                  25                  30

Ala Ile Ile Trp Val Arg Gln Ala Pro Gly Gln Gly Leu Glu Trp Met
         35                  40                  45

Gly Gly Ile Val Pro Met Phe Gly Pro Pro Asn Tyr Ala Gln Lys Phe
     50                  55                  60

Gln Gly Arg Val Thr Ile Thr Ala Asp Glu Ser Thr Asn Thr Ala Tyr
 65                  70                  75                  80

Met Glu Leu Ser Ser Leu Arg Ser Glu Asp Thr Ala Phe Tyr Phe Cys
                 85                  90                  95

Ala Gly Gly Tyr Gly Ile Tyr Ser Pro Glu Glu Tyr Asn Gly Gly Leu
            100                 105                 110

Val Thr Val Ser
        115

<210> SEQ ID NO 41
<211> LENGTH: 121
<212> TYPE: PRT
<213> ORGANISM: Artificial Sequence
<220> FEATURE:
<223> OTHER INFORMATION: Description of Artificial Sequence: Synthetic
      ha20VH1 sequence

<400> SEQUENCE: 41

Gln Val Gln Leu Gln Gln Ser Gly Ala Glu Val Lys Lys Pro Gly Ser
  1               5                  10                  15

Ser Val Lys Val Ser Cys Lys Ala Ser Gly Tyr Thr Phe Thr Ser Tyr
```

```
                    20                  25                  30

Asn Met His Trp Val Lys Gln Ala Pro Gly Gln Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Glu Ser Thr Asn Thr Ala Tyr
65                  70                  75                  80

Met Glu Leu Ser Ser Leu Arg Ser Glu Asp Thr Ala Phe Tyr Tyr Cys
                85                  90                  95

Ala Arg Ser Thr Tyr Tyr Gly Gly Asp Trp Tyr Phe Asp Val Trp Gly
            100                 105                 110

Gln Gly Thr Thr Val Thr Val Ser Ser
        115                 120

<210> SEQ ID NO 42
<211> LENGTH: 121
<212> TYPE: PRT
<213> ORGANISM: Artificial Sequence
<220> FEATURE:
<223> OTHER INFORMATION: Description of Artificial Sequence: Synthetic
      ha20VH2 sequence

<400> SEQUENCE: 42

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Asn Met His Trp Val Arg Gln Ala Pro Gly Gln Gly Leu Glu Trp Met
            35                  40                  45

Gly Ala Ile Tyr Pro Gly Asn Gly Asp Thr Ser Tyr Asn Gln Lys Phe
        50                  55                  60

Lys Gly Arg Ala Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Ser Thr Tyr Tyr Gly Gly Asp Trp Tyr Phe Asp Val Trp Gly
            100                 105                 110

Gln Gly Thr Thr Val Thr Val Ser Ser
        115                 120

<210> SEQ ID NO 43
<211> LENGTH: 11
<212> TYPE: PRT
<213> ORGANISM: Homo sapiens

<400> SEQUENCE: 43

Trp Gly Gln Gly Ser Leu Val Thr Val Ser Ser
1               5                   10

<210> SEQ ID NO 44
<211> LENGTH: 107
<212> TYPE: PRT
<213> ORGANISM: Homo sapiens

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ile Lys Tyr
            20                  25                  30
```

```
Leu Asn Trp Tyr Gln Gln Thr Pro Gly Lys Ala Pro Lys Leu Leu Ile
             35                  40                  45

Tyr Glu Ala Ser Asn Leu Gln Ala Gly Val Pro Ser Arg Phe Ser Gly
 50                  55                  60

Ser Gly Ser Gly Thr Asp Tyr Thr Phe Thr Ile Ser Ser Leu Gln Pro
 65                  70                  75                  80

Glu Asp Ile Ala Thr Tyr Tyr Cys Gln Gln Tyr Gln Ser Leu Pro Tyr
                 85                  90                  95

Thr Phe Gly Gln Gly Thr Lys Leu Gln Ile Thr
            100                 105
```

<210> SEQ ID NO 45
<211> LENGTH: 516
<212> TYPE: DNA
<213> ORGANISM: Artificial Sequence
<220> FEATURE:
<223> OTHER INFORMATION: Description of Artificial Sequence: Synthetic
      DNA encoding light chain hA20 sequence

<400> SEQUENCE: 45

```
tctagacaca ggacctcacc atg gga tgg agc tgt atc atc ctc ttc ttg       50
                     Met Gly Trp Ser Cys Ile Ile Leu Phe Leu
                      1               5                  10 gta gca aca gct ac  aggtaaggggg ctcacagtag caggcttgag gtctggacat  104
Val Ala Thr Ala Thr
             15 atatatgggt gacaatgaca tccactttgc ctttctctcc ac a ggt gtc cac tcc  159
                                                Gly Val His Ser gac atc cag ctg acc cag tct cca tca tct ctg agc gca tct gtt gga  207
Asp Ile Gln Leu Thr Gln Ser Pro Ser Ser Leu Ser Ala Ser Val Gly
 20                  25                  30                  35 gat agg gtc act atg act tgt agg gcc agc tca agt gta agt tac atc  255
Asp Arg Val Thr Met Thr Cys Arg Ala Ser Ser Ser Val Ser Tyr Ile
                 40                  45                  50 cac tgg ttc cag cag aaa cca ggg aaa gca cct aaa ccc tgg att tat  303
His Trp Phe Gln Gln Lys Pro Gly Lys Ala Pro Lys Pro Trp Ile Tyr
             55                  60                  65 gcc act tcg aac ctg gct tct ggt gtc cct gtc cga ttc tct ggc agc  351
Ala Thr Ser Asn Leu Ala Ser Gly Val Pro Val Arg Phe Ser Gly Ser
         70                  75                  80 gga tct ggg aca gat tac act ttc acc atc agc tct ctt caa cca gaa  399
Gly Ser Gly Thr Asp Tyr Thr Phe Thr Ile Ser Ser Leu Gln Pro Glu
     85                  90                  95 gac att gca aca tat tat tgt cag cag tgg act agt aac cca ccc acg  447
Asp Ile Ala Thr Tyr Tyr Cys Gln Gln Trp Thr Ser Asn Pro Pro Thr
100                 105                 110                 115 ttc ggt gga ggg acc aag ctg gag atc aaa cgtgagtaga atttaaactt     497
Phe Gly Gly Gly Thr Lys Leu Glu Ile Lys
                120                 125 tgcttcctca gttggatcc                                              516
```

<210> SEQ ID NO 46
<211> LENGTH: 125
<212> TYPE: PRT
<213> ORGANISM: Artificial Sequence
<220> FEATURE:
<223> OTHER INFORMATION: Description of Artificial Sequence: Synthetic
      light chain hA20 amino acid sequence

<400> SEQUENCE: 46

```
Met Gly Trp Ser Cys Ile Ile Leu Phe Leu Val Ala Thr Ala Thr Gly
  1               5                  10                  15

Val His Ser Asp Ile Gln Leu Thr Gln Ser Pro Ser Ser Leu Ser Ala
            20                  25                  30

Ser Val Gly Asp Arg Val Thr Met Thr Cys Arg Ala Ser Ser Ser Val
        35                  40                  45

Ser Tyr Ile His Trp Phe Gln Gln Lys Pro Gly Lys Ala Pro Lys Pro
 50                  55                  60

Trp Ile Tyr Ala Thr Ser Asn Leu Ala Ser Gly Val Pro Val Arg Phe
 65                  70                  75                  80

Ser Gly Ser Gly Ser Gly Thr Asp Tyr Thr Phe Thr Ile Ser Ser Leu
                85                  90                  95

Gln Pro Glu Asp Ile Ala Thr Tyr Tyr Cys Gln Gln Trp Thr Ser Asn
            100                 105                 110

Pro Pro Thr Phe Gly Gly Gly Thr Lys Leu Glu Ile Lys
        115                 120                 125

<210> SEQ ID NO 47
<211> LENGTH: 726
<212> TYPE: DNA
<213> ORGANISM: Artificial Sequence
<220> FEATURE:
<223> OTHER INFORMATION: Description of Artificial Sequence: Synthetic
      DNA encoding heavy chain hA20VH1 sequence

<400> SEQUENCE: 47
ctcgagcaca caggacctca cc atg gga tgg agc tgt atc atc ctc ttc ttg       52
                         Met Gly Trp Ser Cys Ile Ile Leu Phe Leu
                          1               5                  10 gta gca aca gct ac  aggtaagggg ctcacagtag caggcttgag gtctggacat       106
Val Ala Thr Ala Thr
                15 atatatgggt gacaatgaca tccactttgc ctttctctcc ac a ggt gtc cac tcc      161
                                                Gly Val His Ser cag gtc caa ctg cag caa tca ggg gct gaa gtc aag aaa cct ggg tca      209
Gln Val Gln Leu Gln Gln Ser Gly Ala Glu Val Lys Lys Pro Gly Ser
 20                  25                  30                  35 tcg gtg aag gtc tcc tgc aag gct tct ggc tac acc ttt act agt tac      257
Ser Val Lys Val Ser Cys Lys Ala Ser Gly Tyr Thr Phe Thr Ser Tyr
                40                  45                  50 aat atg cac tgg gtc aag cag gca cct gga cag ggt ctg gaa tgg att      305
Asn Met His Trp Val Lys Gln Ala Pro Gly Gln Gly Leu Glu Trp Ile
            55                  60                  65 gga gct att tat ccc gga aat ggt gat act tcc tac aat cag aag ttc      353
Gly Ala Ile Tyr Pro Gly Asn Gly Asp Thr Ser Tyr Asn Gln Lys Phe
 70                  75                  80 aag ggt aaa gcc aca ctg act gcc gac gaa tcc acc aat aca gcc tac      401
Lys Gly Lys Ala Thr Leu Thr Ala Asp Glu Ser Thr Asn Thr Ala Tyr
        85                  90                  95 atg gag ctg agc agc ctg agg tct gag gac acg gca ttt tat tac tgt      449
Met Glu Leu Ser Ser Leu Arg Ser Glu Asp Thr Ala Phe Tyr Tyr Cys
100                 105                 110                 115 gca aga tcg act tac tac ggc ggt gac tgg tac ttc gat gtc tgg ggc      497
Ala Arg Ser Thr Tyr Tyr Gly Gly Asp Trp Tyr Phe Asp Val Trp Gly
                120                 125                 130 caa ggc acc acg gtc acc gtc tcc tca ggtgagtcct tacaacctct            544
Gln Gly Thr Thr Val Thr Val Ser Ser
            135                 140 ctcttctatt cagcttaaat agattttact gcatttgttg gggggaaat gtgtgtatct      604
```

```
gaatttcagg tcatgaagga ctagggacac cttgggagtc agaaagggtc attgggagcc      664
cgggctgatg cagacagaca tcctcagctc ccagacttca tggccagaga tttataggat      724
cc                                                                     726
```

<210> SEQ ID NO 48
<211> LENGTH: 140
<212> TYPE: PRT
<213> ORGANISM: Artificial Sequence
<220> FEATURE:
<223> OTHER INFORMATION: Description of Artificial Sequence: Synthetic heavy chain hA20VH1 amino acid sequence

<400> SEQUENCE: 48

```
Met Gly Trp Ser Cys Ile Ile Leu Phe Leu Val Ala Thr Ala Thr Gly
 1               5                  10                  15

Val His Ser Gln Val Gln Leu Gln Gln Ser Gly Ala Glu Val Lys Lys
             20                  25                  30

Pro Gly Ser Ser Val Lys Val Ser Cys Lys Ala Ser Gly Tyr Thr Phe
         35                  40                  45

Thr Ser Tyr Asn Met His Trp Val Lys Gln Ala Pro Gly Gln Gly Leu
     50                  55                  60

Glu Trp Ile Gly Ala Ile Tyr Pro Gly Asn Gly Asp Thr Ser Tyr Asn
 65                  70                  75                  80

Gln Lys Phe Lys Gly Lys Ala Thr Leu Thr Ala Asp Glu Ser Thr Asn
                 85                  90                  95

Thr Ala Tyr Met Glu Leu Ser Ser Leu Arg Ser Glu Asp Thr Ala Phe
            100                 105                 110

Tyr Tyr Cys Ala Arg Ser Thr Tyr Tyr Gly Gly Asp Trp Tyr Phe Asp
        115                 120                 125

Val Trp Gly Gln Gly Thr Thr Val Thr Val Ser Ser
    130                 135                 140
```

<210> SEQ ID NO 49
<211> LENGTH: 726
<212> TYPE: DNA
<213> ORGANISM: Artificial Sequence
<220> FEATURE:
<223> OTHER INFORMATION: Description of Artificial Sequence: Synthetic DNA encoding heavy chain hA20VH2 sequence

<400> SEQUENCE: 49

```
ctcgagcaca caggacctca cc atg gga tgg agc tgt atc atc ctc ttc ttg       52
                         Met Gly Trp Ser Cys Ile Ile Leu Phe Leu
                          1               5                  10 gta gca aca gct ac  aggtaagggg ctcacagtag caggcttgag gtctggacat       106
Val Ala Thr Ala Thr
                15 atatatgggt gacaatgaca tccactttgc ctttctctcc ac a ggt gtc cac tcc       161
                                                Gly Val His Ser cag gtc caa ctg cag caa tca ggg gct gaa gtc aag aaa cct ggg tca       209
Gln Val Gln Leu Gln Gln Ser Gly Ala Glu Val Lys Lys Pro Gly Ser
 20                  25                  30                  35 tca gtg aag gtc tcc tgc aag gct tct ggc tac acc ttt agt agt tac       257
Ser Val Lys Val Ser Cys Lys Ala Ser Gly Tyr Thr Phe Ser Ser Tyr
                 40                  45                  50 aat atg cac tgg gtc aga cag gca cct gga cag ggt ctg gaa tgg atg       305
Asn Met His Trp Val Arg Gln Ala Pro Gly Gln Gly Leu Glu Trp Met
             55                  60                  65
```

```
gga gct att tat ccc gga aat ggt gat act tcc tac aat cag aag ttc      353
Gly Ala Ile Tyr Pro Gly Asn Gly Asp Thr Ser Tyr Asn Gln Lys Phe
         70                  75                  80 aag ggt aga gcc aca ata act gcc gac gaa tcc acc aat aca gcc tac      401
Lys Gly Arg Ala Thr Ile Thr Ala Asp Glu Ser Thr Asn Thr Ala Tyr
 85                  90                  95 atg gag ctg agc agc ctg agg tct gag gac acg gca ttt tat ttt tgt      449
Met Glu Leu Ser Ser Leu Arg Ser Glu Asp Thr Ala Phe Tyr Phe Cys
100                 105                 110                 115 gca aga tcg act tac tac ggc ggt gac tgg tac ttc gat gtc tgg ggc      497
Ala Arg Ser Thr Tyr Tyr Gly Gly Asp Trp Tyr Phe Asp Val Trp Gly
             120                 125                 130 caa ggc acc acg gtc acc gtc tcc tca ggtgagtcct tacaacctct            544
Gln Gly Thr Thr Val Thr Val Ser Ser
             135             140 ctcttctatt cagcttaaat agattttact gcatttgttg gggggaaat gtgtgtatct    604 gaatttcagg tcatgaagga ctagggacac cttgggagtc agaaagggtc attgggagcc    664
cgggctgatg cagacagaca tcctcagctc ccagacttca tggccagaga tttataggat    724
cc                                                                   726

<210> SEQ ID NO 50
<211> LENGTH: 140
<212> TYPE: PRT
<213> ORGANISM: Artificial Sequence
<220> FEATURE:
<223> OTHER INFORMATION: Description of Artificial Sequence: Synthetic
      heavy chain hA20VH2 amino acid sequence

<400> SEQUENCE: 50

Met Gly Trp Ser Cys Ile Ile Leu Phe Leu Val Ala Thr Ala Thr Gly
  1               5                  10                  15

Val His Ser Gln Val Gln Leu Gln Gln Ser Gly Ala Glu Val Lys Lys
             20                  25                  30

Pro Gly Ser Ser Val Lys Val Ser Cys Lys Ala Ser Gly Tyr Thr Phe
         35                  40                  45

Ser Ser Tyr Asn Met His Trp Val Arg Gln Ala Pro Gly Gln Gly Leu
     50                  55                  60

Glu Trp Met Gly Ala Ile Tyr Pro Gly Asn Gly Asp Thr Ser Tyr Asn
 65                  70                  75                  80

Gln Lys Phe Lys Gly Arg Ala Thr Ile Thr Ala Asp Glu Ser Thr Asn
                 85                  90                  95

Thr Ala Tyr Met Glu Leu Ser Ser Leu Arg Ser Glu Asp Thr Ala Phe
            100                 105                 110

Tyr Phe Cys Ala Arg Ser Thr Tyr Tyr Gly Gly Asp Trp Tyr Phe Asp
        115                 120                 125

Val Trp Gly Gln Gly Thr Thr Val Thr Val Ser Ser
    130                 135                 140

<210> SEQ ID NO 51
<211> LENGTH: 993
<212> TYPE: DNA
<213> ORGANISM: Homo sapiens
<220> FEATURE:
<221> NAME/KEY: CDS
<222> LOCATION: (1)..(993)

<400> SEQUENCE: 51 gcc tcc acc aag ggc cca tcg gtc ttc ccc ctg gca ccc tcc tcc aag       48
Ala Ser Thr Lys Gly Pro Ser Val Phe Pro Leu Ala Pro Ser Ser Lys
```

-continued

| | | | | | | |
|---|---|---|---|---|---|---|
| 1 | | 5 | | 10 | | 15 | agc acc tct ggg ggc aca gcg gcc ctg ggc tgc ctg gtc aag gac tac    96
Ser Thr Ser Gly Gly Thr Ala Ala Leu Gly Cys Leu Val Lys Asp Tyr
             20                  25                  30 ttc ccc gaa ccg gtg acg gtg tcg tgg aac tca ggc gcc ctg acc agc   144
Phe Pro Glu Pro Val Thr Val Ser Trp Asn Ser Gly Ala Leu Thr Ser
         35                  40                  45 ggc gtg cac acc ttc ccg gct gtc cta cag tcc tca gga ctc tac tcc   192
Gly Val His Thr Phe Pro Ala Val Leu Gln Ser Ser Gly Leu Tyr Ser
     50                  55                  60 ctc agc agc gtg gtg acc gtg ccc tcc agc agc ttg ggc acc cag acc   240
Leu Ser Ser Val Val Thr Val Pro Ser Ser Ser Leu Gly Thr Gln Thr
 65                  70                  75                  80 tac atc tgc aac gtg aat cac aag ccc agc aac acc aag gtg gac aag   288
Tyr Ile Cys Asn Val Asn His Lys Pro Ser Asn Thr Lys Val Asp Lys
                 85                  90                  95 aga gtt gag ccc aaa tct tgt gac aaa act cac aca tgc cca ccg tgc   336
Arg Val Glu Pro Lys Ser Cys Asp Lys Thr His Thr Cys Pro Pro Cys
             100                 105                 110 cca gca cct gaa ctc ctg ggg gga ccg tca gtc ttc ctc ttc ccc cca   384
Pro Ala Pro Glu Leu Leu Gly Gly Pro Ser Val Phe Leu Phe Pro Pro
         115                 120                 125 aaa ccc aag gac acc ctc atg atc tcc cgg acc cct gag gtc aca tgc   432
Lys Pro Lys Asp Thr Leu Met Ile Ser Arg Thr Pro Glu Val Thr Cys
     130                 135                 140 gtg gtg gtg gac gtg agc cac gaa gac cct gag gtc aag ttc aac tgg   480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag   528
Tyr Val Asp Gly Val Glu Val His Asn Ala Lys Thr Lys Pro Arg Glu
                 165                 170                 175 gag cag tac aac agc acg tac cgt gtg gtc agc gtc ctc acc gtc ctg   576
Glu Gln Tyr Asn Ser Thr Tyr Arg Val Val Ser Val Leu Thr Val Leu
             180                 185                 190 cac cag gac tgg ctg aat ggc aag gag tac aag tgc aag gtc tcc aac   624
His Gln Asp Trp Leu Asn Gly Lys Glu Tyr Lys Cys Lys Val Ser Asn
         195                 200                 205 aaa gcc ctc cca gcc ccc atc gag aaa acc atc tcc aaa gcc aaa ggg   672
Lys Ala Leu Pro Ala Pro Ile Glu Lys Thr Ile Ser Lys Ala Lys Gly
     210                 215                 220 cag ccc cga gaa cca cag gtg tac acc ctg ccc cca tcc cgg gag gag   720
Gln Pro Arg Glu Pro Gln Val Tyr Thr Leu Pro Pro Ser Arg Glu Glu
225                 230                 235                 240 atg acc aag aac cag gtc agc ctg acc tgc ctg gtc aaa ggc ttc tat   768
Met Thr Lys Asn Gln Val Ser Leu Thr Cys Leu Val Lys Gly Phe Tyr
                 245                 250                 255 ccc agc gac atc gcc gtg gag tgg gag agc aat ggg cag ccg gag aac   816
Pro Ser Asp Ile Ala Val Glu Trp Glu Ser Asn Gly Gln Pro Glu Asn
             260                 265                 270 aac tac aag acc acg cct ccc gtg ctg gac tcc gac ggc tcc ttc ttc   864
Asn Tyr Lys Thr Thr Pro Pro Val Leu Asp Ser Asp Gly Ser Phe Phe
         275                 280                 285 ctc tat agc aag ctc acc gtg gac aag agc agg tgg cag cag ggg aac   912
Leu Tyr Ser Lys Leu Thr Val Asp Lys Ser Arg Trp Gln Gln Gly Asn
     290                 295                 300 gtc ttc tca tgc tcc gtg atg cat gag gct ctg cac aac cac tac acg   960
Val Phe Ser Cys Ser Val Met His Glu Ala Leu His Asn His Tyr Thr
305                 310                 315                 320 cag aag agc ctc tcc ctg tct ccg ggt aaa tga                       993

```
Gln Lys Ser Leu Ser Leu Ser Pro Gly Lys
            325                 330

<210> SEQ ID NO 52
<211> LENGTH: 330
<212> TYPE: PRT
<213> ORGANISM: Homo sapiens

<400> SEQUENCE: 52

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 53
<211> LENGTH: 324
<212> TYPE: DNA
<213> ORGANISM: Homo sapiens
```

<220> FEATURE:
<221> NAME/KEY: CDS
<222> LOCATION: (1)..(324)

<400> SEQUENCE: 53

| cga | act | gtg | gct | gca | cca | tct | gtc | ttc | atc | ttc | ccg | cca | tct | gat | gag | 48 |
|-----|-----|-----|-----|-----|-----|-----|-----|-----|-----|-----|-----|-----|-----|-----|-----|----|
| Arg | Thr | Val | Ala | Ala | Pro | Ser | Val | Phe | Ile | Phe | Pro | Pro | Ser | Asp | Glu | |
| 1 | | | | 5 | | | | | 10 | | | | | 15 | | |

| cag | ttg | aaa | tct | gga | act | gcc | tct | gtt | gtg | tgc | ctg | ctg | aat | aac | ttc | 96 |
|-----|-----|-----|-----|-----|-----|-----|-----|-----|-----|-----|-----|-----|-----|-----|-----|----|
| Gln | Leu | Lys | Ser | Gly | Thr | Ala | Ser | Val | Val | Cys | Leu | Leu | Asn | Asn | Phe | |
| | | | 20 | | | | | 25 | | | | | 30 | | | |

| tat | ccc | aga | gag | gcc | aaa | gta | cag | tgg | aag | gtg | gat | aac | gcc | ctc | caa | 144 |
|-----|-----|-----|-----|-----|-----|-----|-----|-----|-----|-----|-----|-----|-----|-----|-----|-----|
| Tyr | Pro | Arg | Glu | Ala | Lys | Val | Gln | Trp | Lys | Val | Asp | Asn | Ala | Leu | Gln | |
| | | 35 | | | | | 40 | | | | | 45 | | | | |

| tcg | ggt | aac | tcc | cag | gag | agt | gtc | aca | gag | cag | gac | agc | aag | gac | agc | 192 |
|-----|-----|-----|-----|-----|-----|-----|-----|-----|-----|-----|-----|-----|-----|-----|-----|-----|
| Ser | Gly | Asn | Ser | Gln | Glu | Ser | Val | Thr | Glu | Gln | Asp | Ser | Lys | Asp | Ser | |
| 50 | | | | | 55 | | | | | 60 | | | | | | |

| acc | tac | agc | ctc | agc | agc | acc | ctg | acg | ctg | agc | aaa | gca | gac | tac | gag | 240 |
|-----|-----|-----|-----|-----|-----|-----|-----|-----|-----|-----|-----|-----|-----|-----|-----|-----|
| Thr | Tyr | Ser | Leu | Ser | Ser | Thr | Leu | Thr | Leu | Ser | Lys | Ala | Asp | Tyr | Glu | |
| 65 | | | | | 70 | | | | | 75 | | | | | 80 | |

| aaa | cac | aaa | gtc | tac | gcc | tgc | gaa | gtc | acc | cat | cag | ggc | ctg | agc | tcg | 288 |
|-----|-----|-----|-----|-----|-----|-----|-----|-----|-----|-----|-----|-----|-----|-----|-----|-----|
| Lys | His | Lys | Val | Tyr | Ala | Cys | Glu | Val | Thr | His | Gln | Gly | Leu | Ser | Ser | |
| | | | | 85 | | | | | 90 | | | | | 95 | | |

| ccc | gtc | aca | aag | agc | ttc | aac | agg | gga | gag | tgt | tga | 324 |
|-----|-----|-----|-----|-----|-----|-----|-----|-----|-----|-----|-----|-----|
| Pro | Val | Thr | Lys | Ser | Phe | Asn | Arg | Gly | Glu | Cys | | |
| | | 100 | | | | | 105 | | | | | |

<210> SEQ ID NO 54
<211> LENGTH: 107
<212> TYPE: PRT
<213> ORGANISM: Homo sapiens

<400> SEQUENCE: 54

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Synthetic
      linker sequence

<400> SEQUENCE: 55

Gly Gly Gly Ser
1

ANTI-CD20 ANTIBODIES AND FUSION PROTEINS THEREOF AND METHODS OF USE

This application claims priority to U.S. provisional application No. 60/356,132, filed Feb. 14, 2002 and to U.S. provisional application No. 80/416,232, filed Oct. 7, 2002.

BACKGROUND OF THE INVENTION

1. Field of the Invention

The present invention relates to humanized, chimeric and human anti-CD20 antibodies, particularly monoclonal antibodies (mAbs) therapeutic and diagnostic conjugates of humanized, chimeric and human anti-CD20 antibodies and methods of treating B cell lymphomas and leukemias and various autoimmune diseases using humanized, chimeric and human anti-CD20 antibodies. The present invention relates to antibody fusion proteins or fragments thereof comprising at least two anti-CD20 mAbs or fragments thereof or at least one anti-CD20 MAb or fragment thereof and at least one second MAb or fragment thereof, other than the antiCD20 MAb or fragment thereof. The humanized, chimeric and human anti-CD20 mAbs, fragments thereof, antibody fusion proteins thereof or fragments thereof may be administered alone, as a therapeutic conjugate or in combination with a therapeutic immunoconjugate, with other naked antibodies, or with therapeutic agents or as a diagnostic conjugate. The present invention relates to DNA sequences encoding humanized, chimeric and human anti-CD20 antibodies, and antibody fusion proteins, vectors and host cells containing the DNA sequences, and methods of making the humanized, chimeric and human anti-CD20 antibodies.

2. Background

The immune system of vertebrates consists of a number of organs and cell types which have evolved to accurately recognize foreign antigens, specifically bind to, and eliminate/destroy such foreign antigens. Lymphocytes, amongst others, are critical to the immune system. Lymphocytes are divided into two major sub-populations, T cells and B cells. Although inter-dependent, T cells are largely responsible for cell-mediated immunity and B cells are largely responsible for antibody production (humoral immunity).

In humans, each B cell can produce an enormous number of antibody molecules. Such antibody production typically ceases (or substantially decreases) when a foreign antigen has been neutralized. Occasionally, however, proliferation of a particular B cell will continue unabated and may result in a cancer known as a B cell lymphoma. B-cell lymphomas, such as the B-cell subtype of non-Hodgkin's lymphoma, are significant contributors to cancer mortality. The response of B-cell malignancies to various forms of treatment is mixed. For example, in cases in which adequate clinical staging of non-Hodgkin's lymphoma is possible, field radiation therapy can provide satisfactory treatment. Still, about one-half of the patients die from the disease. Devesa et al., *J. Nat'l Cancer Inst.* 79:701 (1987).

The majority of chronic lymphocytic leukemias are of B-cell lineage. Freedman, *Hematol. Oncol. Clin. North Am.* 4:405 (1990). This type of B-cell malignancy is the most common leukemia in the Western world. Goodman et al., *Leukemia and Lymphoma* 22:1 (1996). The natural history of chronic lymphocytic leukemia falls into several phases. In the early phase, chronic lymphocytic leukemia is an indolent disease, characterized by the accumulation of small mature functionally-incompetent malignant B-cells having a lengthened life span. Eventually, the doubling time of the malignant B-cells decreases and patients become increasingly symptomatic. While treatment can provide symptomatic relief, the overall survival of the patients is only minimally affected. The late stages of chronic lymphocytic leukemia are characterized by significant anemia and/or thrombocytopenia. At this point, the median survival is less than two years. Foon et al., *Annals Int. Medicine* 113:525 (1990). Due to the very low rate of cellular proliferation, chronic lymphocytic leukemia is resistant to cytotoxic drug treatment.

Traditional methods of treating B-cell malignancies, including chemotherapy and radiotherapy, have limited utility due to toxic side effects. The use of monoclonal antibodies to direct radionuclides, toxins, or other therapeutic agents offers the possibility that such agents can be delivered selectively to tumor sites, thus limiting toxicity to normal tissues. Also, the presence of B-cell antigens on these B-cell malignancies makes them optimal targets for therapy with unconjugated B-cell antibodies, such as against CD19, CD20, CD21, CD23, and CD22 markers on B-cells. HLA-DR and other antigens may serve as targets for normal and malignant B-cells, although they are also expressed on other cell types. Further, certain MUC1, MUC2, MUC3, and MUC4 antigens, preferably MUC1, are also expressed in different hematopoietic malignancies, including B-cell tumors expressing CD20 and other B-cell markers. Still other antigen targets, such as those associated with the vascular endothelium of tumors, including tenascin, vascular endothelium growth factor (VEGF), and placental growth factor (PlGF), as well as other categories of antigens associated with B-cell malignancies, such as oncogene products, are also suitable targets for said complementary antibodies for use in the present invention.

B cells comprise cell surface proteins which can be utilized as markers for differentiation and identification. One such human B-cell marker is the human B lymphocyte-restricted differentiation antigen Bp35, referred to as CD20. CD20 is expressed during early pre-B cell development and remains until plasma cell differentiation. CD20 is expressed on both normal B cells and malignant B cells whose abnormal growth can lead to B-cell lymphomas. Antibodies against the CD20 antigen have been investigated for the therapy of B-cell lymphomas. For example, a chimeric anti-CD20 antibody, designated as "IDEC-C2B8," has activity against B-cell lymphomas when provided as unconjugated antibodies at repeated injections of doses exceeding 500 mg per injection. Maloney et al., *Blood* 84:2457 (1994); Longo, *Curr. Opin. Oncol.* 8:353 (1996). About 50 percent of non-Hodgkin's patients, having the low-grade indolent form, treated with this regimen showed responses. Therapeutic responses have also been obtained using $^{131}$I-labeled B1 anti-CD20 murine monoclonal antibody when provided as repeated doses exceeding 600 mg per injection. Kaminski et al., *N. Engl. J. Med.* 329:459 (1993); Press et al., *N. Engl. J. Med.* 329:1219 (1993); Press et al, *Lancet* 346:336 (1995). However, these antibodies, whether provided as unconjugated forms or radiolabeled forms, have not shown high rates of objective and durable responses in patients with the more prevalent and lethal form of B-cell lymphoma, the intermediate or aggressive type. Therefore, a need exists to develop an immunotherapy for B-cell malignancies that achieves a therapeutic response of significant duration.

Additional studies targeting CD20 surface antigen have been demonstrated using an anti-CD20 murine monoclonal antibody, IF5, which was administered by continuous intravenous infusion to B cell lymphoma patients. Extremely high levels (>2 grams) of 1F5 were reportedly required to deplete circulating tumor cells, and the results were described as being "transient." Press et al., "Monoclonal Antibody 1F5 (Anti-CD20) Serotherapy of Human B-Cell Lymphomas." *Blood* 69/2:584–591 (1987). However, a potential problem with this approach is that non-human monoclonal antibodies (e.g., murine monoclonal antibodies) typically lack human effector functionality, i.e., they are unable to mediate complement-dependent lysis or lyse human target cells through antibody-dependent cellular toxicity or Fc-receptor mediated phagocytosis. Furthermore, non-human monoclonal antibodies can be recognized by the human host as a foreign protein and, therefore, repeated injections of such foreign antibodies can lead to the induction of immune responses leading to harmful hypersensitivity reactions. For murine-based monoclonal antibodies, this is often referred to as a Human Anti-Mouse Antibody (HAMA) response.

The use of chimeric antibodies is more preferred because they do not elicit as strong a HAMA response as munrine antibodies. Chimeric antibodies are antibodies which comprise portions from two or more different species. For example, Liu, A. Y. et al, "Production of a Mouse-Human Chimeric Monoclonal Antibody to CD20 with Potent Fc-Dependent Biologic Activity" *J. Immun*. 139/10:3521–3526 (1987), describe a mouse/human chimeric antibody directed against the CD20 antigen. See also, PCT Publication No. WO 88/04936. However, no information is provided as to the ability, efficacy or practicality of using such chimeric antibodies for the treatment of B cell disorders in the reference. It is noted that in vitro functional assays (e.g., complement-dependent lysis (CDC); antibody dependent cellular cytotoxicity (ADCC), etc.) cannot inherently predict the in vivo capability of a chimeric antibody to destroy or deplete target cells expressing the specific antigen. See, for example, Robinson, R. D. et al., "Chimeric mouse-human anti-carcinoma antibodies that mediate different anti-tumor cell biological activities," *Hum. Antibod. Hybridomas* 2:84–93 (1991) (chimeric mouse-human antibody having undetectable ADCC activity). Therefore, the potential therapeutic efficacy of a chimeric antibody can only truly be assessed by in vivo experimentation, preferably in the species of interest for the specific therapy.

One approach that has improved the ability of murine monoclonal antibodies to be effective in the treatment of B-cell disorders has been to conjugate a radioactive label or chemotherapeutic agent to the antibody, such that the label or agent is localized at the tumor site. For example, the above-referenced 1F5 antibody and other B-cell antibodies have been labeled with $^{131}$I and were reportedly evaluated for biodistribution in two patients. See Eary, J. F. et al., "Imaging and Treatment of B-Cell Lymphoma" *J. Nuc. Med.* 31/8:1257–1268 (1990); see also, Press, O. W. et al., "Treatment of Refractory Non-Hodgkin's Lymphoma with Radiolabeled MB-1 (Anti-CD37) Antibody" *J. Clin. Onc.* 7/8:1027–1038 (1989) (indication that one patient treated with $^{131}$I-labeled IF-5 achieved a partial response); Goldenberg, D. M. et al., "Targeting, Dosimetry and Radioimmunotherapy of B-Cell Lymphomas with $^{131}$I-Labeled LL2 Monoclonal Antibody" *J. Clin. Oncol.* 9/4:548–564 (1991) (three of eight patients receiving multiple injections reported to have developed a HAMA response to this CD22 murine antibody); Appelbaum, F. R. "Radiolabeled Monoclonal Antibodies in the Treatment of Non-Hodgkin's Lymphoma" *Hem./Oncol. Clinics of N. A.* 5/5:1013–1025 (1991) (review article); Press, O. W. et al. "Radiolabeled-Antibody Therapy of B-Cell Lymphoma with Autologous Bone Marrow Support." *New England Journal of Medicine* 329/17: 1219–12223 (1993) ($^{131}$I-labeled anti-CD20 antibody IF5 and B1); and Kaminski, M. G. et al "Radioimmunotherapy of B-Cell Lymphoma with [$^{131}$I] Anti-B1 (Anti-CD20) Antibody". *NEJM* 329/7:459 (1993) ($^{131}$I-labeled anti-CD20 antibody B1; hereinafter "Kaminski"); PCT published application WO 92/07466 (antibodies conjugated to chemotherapeutic agents such as doxorubicin or mitomycin). However, these approaches have not eliminated the obstacles associated with using murine antibodies, despite the fact that many patients with lymphoma who have received prior aggressive cytotoxic chemotherapy are immune suppressed, thus having lower HAMA rates than lymphoma patients who have not been heavily pretreated.

Autoimmune diseases are a class of diseases associated with B-cell disorders. Examples include immune-mediated thrombocytopenias, such as acute idiopathic thrombocytopenic purpura and chronic idiopathic thrombocytopenic purpura, myasthenia gravis, lupus nephritis, lupus erythematosus, and rheumatoid arthritis. The most common treatments are corticosteroids and cytotoxic drugs, which can be very toxic. These drugs also suppress the entire immune system, can result in serious infection, and have adverse affects on the bone marrow, liver and kidneys. Other therapeutics that have been used to treat Class III autoimmune diseases to date have been directed against T-cells and macrophages. There is a need for more effective methods of treating autoimmune diseases, particularly Class III autoimmune diseases.

To address the many issues related to B-cell disorders and their treatment, the present invention provides humanized, chimeric and human anti-CD20 monoclonal antibodies with the same complementarity determining regions (CDRs) that bind to the CD20 antigen of the present invention used alone, conjugated to a therapeutic agent or in combination with other treatment modalities, for the treatment of B cell lymphomas and leukemias and autoimmune disorders in humans and other mammals without the adverse responses associated with using murine antibodies.

SUMMARY OF THE INVENTION

Accordingly, the present invention provides humanized, chimeric and human anti-CD20 antibodies that bind to a human B cell marker, referred to as CD20, which is useful for the treatment and diagnosis of B-cell disorders, such as B-cell malignancies and autoimmune diseases.

The present invention further provides methods of treatment of mammalian subjects, such as humans or domestic animals, with one or more humanized, chimeric and human CD20 antibodies, alone, as an antibody fusion protein, as a therapeutic conjugate alone or as part of an antibody fusion protein, in combination, or as a multimodal therapy, with other antibodies, other therapeutic agents or immunomodulators or as an immunoconjugate linked to at least one therapeutic agent, therapeutic radionuclide or immunomodulator. These humanized, chimeric and human CD20 antibodies can also be used as a diagnostic imaging agent alone, in combination with other diagnostic imaging agents, and/or in conjunction with therapeutic applications.

The present invention additionally is directed to anti-CD20 mAbs or fragments thereof that contain specific murine CDRs or a combination of murine CDRs from more than one murine or chimeric anti-CD20 MAb that have specificity for CD20. These mAbs can be humanized, chimeric or human anti-CD20 mAbs. The present invention is further directed to light and/or heavy chain variable regions or fragments thereof of these anti-CD20 Mabs and to light and/or heavy chains or fragments thereof that have specficity for CD20.

The present invention is also directed to antibody fusion proteins comprising at least two anti-CD20mAbs or fragments thereof or a first MAb comprising an anti-CD20mAbs or fragments thereof and a second MAb.

The present invention is further directed to a therapeutic or diagnostic conjugates of the anti-CD20 mAbs or fragments thereof or antibody fusion proteins of the anti-CD20 mAbs or other mAbs or fragments thereof bound to at least one therapeutic agent or at least one diagnostic agent. Antibody fusion proteins with multiple therapeutic agents of the same or different type are encompassed by the present invention.

The present invention is additionally directed to a method of using the anti-CD20 mAbs or fragments thereof or antibody fusion proteins thereof or fragments thereof for therapy, either alone, in combination with each other, as the antibody component of a therapeutic immunoconjugate with one or more therapeutic agents or each administered in combination with one or more therapeutic agents or with an immunoconjugate with one or more therapeutic agents.

The present invention further is directed to a method of using the anti-CD20 mAbs or fragments thereof or antibody fusion proteins thereof or fragments thereof as a diagnostic bound to one or more diagnostic agents.

The present invention additionally is directed to a method of pretargeting a cell in a patients suffering from a B-cell lymphoma or leukemia or an autoimmune disease using an antibody fusion protein or fragment thereof of the present invention.

BRIEF DESCRIPTION OF THE FIGURES

FIG. 1 discloses the V gene sequences cloned by RT-PCR from a hybridoma cell line producing a murine anti-CD20, and the deduced amino acid sequences of the variable light (FIG. 1A) (SEQ ID NOS 32 & 33) and heavy chain (FIG. 1B) (SEQ ID NOS 34 & 35) of the A20 antibody, designated as A20Vk and A20VH, respectively. Underlined arrows indicate the sequences of the PCR primers used for cloning. The putative CDR region sequences, as defined by the Kabat numbering scheme, are shown in bold and underlined. Amino acid sequences are given as single-letter codes below the corresponding nucleotide sequence. The Kabat numbering scheme was used for amino acid residues. Amino acid residues numbered by a letter represent the insertion residue according to Kabat, and have the same number as that of the previous residue. For example, residues 82, 82A, 82B and 82C in FIG. 1B are indicated as 82 A, B, and C, respectively.

FIG. 2 discloses the Vk, the variable light chain, and the VH, the variable heavy chain, sequences of cA20, a chimeric anti-CD20 antibody. The CDR region sequences are shown in bold and underlined. The amino acid residues and the nucleotides are numbered sequentially and same numbering system is used for humanized V sequences. The light chain variable region is shown in FIG. 2A (SEQ ID NOS 36 & 37) and the heavy chain variable region is shown in FIG. 2B (SEQ ID NOS 38 & 39). The numbering system is the same as for FIG. 1. The restriction sites used for constructing cA20 are underlined.

FIG. 4 compares the amino acid sequences of the variable heavy chain (VH) and variable light chain (Vk) of human antibodies, and chimeric and humanzied anti-CD20 antibodies. FIG. 4A compares the amino acid sequences of the variable heavy chain (VH) of the human antibodies, EU (SEQ ID NO: 40) and NEWM (SEQ ID NO: 43) (FR4 only), the chimeric antibody, (cA20VH) (SEQ ID NO: 39) and two humanized antibodies, (hA20VH1 (SEQ ID NO: 41) and hA20VH2 (SEQ ID NO: 42)) and FIG. 4B compares the amino acid sequences of the variable light chain (Vk) of the human antibody, (REIVk) (SEQ ID NO: 44), a chimeric antibody, (cA20Vk) (SEQ ID NO: 37), and a humanized antibody, (hA20Vk) (residues 20–125 of SEQ ID NO: 46). Dots indicate that the residues in A20 are identical to the corresponding residue in the human antibody. The CDRs are identified as a boxed region. The Kabat numbering scheme was used to number the amino acid residues.

FIG. 5 discloses the nucleotide sequences of hA20 light chain V genes, (hA20Vk) (FIG. 5A) (SEQ ID NOS 45 & 46), and heavy chain V genes, hA20VH1 (FIG. 5B) (SEQ ID NOS 47 & 48) and hA20VH2 (FIG. 5C) (SEQ ID NOS 49 & 50), as well as the adjacent flanking sequences of the VKpBR2 (FIG. 5A) and VHpBS2 (FIGS. 5B and 5C) staging vectors, respectively. The non-translated nucleotide sequences are shown in lowercase. The restriction sites used for subcloning are underlined and indicated. The secretion signal peptide sequence is indicated by a double underline. Numbering of Vk and VH amino acid residues is same as that in FIG. 2.

FIG. 6 shows the results of a cell surface competitive binding assay to compare the binding activity of two humanized A20 antibodies, (hA20-1 and hA20-2), with that of A20, cA20 and a chimeric anti-CD20 MAb, c2B8.

FIG. 7 discloses the constant region of a human IgG1 (CH-hinge) (FIG. 7A) (SEQ ID NOS 51 & 52) and the constant region of a human kappa chain (Ck) (FIG. 7B) (SEQ ID NOS 53 & 54).

DETAILED DESCRIPTION OF THE INVENTION

1. Overview

Figure 3:
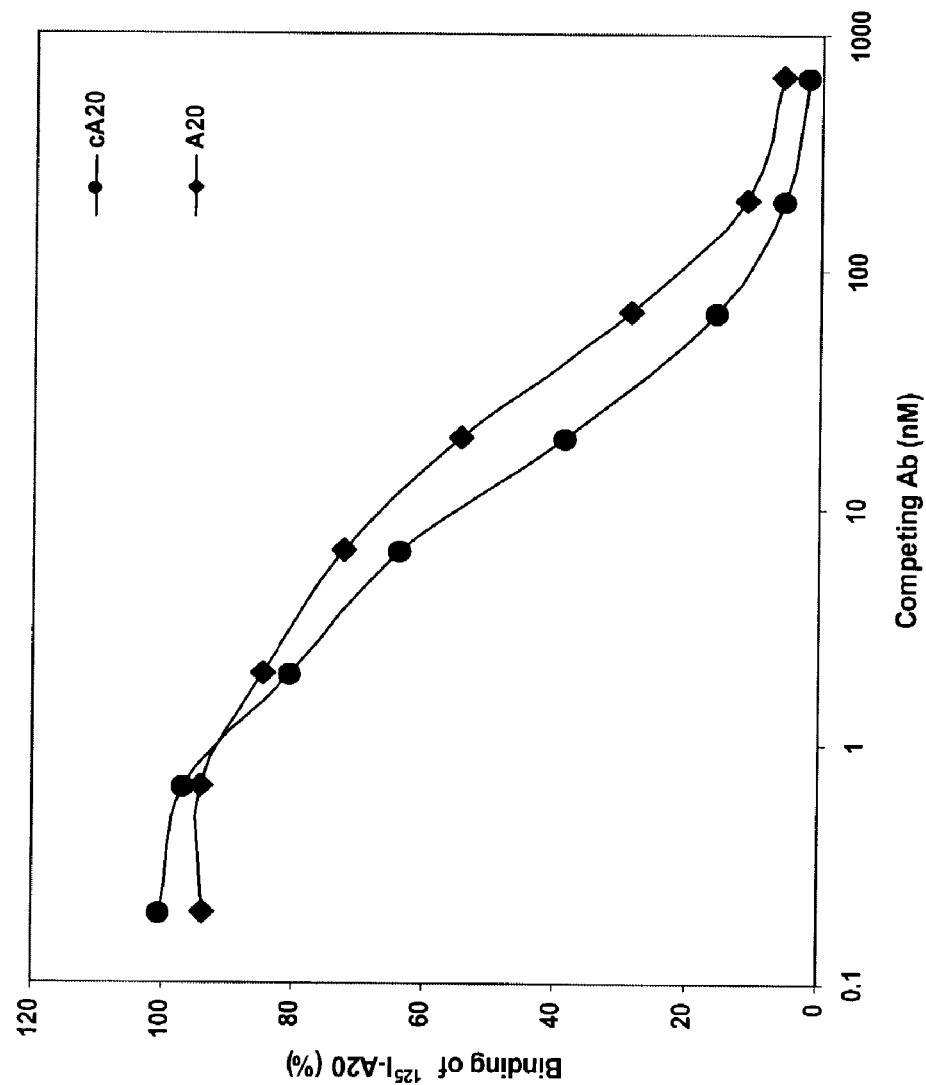
FIG. 3 shows a comparison of the binding affinities of the chimeric A20 (cA20), and murine A20, (A20), in a cell surface competitive binding assay against $^{125}$I-labled A20. Increasing concentrations of cA20 blocked the binding of radiolabeled A20 to Raji cells (as depicted by closed circles) in a comparable manner as that of murine A20 (depicted by closed diamonds).

As discussed above, anti-CD20 antibodies that are unconjugated or labeled with a therapeutic radionuclide, have failed to provide high rates of objective and lasting responses in patients with intermediate or aggressive forms of B-cell lymphoma. The present invention provides a humanized, a chimeric and a human anti-CD20 antibody, and antibody fusion proteins thereof, useful for treatment of mammalian subjects, humans and domestic animals, alone, as a conjugate or administered in combination with other therapeutic agents, including other naked antibodies and antibody therapeutic conjugates.

The anti-CD20 mAbs of the present invention contain specific murine CDRs or a combination of murine CDRs from more than one murine or chimeric anti-CD20 MAb that have specificity for the CD20 antigen. The anti-CD20 mAbs of the present invention are humanized, chimeric or human mAbs, light and/or heavy chains thereof or light and/or heavy chain variable regions thereof, and they contain the amino acids of the CDRs of a murine anti-CD20 MAb and retain substantially the B-cell and B-cell lymphoma and leukemia cell targeting of the murine anti-CD20 MAb. The CDRs of the light chain variable region of the anti-CD20 MAb comprises CDR1 comprising amino acids RASSSVSYIH (SEQ ID NO: 1), RASSSLSFMH (SEQ ID NO: 2) or RASSSVSYMH (SEQ ID NO: 3); CDR2 comprising amino acids ATSNLAS (SEQ ID NO: 4); and CDR3 comprising amino acids QQWTSNPPT (SEQ ID NO: 5), HQWSSNPLT (SEQ ID NO: 6) or QQSFSNPPT (SEQ ID NO: 7); and the CDRs of the heavy chain variable region of the anti-CD20 MAb comprises CDR1 comprising amino acids SYNMH (SEQ ID NO: 8); CDR2 comprising amino acids AIYPGNGDTSYNQKFKG (SEQ ID NO: 9) and CDR3 comprising amino acids STYYGGDWYFDV (SEQ ID NO: 10), STYYGGDWYFNV (SEQ ID NO: 11), SHYGSNYVDYFDV (SEQ ID NO: 12) or VVYYSNSYWYFDV (SEQ ID NO: 13). The humanized antibody further comprises the framework regions of the light and heavy chain constant regions of a human antibody.

In one embodiment, the humanized and chimeric MAb or fragment thereof does not contain the CDR3 of the heavy chain variable region comprising STYYGGDWyFNV (SEQ ID NO: 11). More preferably, CDR1 of the light chain variable region does not comprise RASSSLSFMH (SEQ ID NO: 2) when the CDR3 of the light chain variable region comprises HQWSSNPLT (SEQ ID NO: 6) and the CDR3 of the heavy chain variable region comprises SHYGSNYVDYFDV (SEQ ID NO: 12). In a further embodiment, the CDR3 of the heavy chain variable region does not comprise SHYGSNYVDYFDV (SEQ ID NO: 12) when the CDR1 of the light chain variable region comprises RASSSLSFMH (SEQ ID NO: 2) and the CDR3 of the light chain variable region comprises HQWSSNPLT (SEQ ID NO: 6). In another embodiment, the CDR1 of the light chain variable region does not comprise RASSSVSYMH (SEQ ID NO: 3) when the CDR3 of the light chain variable region comprises QQSFSNPPT (SEQ ID NO: 7) and the CDR3 of the heavy chain variable region comprises VVYYSNSYWYFDV (SEQ ID NO: 13).

Further, in another embodiment, the anti-CD20 monoclonal antibody (MAb) or fragment thereof does not contain CDR3 of the light chain variable region of amino acids QQSFSNPPT (SEQ ID NO: 7) when CDR1 of the light chain variable region comprises RASSSVSYMH (SEQ ID NO: 3) and the CDR3 of the heavy chain variable region comprises VVYYSNSYWYFDV (SEQ ID NO: 13). Additionally, the anti-CD20 MAb does not contain CDR3 of the heavy chain variable region with amino acids VVYYSNSYWYFDV (SEQ ID NO: 13) when the CDR1 of the light chain variable region comprises RASSSVSYMH (SEQ ID NO: 3) and the CDR3 of the light chain variable region comprises QQSFSNPPT (SEQ ID NO: 7).

In a preferred embodiment, the humanized anti-CD20 (hCD20) monoclonal antibody or antigen-binding fragment thereof comprising the complementarity determining regions (CDRs) of at least one murine anti-CD20 MAb variable region and the framework regions (FRs) of at least one human MAb variable region, wherein said humanized anti-CD20 MAb or fragment thereof retains substantially the B-cell and B-cell lymphoma and leukemia cell targeting of said murine anti-CD20 MAb. The humanized antibody's variable region may comprise a light chain variable region, a heavy chain variable region or a both light and heavy chain variable regions. The humanized antibody or fragment thereof may further comprise light and heavy chain constant regions of at least one human antibody.

The humanized anti-CD20 MAb or fragment thereof of the present invention comprises the CORs of a murine anti-CD20 MAb and the framework (FR) regions of the light and heavy chain variable regions of a human antibody, while retaining substantially the B-cell, and B-cell lymphoma and leukemia cell targeting of the parent murine anti-CD20 MAb, and wherein the CDRs of the light chain variable region of the murine anti-CD20 MAb comprises CDR1 comprising amino acids RASSSVSYIH (SEQ ID NO: 1), CDR2 comprising amino acids ATSNLAS (SEQ ID NO: 4) and CDR3 comprising QQWTSNPPT (SEQ ID NO: 5) and the CDRs of the heavy chain variable region of murine anti-CD20 MAb comprises CDR1 comprising amino acids SYNMH (SEQ ID NO: 8), CDR2 comprising amino acids AIYPGNGDTSYNQKFKG (SEQ ID NO: 9) and CDR3 comprising amino acids STYYGGDWYFDV (SEQ ID NO: 10). But the humanized anti-CD20 MAb or fragment thereof may further contain in the FRs of the light and heavy chain variable regions of the antibody at least one amino acid from the corresponding FRs of the murine MAb. The humanized MAbs may further contain the light and heavy chain constant regions of a human antibody. Specifically, the humanized anti-CD20 MAb or fragment thereof contains at least one amino acid residue 1, 5, 27, 30, 38, 48, 67, 68, 70, 95, 115 and 116 of the murine heavy chain variable region of FIG. 4A, designated as hA20VH1 or hA20VH2 and of at least one amino acid residue 4, 21, 35, 38, 45, 46, 59, 99, 104 and 106 of the murine light chain variable region FIG. 4B, designated hA20Vk. One or more of the murine amino acid sequences can be maintained in the human FR regions of the light and heavy variable chains if necessary to maintain proper binding or to enhance binding to the CD20 antigen. More preferably the humanized anti-CD20 MAb or fragment thereof of the present invention comprises the hA20Vk of FIG. 4B and the hA2VH1 of FIG. 4A. Most preferably, the humanized anti-CD20 MAb or fragment thereof of the present invention comprises the hA20Vk of FIG. 4B and the hA2VH2 of FIG. 4A. This latter sequence contains more human amino acid sequences in the FRs of the VH2 chain than the VH1, and thus is more humanized.

The preferred chimeric anti-CD20 (cCD20) MAb or fragment thereof of the present invention comprises the CDRs of a murine anti-CD20 MAb and the FR regions of the light and heavy chain variable regions of the murine anti-CD 20 MAb, i.e., the Fvs of the parental murine MAb, and the light and heavy chain constant regions of a human antibody, wherein the chimeric anti-CD20 MAb or fragment thereof retains substantially the B-cell, and B-cell lymphoma and leukemia cell targeting of the murine anti-CD20 MAb, wherein the CDRs of the light chain variable region of the chimeric anti-CD20 MAb comprise COR1 comprising amino acids RASSSVSYIH (SEQ ID NO: 1), RASSSLSFMH (SEQ ID NO: 2) or RASSSVSYMH (SEQ ID NO: 3); CDR2 comprising amino acids ATSNLAS (SEQ ID NO: 4); and CDR3 comprising amino acids QQWTSNPPT (SEQ ID NO: 5), HQWSSNPLT (SEQ ID NO: 6) or QQSFSNPPT (SEQ ID NO: 7); and the CDRs of the heavy chain variable region of the chimeric anti-CD20 MAb comprise CDR1 comprising amino acids SYNMH (SEQ ID NO: 8); CDR2 comprising amino acids AIYPGNGDTSYNQKFKG (SEQ ID NO: 9) and CDR3 comprising STYYGGDWYFDV (SEQ ID NO: 10), STYYGGDWYFNV (SEQ ID NO: 11), SHYGSNYVDYFDV (SEQ ID NO: 12) or VVYYSNSYWYFDV (SEQ ID NO: 13) with the following provisos:

(a) wherein the CDR3 of the heavy chain variable region does not comprise STYYGGDWYFNV (SEQ ID NO: 11), when the CDR1 of the light chain variable region comprises amino acids RASSSVSYIH (SEQ ID NO: 1), CDR2 of the light chain variable region comprises amino acids ATSNLAS (SEQ ID NO: 4), CDR3 of the light chain variable region comprises amino acids QQWTSNPPT (SEQ ID NO: 5), CDR1 of the heavy chain variable region comprises amino acids SYNMH (SEQ ID NO: 8), and CDR2 of the light chain variable region comprises amino acids AIYPGNGDTSYNQKFKG (SEQ ID NO: 9);

(b) wherein the CDR3 of the heavy chain variable region does not comprise SHYGSNYVDYFDV (SEQ ID NO: 12), when the COR1 of the light chain variable region comprises amino acids RASSSLSFMH (SEQ ID NO: 2), CDR2 of the light chain variable region comprises amino acids ATSNLAS (SEQ ID NO: 4), CDR3 of the light chain variable region comprises amino acids HQWSSNPLT (SEQ ID NO: 6), CDR1 of the heavy chain variable region comprises amino acids SYNMH (SEQ ID NO: 8), and CDR2 of the light chain variable region comprises amino acids AIYPGNGDTSYNQKFKG (SEQ ID NO: 9); and (c) wherein the CDR3 of the heavy chain variable region does not comprise VVYYSNSYWYFDV (SEQ ID NO: 13), when the CDR1 of the light chain variable region comprises amino acids RASSSVSYMH (SEQ ID NO: 3), CDR2 of the light chain variable region comprises amino acids ATSNLAS (SEQ ID NO: 4), CDR3 of the light chain variable region comprises amino acids QQSFSNPPT (SEQ ID NO: 7), CDR1 of the heavy chain variable region comprises amino acids SYNMH (SEQ ID NO: 8), and CDR2 of the light chain variable region comprises amino acids AIYPGNGDTSYNQKFKG (SEQ ID NO: 9).

More preferably the chimeric anti-CD20 MAb or fragment thereof comprising the complementarity-determining regions (CDRs) of a murine anti-CD20 MAb and the framework (FR) regions of the light and heavy chain variable regions of the murine anti-CD20 MAb and further, the light and heavy chain constant regions of a human antibody, wherein the chimeric anti-CD20 MAb or fragment thereof retains substantially the B-cell, and B-cell lymphoma and leukemia cell targeting of the murine anti-CD20 MAb, wherein the CDRs of the light chain variable region of the chimeric anti-CD20 MAb comprises the CDRs shown in FIGS. 4B and 4A, respectively, designated cA20Vk and cA20VH. Most preferably, the chimeric anti-CD20 MAb or fragment thereof comprises the light and heavy chain variable regions of murine anti-CD20 MAb shown in FIGS. 4B and 4A, respectively, designated cA20Vk and cA20 VH.

The present invention also encompasses a human anti-CD20 MAb or fragment thereof comprising the light and heavy chain variable, wherein said human CD20 MAb retains substantially the B-cell, and B-cell lymphoma and leukemia cell targeting and cell binding characteristics of a murine anti-CD20 MAb, wherein the CDRs of the light chain variable region of the human anti-CD20 MAb comprises the same CDRs as set forth above for the chimeric and humanized anti-CD20 mAbs and as shown in FIGS. 4A and 4B. This human anti-CD20 MAb or fragment thereof further comprises light and heavy chain constant regions of at least one human antibody.

The present invention is also intended to encompass antibody fusion proteins or fragments thereof comprising at least two anti-CD20 mabs or fragments thereof, as described above. The antibody fusion protein or fragment thereof of the present invention is also intended to encompass an antibody fusion protein or fragment thereof comprising at least one first anti-CD20 MAb or fragment thereof as described above and at least one second MAb or fragment thereof, other than the antiCD20 MAb or fragment described above. More preferably this second MAb is a MAb reactive with CD4, CD5, CD8, CD14, CD15, CD19, CD21, CD22, CD23, CD25, CD33, CD37, CD38, CD40, CD40L, CD46, CD52, CD54, CD74, CD80, CD126, B7, MUC1, MUC2, MUC3, MUC4, Ia, HM1.24, HLA-DR, tenascin, VEGF, PlGF, an oncogene, oncogene product, or a combination thereof, and even an anti-CD20 MAb that is different than the anti-CD20 MAb described herein. The antibody fusion proteins of the present invention may be composed of one CD20 MAb and one or more of the second mAbs to provide specificity to different antigens, and are described in more detail below.

The humanized, chimeric and human anti-CD20 antibody may possess enhanced affinity binding with the epitope, as well as antitumor and anti-B-cell activity, as a result of CDR mutation and manipulation of the CDR and other sequences in the variable region to obtain a superior therapeutic agent for the treatment of B-cell disorders, including B-cell lymphomas and leukemias and autoimmune diseases. Modification to the binding specificity, affinity or avidity of an antibody is known and described in WO 98/44001, as affinity maturation, and this application summarizes methods of modification and is incorporated in its entirety by reference.

It may also be desirable to modify the antibodies of the present invention to improve effector function, e.g., so as to enhance antigen-dependent cell-mediated cytotoxicity (ADCC) and/or complement dependent cytotoxicity (CDC)

of the antagonist. One or more amino acid substitutions or the introduction of cysteine in the Fc region may be made, thereby improving internalization capability and/or increased complement-mediated cell killing and ADCC. See Caron et al, *J. Ex. Med*. 176:1191–1195 (1991) and Shopes, B.J. *Immunol*. 148:2918–2022 (1992), incorporated herein by reference in their entirety. An antibody fusion protein may be prepared that has dual Fc regions with both enhanced complement lysis and ADCC capabilities.

The present invention is also directed to DNA sequences comprising a nucleic acid encoding a MAb or fragment thereof selected from the group consisting (a) an anti-CD20 MAb or fragment thereof as described herein, (b) an antibody fusion protein or fragment thereof comprising at least two of the anti-CD20 mAbs or fragments thereof, (c) an antibody fusion protein or fragment thereof comprising at least one first MAb or fragment thereof comprising the anti-CD20 MAb or fragment thereof as described herein and at least one second MAb or fragment thereof, other than the antiCD20 MAb or fragment thereof, and (d) an antibody fusion protein or fragment thereof comprising at least one first MAb or fragment thereof comprising the anti-CD20 MAb or fragment thereof and at least one second MAb or fragment thereof, wherein the second MAb is a MAb reactive with CD4, CD5, CD8, CD14, CD15, CD19, CD21, CD22, CD23, CD25, CD33, CD37, CD38, CD40, CD40L, CD46, CD52, CD54, CD74, CD80, CD126, B7, MUC1, MUC2, MUC3, MUC4, Ia, HM1.24, HLA-DR, tenascin, VEGF, PlGF, an oncogene, oncogene product, or a combination thereof.

Also encompassed by the present invention are expression vectors comprising the DNA sequences. These vectors contain the light and heavy chain constant regions and the hinge region of the human immunoglobulin, in the case of vectors for use in preparing the humanized, chimeric and human anti-CD20 mAbs or antibody fusion proteins thereof or fragments thereof. These vectors additionally contain, where required, promoters that express the mAbs in the selected host cell, immunoglobulin enhances and signal or leader sequences. Vectors that are particularly useful in the present invention are pdHL2 or GS, particularly when used to express a chimeric, humanized or human antibodies, such as gigs, where the vector codes for the heavy and light chain constant regions and hinge region of IgG1. More preferably, the light and heavy chain constant regions and hinge region are from a human EU myeloma immunoglobulin, where optionally at least one of the amino acid in the allotype positions is changed to that found in a different IgG1 allotype, and wherein optionally amino acid 253 of the heavy chain of EU based on the EU number system may be replaced with alanine. See Edelman et al, *Proc. Natl. Acad. Sci USA* 63: 78–85 (1969), incorporated herein in its entirety by reference.

Host cells containing the DNA sequences encoding the anti-CD20 mabs or fragments thereof or antibody fusion proteins or fragments thereof of the present invention or host cells containing the vectors that contain these DNA sequences are encompassed by the present invention. Particularly useful host cells are mammalian cells, more specifically lymphocytic cells, such as myeloma cells, discussed in more detail below.

Also encompassed by the present invention is the method of expressing the anti-CD20 MAb or fragment thereof or antibody fusion protein or fragment thereof comprising: (a) transfecting a mammalian cell with a DNA sequence of encoding the anti-CD20 mabs or fragments thereof or antibody fusion proteins or fragments thereof, and (b) culturing the cell transfected with the DNA sequence that secretes the anti-CD20 or fragment thereof or antibody fusion protein or fragment thereof. Known techniques may be used that include a selection marker on the vector so that host cells that express the mAbs and the marker can be easily selected.

The present invention particularly encompasses B-lymphoma cell and leukemia cell targeting diagnostic or therapeutic conjugates comprising an antibody component comprising an anti-CD20 MAb or fragment thereof or an antibody fusion protein or fragment thereof of the present invention that binds to the B-lymphoma or leukemia cell, that is bound to at least one diagnostic or at least one therapeutic agent.

The diagnostic conjugate comprises the antibody component comprising an anti-CD20 MAb or fragment thereof or an antibody fusion protein or fragment thereof, wherein the diagnostic agent comprises at least one photoactive diagnostic agent, and more preferably wherein the label is a radioactive label with an energy between 60 and 4,000 keV or a non-radioactive label. The radioactive label is preferably a gamma-, beta-, and positron-emitting isotope and is selected from the group consisting of $^{125}$I, $^{131}$I, $^{123}$I, $^{124}$I, $^{86}$Y, $^{186}$Re, $^{188}$Re, $^{62}$Cu, $^{64}$Cu, $^{111}$In, $^{67}$Ga, $^{68}$Ga, $^{99m}$Tc, $^{94m}$Tc, $^{18}$F, $^{11}$C, $^{13}$N, $^{15}$O, $^{76}$Br and combinations thereof.

The diagnostic conjugate of the present invention also utilizes a diagnostic agent, such as a contrast agent, for example, such as manganese, iron or gadolinium.

The therapeutic conjugate of the present invention comprises an antibody component comprising an antibody fusion protein or fragment thereof, wherein each of said mAbs or fragments thereof are bound to at least one therapeutic agent. The therapeutic conjugate of preferably is selected from the group consisting of a radioactive label, an immunomodulator, a hormone, a photoactive therapeutic agent, a cytotoxic agent, which may be a drug or a toxin, and a combination thereof. The drugs useful in the present invention are those drugs that possess the pharmaceutical property selected from the group consisting of antimitotic, antikinase, alkylating, antimetabolite, antibiotic, alkaloid, antiangiogenic, apoptotic agents and combinations thereof. More specifically, these drugs are selected from the group consisting of nitrogen mustards, ethylenimine derivatives, alkyl sulfonates, nitrosoureas, triazenes, folic acid analogs, COX-2 inhibitors, pyrimidine analogs, purine analogs, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, anthracyclines, taxanes, and their analogs, and a combination thereof. The toxins encompassed by the present invention are selected from the group consisting of ricin, abrin, alpha toxin, saporin, ribonuclease (RNase), e.g., onconase, DNase I, *Staphylococcal* enterotoxin-A, pokeweed antiviral protein, gelonin, diphtherin toxin, *Pseudomonas* exotoxin, and *Pseudomonas* endotoxin.

Useful therapeutic conjugates of the present invention are immunomodulators selected from the group consisting of a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF)), interferon, such as interferons-α, -β or -γ, and stem cell growth factor, such as designated "S1 factor". More specifically, immunomodulator, such as IL-1, IL-2, IL-3, IL-6, IL-10, IL-12, IL-18, IL-21 interferon-γ, TNF-α or a combination thereof are useful in the present invention.

Particularly useful therapeutic conjugates comprise one or more radioactive labels that have an energy between 60 and 700 keV. Such radioactive labels are selected from the group consisting of $^{225}$Ac, $^{67}$Ga, $^{90}$Y, $^{111}$In, $^{131}$I, $^{125}$I, $^{186}$Re, $^{188}$Re, $^{177}$Lu, $^{32}$P, $^{64}$Cu, $^{67}$Cu, $^{212}$Bi, $^{213}$Bi, $^{211}$At and combinations thereof. Other useful therapeutic conjugates are photoactive therapeutic agent, such as a chromogen or dye.

Other useful therapeutic conjugates comprise oligonucleotides, especially antisense oligonucleotides that preferably are directed against oncogenes and oncogene products of B-cell malignancies, such as bcl-2.

The present invention particularly encompasses methods of treating a B-cell lymphoma or leukemia cell disease or an autoimmune disease in a subject, such as a mammal, including humans, domestic or companion pets, such as dogs and cats, comprising administering to the subject a therapeutically effective amount of an anti-CD20 MAb or a fragment thereof of the present invention, formulated in a pharmaceutically acceptable vehicle. This therapy utilizes a "naked antibody" that does not have a therapeutic agent bound to it. The administration of the "naked anti-CD20 antibody" can be supplemented by administering to the subject concurrently or sequentially a therapeutically effective amount of another "naked antibody" that binds to or is reactive with another antigen on the surface of the target cell or that has other functions, such as effector functions in the Fc portion of the MAb, that is therapeutic and which is discussed herein. Preferred additional mAbs are at least one humanized, chimeric, human or murine (in the case of non-human animals) MAb selected from the group consisting of a MAb reactive with CD4, CD5, CD8, CD14, CD15, CD19, CD20, CD21, CD22, CD23, CD25, CD33, CD37, CD38, CD40, CD40L, CD46, CD52, CD54, CD74, CD80, CD126, B7, MUC1, Ia, HM1.24, and HLA-DR, tenascin, VEGF, PlGF, an oncogene, oncogene product, or a combination thereof, formulated in a pharmaceutically acceptable vehicle.

Both the naked anti-CD20 therapy alone or in combination with other naked mAbs as discussed above can be further supplemented with the administration, either concurrently or sequentially, of a therapeutically effective amount of at least one therapeutic agent, formulated in a pharmaceutically acceptable vehicle. As discussed herein the therapeutic agent may comprises a cytotoxic agent, a radioactive label, an oligonucleotide, an immunomodulator, a hormone, an enzyme, an oligonucleotide, a photoactive therapeutic agent or a combination thereof, formulated in a pharmaceutically acceptable vehicle.

In another therapeutic method, both the naked anti-CD20 therapy alone or in combination with other naked mAbs, as discussed above, can be further supplemented with the administration, either concurrently or sequentially, of a therapeutically effective amount of at least one therapeutic conjugate, described herein and formulated in a pharmaceutically acceptable vehicle. The antibody component of the therapeutic conjugate comprises at least one humanized, chimeric, human or murine (for non-human subjects) MAb selected from the group consisting of a MAb reactive with CD4, CD5, CD8, CD14, CD15, CD19, CD20, CD21, CD22, CD23, CD25, CD33, CD37, CD38, CD40, CD40L, CD46, CD52, CD54, CD74, CD80, CD126, B7, MUC1, MUC2, MUC3, MUC4, Ia, HM1.24, and HLA-DR, tenascin, VEGF, PlGF, an oncogene, oncogene product, or a combination thereof, formulated in a pharmaceutically acceptable vehicle. As discussed herein the therapeutic agent may comprise a cytotoxic agent, a radioactive label, an immunomodulator, a hormone, a photoactive therapeutic agent or a combination thereof, formulated in a pharmaceutically acceptable vehicle.

As described herein the present invention particularly encompasses a method of treating a B-cell lymphoma or leukemia or an autoimmune disease in a subject comprising administering to a subject a therapeutically effective amount of an antibody fusion protein or fragment thereof comprising at least two anti-CD20 mAbs or fragments thereof of the present invention or comprising at least one anti-CD20 MAb or fragment thereof of the present invention and at least one additional MAb, preferably selected from the group consisting of mAbs reactive with CD4, CD5, CD8, CD14, CD15, CD19, CD20, CD21, CD22, CD23, CD25, CD33, CD37, CD38, CD40, CD40L, CD46, CD52, CD54, CD74, CD80, CD126, B7, MUC1, MUC2, MUC3, MUC4, Ia, HM1.24, and HLA-DR, tenascin, VEGF, PlGF, an oncogene, oncogene product, or a combination thereof, formulated in a pharmaceutically acceptable vehicle.

This therapeutic method can further be supplemented with the administration to the subject concurrently or sequentially of a therapeutically effective amount of at least one therapeutic agent, formulated in a pharmaceutically acceptable vehicle, wherein the therapeutic agent is preferably a cytotoxic agent, a radioactive label, an immunomodulator, a hormone, a photoactive therapeutic agent or a combination thereof, formulated in a pharmaceutically acceptable vehicle.

Further, the antibody fusion proteins can be administered to a subject concurrently or sequentially a therapeutically effective amount of a therapeutic conjugate comprising at least one MAb bound to at least one therapeutic agent, wherein said MAb component of the conjugate preferably comprises at least one humanized, chimeric, human or murine (for non-human subjects) MAb selected from the group consisting of a MAb reactive with CD4, CD5, CD8, CD14, CD15, CD19, CD20, CD21, CD22, CD23, CD25, CD33, CD37, CD38, CD40, CD40L, CD46, CD52, CD54, CD74, CD80, CD126, B7, MUC1, MUC2, MUC3, MUC4, Ia, HM1.24, and HLA-DR, tenascin, VEGF, PlGF, an oncogene, oncogene product, or a combination thereof, formulated in a pharmaceutically acceptable vehicle. The antibody fusion protein itself can be conjugated to a therapeutic agent and thus provides a vehicle to attach more than one therapeutic agent to an antibody component and these therapeutic agents can be a combination of different recited agents or combinations of the same agents, such as two different therapeutic radioactive labels. Also encompassed by the present invention is a method of diagnosing a B-cell lymphoma or leukemia in a subject comprising administering to the subject, such as a mammal, including humans and domestic and companion pets, such as dogs, cats, rabbits, guinea pigs, a diagnostic conjugate comprising an anti-CD20 MAb or fragment thereof or an antibody fusion protein or fragment thereof of the present invention that binds to the lymphoma or leukemia cell, wherein the anti-CD20 MAb or fragment thereof or antibody fusion protein or fragment thereof is bound to at least one diagnostic agent, formulated in a pharmaceutically acceptable vehicle. The useful diagnostic agents are described herein.

2. Definitions

In the description that follows, a number of terms are used and the following definitions are provided to facilitate understanding of the present invention.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as $F(ab')_2$, $F(ab)_2$, Fab', Fab, Fv, scFv and the like. Regardless of structure, an antibody fragment binds with the same antigen that is recognized by the intact antibody. For example, an anti-CD20 monoclonal antibody fragment binds with an epitope of CD20. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A naked antibody is generally an entire antibody which is not conjugated to a therapeutic agent. This is so because the Fc portion of the antibody molecule provides effector functions, such as complement fixation and ADCC (antibody dependent cell cytotoxicity), which set mechanisms into action that may result in cell lysis. However, it is possible that the Fc portion is not required for therapeutic function, with other mechanisms, such as apoptosis, coming into play. Naked antibodies include both polyclonal and monoclonal antibodies, as well as certain recombinant antibodies, such as chimeric, humanized or human antibodies.

A chimeric antibody is a recombinant protein that contains the variable domains including the complementarity determining regions (CDRs) of an antibody derived from one species, preferably a rodent antibody, while the constant domains of the antibody molecule is derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, is transferred from the heavy and light variable chains of the rodent antibody into human heavy and light variable domains. The constant domains of the antibody molecule is derived from those of a human antibody.

A human antibody is an antibody obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552–553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564–571 (1993).

Human antibodies may also be generated by in vitro activated B cells. See U.S. Pat. Nos. 5,567,610 and 5,229,275, which are incorporated in their entirety by reference.

A therapeutic agent is a molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, nucleases, hormones, immunomodulators, chelators, boron compounds, photoactive agents or dyes and radioisotopes.

A diagnostic agent is a molecule or atom which is administered conjugated to an antibody moiety, i.e., antibody or antibody fragment, or subfragment, and is useful in diagnosing a disease by locating the cells containing the antigen. Useful diagnostic agents include, but are not limited to, radioisotopes, dyes (such as with the biotin-streptavidin complex), contrast agents, fluorescent compounds or molecules and enhancing agents (e.g. paramagnetic ions) for magnetic resonance imaging (MRI). U.S. Pat. No. 6,331,175 describes MRI technique and the preparation of antibodies conjugated to a MRI enhancing agent and is incorporated in its entirety by reference. Preferably, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates are coupled to the peptide antigens using standard chemistries. The chelate is normally linked to the antibody by a group which enables formation of a bond to the molecule with minimal loss of immunoreactivity and minimal aggregation and/or internal cross-linking. other, more unusual, methods and reagents for conjugating chelates to antibodies are disclosed in U.S. Pat. No. 4,824,659 to Hawthorne, entitled "Antibody Conjugates", issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV, such as $^{125}I$, $^{131}I$, $^{123}I$, $^{124}I$, $^{62}Cu$, $^{64}Cu$, $^{18}F$, $^{111}In$, $^{67}Ga$, $^{68}Ga$, $^{99m}Tc$, $^{94m}Tc$, $^{11}C$, $^{13}N$, $^{15}O$, $^{76}Br$, for radio-imaging. The same chelates, when complexed with non-radioactive metals, such as manganese, iron and gadolinium are useful for MRI, when used along with the antibodies of the invention. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed by the invention.

An immunoconjugate is a conjugate of an antibody component with a therapeutic or diagnostic agent. The diagnostic agent can comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope.

An expression vector is a DNA molecules comprising a gene that is expressed in a host cell. Typically, gene expression is placed under the control of certain regulatory elements, including constitutive or inducible promoters, tissue-specific regulatory elements and enhancers. Such a gene is said to be "operably linked to" the regulatory elements.

A recombinant host may be any prokaryotic or eukaryotic cell that contains either a cloning vector or expression vector. This term also includes those prokaryofic or eukaryotic cells, as well as an transgenic animal, that have been genetically engineered to contain the cloned gene(s) in the chromosome or genome of the host cell or cells of the host cells. Suitable mammalian host cells include myeloma cells, such as SP2/0 cells, and NS0 cells, as well as Chinese Hamster Ovary (CHO) cells, hybridoma cell lines and other mammalian host cell useful for expressing antibodies. Also particularly useful to express mAbs and other fusion proteins, is a human cell line, PER.C6 disclosed in WO 0063403 A2, which produces 2 to 200-fold more recombinant protein as compared to conventional mammalian cell lines, such as CHO, COS, Vero, Hela, BHK and SP2-cell lines. Special transgenic animals with a modified immune system are particularly useful for making fully human antibodies.

As used herein, the term antibody fusion protein is a recombinantly produced antigen-binding molecule in which two or more of the same or different single-chain antibody or antibody fragment segments with the same or different specificities are linked. Valency of the fusion protein indicates how many binding arms or sites the fusion protein has to a single antigen or epitope; i.e., monovalent, bivalent, trivalent or mutlivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only binds with one epitope, for example a diabody with two binding site reactive with the same antigen. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

A multispecific antibody is an antibody that can bind simultaneously to at least two targets that are of different structure, e.g., two different antigens, two different epitopes on the same antigen, or a hapten and/or an antigen or epitope. One specificity would be for a B-cell, T-cell, myeloid-, plasma-, and mast-cell antigen or epitope. Another specificity could be to a different antigen on the same cell type, such as CD20, CD19, CD21, CD23, CD46, CD80, HLA-DR, CD74, MuC1, and CD22 on B-cells. Multispecific, multivalent antibodies are constructs that have more than one binding site, and the binding sites are of different specificity. For example, a diabody, where one binding site reacts with one antigen and the other with the other antigen.

A bispecific antibody is an antibody that can bind simultaneously to two targets which are of different structure. Bispecific antibodies (bsAb) and bispecific antibody fragments (bsFab) have at least one arm that specifically binds to, for example, a B-cell, T-cell, myeloid-, plasma-, and mast-cell antigen or epitope and at least one other arm that specifically binds to a targetable conjugate that bears a therapeutic or diagnostic agent. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with a binding site for one antigen and two scFv with two binding sites for a second antigen.

Caninized or felinized antibodies are recombinant proteins in which rodent (or another species) complementarity determining regions of a monoclonal antibody have been transferred from heavy and light variable chains of rodent (or another species) immunoglobulin into a dog or cat, respectively, immunoglobulin variable domain.

Domestic animals include large animals such as horses, cattle, sheep, goats, llamas, alpacas, and pigs, as well as companion animals. In a preferred embodiment, the domestic animal is a horse.

Companion animals include animals kept as pets. These are primarily dogs and cats, although small rodents, such as guinea pigs, hamsters, rats, and ferrets, are also included, as are subhuman primates such as monkeys. In a preferred embodiment the companion animal is a dog or a cat.

3. Preparation of Monoclonal Antibodies Including Chimeric, Humanized and Human Antibodies Monoclonal antibodies (MAbs) are a homogeneous population of antibodies to a particular antigen and the antibody comprises only one type of antigen binding site and binds to only one epitope on an antigenic determinant. Rodent monoclonal antibodies to specific antigens may be obtained by methods known to those skilled in the art. See, for example, Kohler and Milstein, *Nature* 256: 495 (1975), and Coligan et al. (eds.), CURRENT PROTOCOLS IN IMMUNOLOGY, VOL. 1, pages 2.5.1–2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1–2.7.12 and pages 2.9.1–2.9.3. Also, see Baines et al, "Purification of Immunoglobulin G (IgG)," in METHODS IN MOLECULAR BIOLOGY, VOL. 10, pages 79–104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions.

General techniques for cloning murine immunoglobulin variable domains are described, for example, by the publication of Orlandi et al., *Proc. Nat'l Acad. Sci. USA* 86: 3833 (1989), which is incorporated by reference in its entirety. Techniques for constructing chimeric antibodies are well known to those of skill in the art. As an example, Leung et al., *Hybridoma* 13:469 (1994), describe how they produced an LL2 chimera by combining DNA sequences encoding the $V_\kappa$ and $V_H$ domains of LL2 monoclonal antibody, an anti-CD22 antibody, with respective human κ and $IgG_1$ constant region domains. This publication also provides the nucleotide sequences of the LL2 light and heavy chain variable regions, $V_\kappa$ and $V_H$, respectively. Techniques for producing humanized MAbs are described, for example, by Jones et al., *Nature* 321: 522 (1986), Riechmann et al., *Nature* 332: 323 (1988), Verhoeyen et al, *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al, *J. Immun.* 150: 2844 (1993), each of which is hereby incorporated by reference.

A chimeric antibody is a recombinant protein that contains the variable domains including the CDRs derived from one species of animal, such as a rodent antibody, while the remainder of the antibody molecule; i.e., the constant domains, is derived from a human antibody. Accordingly, a chimeric monoclonal antibody can also be humanized by replacing the sequences of the murine FR in the variable domains of the chimeric MAb with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Further, the affinity of humanized, chimeric and human MAbs to a specific epitope can be increased by mutagenesis of the CDRs, so that a lower dose of antibody may be as effective as a higher dose of a lower affinity MAb prior to mutagenesis. See for example, WO0029584A1

Another method for producing the antibodies of the present invention is by production in the milk of transgenic livestock. See, e.g., Colman, A., *Biochem. Soc. Symp.*, 63: 141–147, 1998; U.S. Pat. No. 5,827,690, both of which are incorporated in their entirety by reference. Two DNA constructs are prepared which contain, respectively, DNA segments encoding paired immunoglobulin heavy and light chains. The DNA segments are cloned into expression vectors which contain a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are co-injected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

A fully human antibody of the present invention, i.e., human anti-CD20 MAbs or other human antibodies, such as anti-CD22, anti-CD19, anti-CD23, or anti-CD21 MAbs for combination therapy with humanized, chimeric or human anti-CD20 antibodies, can be obtained from a transgenic non-human animal. See, e.g., Mendez et al., *Nature Genetics*, 15: 146–156 (1997); U.S. Pat. No. 5,633,425, which are incorporated in their entirety by reference. For example, a human antibody can be recovered from a transgenic mouse possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Further recent methods for producing bispecific mAbs include engineered recombinant mAbs which have additional cysteine residues so that they crosslink more strongly than the more common immunoglobulin isotypes. See, e.g., FitzGerald et al, Protein Eng. 10(10): 1221–1225, 1997. Another approach is to engineer recombinant fusion proteins linking two or more different single-chain antibody or antibody fragment segments with the needed dual specificities. See, e.g., Coloma et al., *Nature Biotech*. 15:159–163, 1997. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with two binding sites for one antigen and two scFv with two binding sites for a second antigen.

Bispecific fusion proteins linking two or more different single-chain antibodies or antibody fragments are produced in similar manner. Recombinant methods can be used to produce a variety of fusion proteins. For example a fusion protein comprising a Fab fragment derived from a humanized monoclonal anti-CD20 antibody and a scFv derived from a murine anti-diDTPA can be produced. A flexible linker, such as GGGS (SEQ ID NO: 55) connects the scFv to the constant region of the heavy chain of the anti-CD20 antibody. Alternatively, the scFv can be connected to the constant region of the light chain of another humanized antibody. Appropriate linker sequences necessary for the in-frame connection of the heavy chain Ed to the scFv are introduced into the VL and VK domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the VH region of an anti-CD20 antibody. The resulting vector can be used to transfect an appropriate host cell, such as a mammalian cell for the expression of the bispecific fusion protein.

4. Production of Antibody Fragments

Antibody fragments which recognize specific epitopes can be generated by known techniques. The antibody fragments are antigen binding portions of an antibody, such as F(ab')$_2$, Fab', Fab, Fv, sFv and the like. Other antibody fragments include, but are not limited to: the F(ab)'$_2$ fragments which can be produced by pepsin digestion of the antibody molecule and the Fab' fragments, which can be generated by reducing disulfide bridges of the F(ab)'$_2$ fragments. Alternatively, Fab' expression libraries can be constructed (Huse et al., 1989, *Science*, 246:1274–1281) to allow rapid and easy identification of monoclonal Fab' fragments with the desired specificity. The present invention encompasses antibodies and antibody fragments.

A single chain Fv molecule (scFv) comprises a VL domain and a VH domain. The VL and VH domains associate to form a target binding site. These two domains are further covalently linked by a peptide linker (L). A scFv molecule is denoted as either VL-L-VH if the VL domain is the N-terminal part of the scFv molecule, or as VH-L-VL if the VH domain is the N-terminal part of the scFv molecule. Methods for making scFv molecules and designing suitable peptide linkers are described in U.S. Pat. Nos. 4,704,692, 4,946,778, R. Raag and M. Whitlow, "*Single Chain Fvs*." FASEB Vol 9:73–80 (1995) and R. E. Bird and B. W. Walker, "*Single Chain Antibody Variable Regions*," TIBTECH, Vol 9: 132–137 (1991). These references are incorporated herein by reference.

An antibody fragment can be prepared by proteolytic hydrolysis of the full length antibody or by expression in *E. coli* or another host of the DNA coding for the fragment. An antibody fragment can be obtained by pepsin or papain digestion of full length antibodies by conventional methods. For example, an antibody fragment can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using papain produces two monovalent Fab fragments and an Fc fragment directly. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys*. 89: 230 (1960); Porter, *Biochem. J*. 73: 119 (1959), Edelman et al., in METHODS IN ENZYMOLOGY VOL. 1, page 422 (Academic Press 1967), and Coligan at pages 2.8.1–2.8.10 and 2.10.–2.10.4.

Another form of an antibody fragment is a peptide coding for a single complementarity-determining region (CDR). A CDR is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. See, for example, Larrick et al, *Methods: A Companion to Methods in Enzymology* 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166–179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137–185 (Wiley-Liss, Inc. 1995).

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

5. Multispecific and Multivalent Antibodies

The anti-CD20 antibodies, as well as other antibodies with different specificities for use in combination therapy, described herein, can also be made as multispecific antibodies (comprising at least one binding site to a CD20 epitope or antigen and at least one binding site to another epitope on CD20 or another antigen) and multivalent antibodies (comprising multiple binding sites to the same epitope or antigen). Multivalent target binding proteins are described in U.S. Ser. No. 09/911,610 (Leung et al.), which is incorporated herein by reference in its entirety.

The present invention provides a bispecific antibody or antibody fragment having at least a binding region that specifically binds a targeted cell marker and at least one other binding region that specifically binds a targetable conjugate. The targetable conjugate comprises a carrier portion which comprises or bears at least one epitope recognized by at least one binding region of the bispecific antibody or antibody fragment.

A variety of recombinant methods can be used to produce bispecific antibodies and antibody fragments as described above.

An anti-CD20 multivalent antibody is also contemplated in the present invention. This multivalent target binding protein is constructed by association of a first and a second polypeptide. The first polypeptide comprises a first single chain Fv molecule covalently linked to a first immunoglobulin-like domain which preferably is an immunoglobulin light chain variable region domain. The second polypeptide comprises a second single chain Fv molecule covalently linked to a second immunoglobulin-like domain which preferably is an immunoglobulin heavy chain variable region domain. Each of the first and second single chain Fv molecules forms a target binding site, and the first and second immunoglobulin-like domains associate to form a third target binding site.

A single chain Fv molecule with the VL-L-VH configuration, wherein L is a linker, may associate with another single chain Fv molecule with the VH-L-VL configuration to form a bivalent dimer. In this case, the VL domain of the first scFv and the VH domain of the second scFv molecule associate to form one target binding site, while the VH domain of the first scFv and the VL domain of the second scFv associate to form the other target binding site.

Another embodiment of the present invention is a CD20 bispecific, trivalent targeting protein comprising two heterologous polypeptide chains associated non-covalently to form three binding sites, two of which have affinity for one target and a third which has affinity for a hapten that can be made and attached to a carrier for a diagnostic and/or therapeutic agent. Preferably, the binding protein has two CD20 binding sites and one CD22 binding site. The bispecific, trivalent targeting agents have two different scFvs, one scFv contains two $V_H$ domains from one antibody connected by a short linker to the $V_L$ domain of another antibody and the second scFv contains two $V_L$ domains from the first antibody connected by a short linker to the $V_H$ domain of the other antibody. The methods for generating multivalent, multispecific agents from $V_H$ and $V_L$ domains provide that individual chains synthesized from a DNA plasmid in a host organism are composed entirely of $V_H$ domains (the $V_H$-chain) or entirely of $V_L$ domains (the $V_L$-chain) in such a way that any agent of multivalency and multispecificity can be produced by non-covalent association of one $V_H$-chain with one $V_L$-chain. For example, forming a trivalent, trispecific agent, the $V_H$-chain will consist of the amino acid sequences of three $V_H$ domains, each from an antibody of different specificity, joined by peptide linkers of variable lengths, and the $V_L$-chain will consist of complementary $V_L$ domains, joined by peptide linkers similar to those used for the $V_H$-chain. Since the $V_H$ and $V_l$ domains of antibodies associate in an anti-parallel fashion, the preferred method in this invention has the $V_L$ domains in the $V_L$-chain arranged in the reverse order of the $V_H$ domains in the $V_H$-chain.

6. Diabodies, Triabodies and Tetrabodies

The anti-CD20 antibodies of the present invention can also be used to prepare functional bispecific single-chain antibodies (bscAb), also called diabodies, and can be produced in mammalian cells using recombinant methods. See, e.g., Mack et al., *Proc. Natl. Acad. Sci.*, 92: 7021–7025, 1995, incorporated. For example, bscAb are produced by joining two single-chain Fv fragments via a glycine-serine linker using recombinant methods. The V light-chain ($V_L$) and V heavy-chain ($V_H$) domains of two antibodies of interest are isolated using standard PCR methods. The $V_L$ and $V_H$ cDNA's obtained from each hybridoma are then joined to form a single-chain fragment in a two-step fusion PCR. The first PCR step introduces the $(Gly_4-Ser_1)_3$ linker, and the second step joins the $V_L$ and $V_H$ amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into an eukaryotic expression vector. Functional protein expression can be obtained by transfecting the vector into chinese hamster ovary cells. Bispecific fusion proteins are prepared in a similar manner. Bispecific single-chain antibodies and bispecific fusion proteins are included within the scope of the present invention.

For example, a humanized, chimeric or human anti-CD20 monoclonal antibody can be used to produce antigen specific diabodies, triabodies, and tetrabodies. The monospecific diabodies, triabodies, and tetrabodies bind selectively to targeted antigens and as the number of binding sites on the molecule increases, the affinity for the target cell increases and a longer residence time is observed at the desired location. For diabodies, the two chains comprising the $V_H$ polypeptide of the humanized CD20 MAb connected to the $V_\kappa$ polypeptide of the humanized CD20 MAb by a five amino acid residue linker are utilized. Each chain forms one half of the humanized CD20 diabody. In the case of triabodies, the three chains comprising $V_H$ polypeptide of the humanized CD20 MAb connected to the $V_\kappa$ polypeptide of the humanized CD20 MAb by no linker are utilized. Each chain forms one third of the hCD20 triabody.

The ultimate use of the bispecific diabodies described herein is for pre-targeting CD20 positive tumors for subsequent specific delivery of diagnostic or therapeutic agents. These diabodies bind selectively to targeted antigens allowing for increased affinity and a longer residence time at the desired location. Moreover, non-antigen bound diabodies are cleared from the body quickly and exposure of normal tissues is minimized. Bispecific antibody point mutations for enhancing the rate of clearance can be found in U.S. Provisional Application No. 60/361,037 to Qu et al., which is incorporated herein by reference in its entirety. Bispecific diabodies for affinity enhancement are disclosed in U.S. application Ser. Nos. 10/270,071 (Rossi et al.), 10/270,073 (Rossi et al.) and 10/328,190 (Rossi et al.), which are incorporated herein by reference in their entirety. The diagnostic and therapeutic agents can include isotopes, drugs, toxins, cytokines, hormones, growth factors, conjugates, radionuclides, and metals. For example, gadolinium metal is used for magnetic resonance imaging (MRI). Examples of radionuclides are $^{225}Ac$, $^{18}F$, $^{68}Ga$, $^{67}Ga$, $^{90}Y$, $^{86}Y$, $^{111}In$, $^{131}I$, $^{125}I$, $^{123}I$, $^{99m}Tc$, $^{94m}Tc$, $^{186}Re$, $^{188}Re$, $^{177}Lu$, $^{62}Cu$, $^{64}Cu$, $^{67}Cu$, $^{212}Bi$, $^{213}Bi$, $^{32}P$, $^{11}C$, $^{13}N$, $^{15}O$, $^{76}Br$, and $^{211}At$. Other radionuclides are also available as diagnostic and therapeutic agents, especially those in the energy range of 60 to 4,000 keV.

More recently, a tetravalent tandem diabody (termed tandab) with dual specificity has also been reported (Cochlovius et al., Cancer Research (2000) 60: 4336–4341). The bispecific tandab is a dimer of two identical polypeptides, each containing four variable domains of two different antibodies ($V_{H1}$, $V_{L1}$, $V_{H2}$, $V_{L2}$) linked in an orientation to facilitate the formation of two potential binding sites for each of the two different specificities upon self-association.

7. Conjugated Multivalent and Multispecific Anti-CD20 Antibodies

In another embodiment of the instant invention is a conjugated multivalent anti-CD20 antibody. Additional amino acid residues may be added to either the N- or C-terminus of the first or the second polypeptide. The additional amino acid residues may comprise a peptide tag, a signal peptide, a cytokine, an enzyme (for example, a pro-drug activating enzyme), a hormone, a peptide toxin, such as pseudomonas extoxin, a peptide drug, a cytotoxic protein or other functional proteins. As used herein, a functional protein is a protein which has a biological function.

In one embodiment, drugs, toxins, radioactive compounds, enzymes, hormones, cytotoxic proteins, chelates, cytokines and other functional agents may be conjugated to the multivalent target binding protein, preferably through covalent attachments to the side chains of the amino acid residues of the multivalent target binding protein, for example amine, carboxyl, phenyl, thiol or hydroxyl groups. Various conventional linkers may be used for this purpose, for example, diisocyanates, diisothiocyanates, bis(hydroxysuccinimide) esters, carbodiimides, maleimide-hydroxysuccinimide esters, glutaraldehyde and the like. Conjugation of agents to the multivalent protein preferably does not significantly affect the protein's binding specificity or affinity to its target. As used herein, a functional agent is an agent which has a biological function. A preferred functional agent is a cytotoxic agent.

In still other embodiments, bispecific antibody-directed delivery of therapeutics or prodrug polymers to in vivo targets can be combined with bispecific antibody delivery of radionuclides, such that combination chemotherapy and radioimmunotherapy is achieved. Each therapy can be conjugated to the targetable conjugate and administered simultaneously, or the nuclide can be given as part of a first targetable conjugate and the drug given in a later step as part of a second targetable conjugate.

In another embodiment, cytotoxic agents may be conjugated to a polymeric carrier, and the polymeric carrier may subsequently be conjugated to the multivalent target binding protein. For this method, see Ryser et al., *Proc. Natl. Acad. Sci. USA*, 75:3867–3870, 1978, U.S. Pat. Nos. 4,699,784 and 4,046,722, which are incorporated herein by reference. Conjugation preferably does not significantly affect the binding specificity or affinity of the multivalent binding protein.

8. Humanized, Chimeric and Human Antibodies Use for Treatment and Diagnosis

Humanized, chimeric and human monoclonal antibodies, i.e., anti-CD20 MAbs and other MAbs described herein, in accordance with this invention are suitable for use in therapeutic methods and diagnostic methods. Accordingly, the present invention contemplates the administration of the humanized, chimeric and human antibodies of the present invention alone as a naked antibody or administered as a multimodal therapy, temporally according to a dosing regimen, but not conjugated to, a therapeutic agent. The efficacy of the naked anti-CD20 MAbs can be enhanced by supplementing naked antibodies with one or more other naked antibodies, i.e., MAbs to specific antigens, such as CD4, CD5, CD8, CD14, CD15, CD19, CD21, CD22, CD23, CD25, CD33, CD37, CD38, CD40, CD40L, CD46, CD52, CD54, CD74, CD80, CD126, B7, MUC1, Ia, HM1.24, or HLA-DR, tenascin, VEGF, PIGF, an oncogene, an oncogene product, or a combination thereof with one or more immunoconjugates of anti-CD20, or antibodies to theses recited antigens, conjugated with therapeutic agents, including drugs, toxins, immunomodulators, hormones, therapeutic radionuclides, etc., with one or more therapeutic agents, including drugs, oligonucleotide, toxins, immunomodulators, hormones, therapeutic radionuclides, etc., administered concurrently or sequentially or according to a prescribed dosing regimen, with the MAbs. Preferred B-cell antigens include those equivalent to human CD19, CD20, CD21, CD22, CD23, CD46, CD52, CD74, CD80, and CD5 antigens. Preferred T-cell antigens include those equivalent to human CD4, CD8 and CD25 (the IL-2 receptor) antigens. An equivalent to HLA-DR antigen can be used in treatment of both B-cell and T-cell disorders. Particularly preferred B-cell antigens are those equivalent to human CD19, CD22, CD21, CD23, CD74, CD80, and HLA-DR antigens. Particularly preferred T-cell antigens are those equivalent to human CD4, CD8 and CD25 antigens. CD46 is an antigen on the surface of cancer cells that block complement-dependent lysis (CDC).

Further, the present invention contemplates the administration of an immunoconjugate for diagnostic and therapeutic uses in B cell lymphomas and other disease or disorders. An immunoconjugate, as described herein, is a molecule comprising an antibody component and a therapeutic or diagnostic agent, including a peptide which may bear the diagnostic or therapeutic agent. An immunoconjugate retains the immunoreactivity of the antibody component, i.e., the antibody moiety has about the same or slightly reduced ability to bind the cognate antigen after conjugation as before conjugation.

A wide variety of diagnostic and therapeutic agents can be advantageously conjugated to the antibodies of the invention. The therapeutic agents recited here are those agents that also are useful for administration separately with the naked antibody as described above. Therapeutic agents include, for example, chemotherapeutic drugs such as vinca alkaloids, anthracyclines, epidophyllotoxin, taxanes, antimetabolites, alkylating agents, antikinase agents, antibiotics, Cox-2 inhibitors, antimitotics, antiangiogenic and apoptotoic agents, particularly doxorubicin, methotrexate, taxol, CPT-11, camptothecans, and others from these and other classes of anticancer agents, and the like. Other useful cancer chemotherapeutic drugs for the preparation of immunoconjugates and antibody fusion proteins include nitrogen mustards, alkyl sulfonates, nitrosoureas, triazenes, folic acid analogs, COX-2 inhibitors, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Additionally, a chelator such as DTPA (such as Mx-DTPA), DOTA, TETA, or NOTA or a suitable peptide, to which a detectable label, such as a fluorescent molecule, or cytotoxic agent, such as a heavy metal or radionuclide, can be conjugated. For example, a diagnostically or therapeutically useful immunoconjugate can be obtained by conjugating a photoactive agent or dye to an antibody composite. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), PHOTODYNAMIC THERAPY OF TUMORS AND OTHER DISEASES (Libreria Progetto 1985); van den Bergh, *Chem. Britain* 22:430 (1986)). Moreover, monoclonal antibodies have been coupled with photoactivated dyes for achieving phototherapy. Mew et al., *J. Immunol.* 130:1473 (1983); idem., *Cancer Res.* 45:4380 (1985); Oseroff et al., *Proc. Natl Acad. Sci. USA* 83:8744 (1986); idem., *Photochem. Photobiol.* 46:83 (1987); Hasan et al., *Prog. Clin. Biol. Res.* 288:471 (1989); Tatsuta et al., *Lasers Surg. Med.* 9:422 (1989); Pelegrin et al., *Cancer* 67:2529 (1991). However, these earlier studies did not include use of endoscopic therapy applications, especially with the use of antibody fragments or subfragments. Thus, the present invention contemplates the therapeutic use of immunoconjugates comprising photoactive agents or dyes.

Also contemplated by the present invention are the use of radioactive and non-radioactive agents as diagnostic agents. A suitable non-radioactive diagnostic agent is a contrast agent suitable for magnetic resonance imaging, computed tomography or ultrasound. Magnetic imaging agents include, for example, non-radioactive metals, such as manganese, iron and gadolinium, complexed with metal-chelate combinations that include 2-benzyl-DTPA and its monomethyl and cyclohexyl analogs, when used along with the antibodies of the invention. See U.S. Ser. No. 09/921,290 filed on Oct. 10, 2001, which is incorporated in its entirety by reference.

Furthermore, a radiolabeled antibody or immunoconjugate may comprise a γ-emitting radioisotope or a positron-emitter useful for diagnostic imaging. Suitable radioisotopes, particularly in the energy range of 60 to 4,000keV, include $^{131}$I, $^{121}$I, $^{124}$I, $^{86}$Y, $^{62}$Cu, $^{64}$Cu, $^{111}$In, $^{67}$Ga, $^{68}$Ga, $^{99m}$Tc, $^{94m}$Tc, $^{18}$F, $^{11}$C, $^{13}$N, $^{15}$O, $^{75}$Br, and the like. See for example, U.S. Patent Application entitled "Labeling Targeting Agents with Gallium-68"—Inventors G. L. Griffiths and W. J. McBride, (U.S. Provisional Application No. 60/342, 104), which discloses positron emitters, such as $^{18}$F, $^{68}$Ga, $^{94m}$Tc. and the like, for imaging purposes and which is incorporated in its entirety by reference. Particularly useful therapeutic radionuclides include, but are not limited to, $^{32}$P, $^{33}$P, $^{47}$Sc, $^{64}$Cu, $^{67}$Cu, $^{67}$Ga, $^{90}$Y, $^{111}$Ag, $^{111}$In, $^{125}$I, $^{131}$I, $^{142}$Pr, $^{153}$Sm, $^{161}$Tb, $^{166}$Dy, $^{166}$Ho, $^{177}$Lu, $^{186}$Re, $^{188}$Re, $^{189}$Re, $^{212}$Pb, $^{212}$Bi, $^{213}$Bi, $^{211}$At, $^{223}$Ra and $^{225}$Ac. Particularly useful diagnostic/detection radionuclides include, but are not limited to, $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94m}$Tc, $^{99m}$Tc, $^{111}$In, $^{123}$I, $^{124}$I, $^{125}$I, $^{131}$I, $^{154-158}$Gd, $^{32}$P, $^{90}$Y, $^{188}$Re, and $^{175}$Lu.

A toxin, such as *Pseudomonas* exotoxin, may also be complexed to or form the therapeutic agent portion of an antibody fusion protein of an anti-CD20 antibody of the present invention. Other toxins suitably employed in the preparation of such conjugates or other fusion proteins, include ricin, abrin, ribonuclease (RNase), DNase I, *Staphylococcal* enterotoxin-A, pokeweed antiviral protein, gelonin, diphtherin toxin, *Pseudomonas* exotoxin, and *Pseudomonas* endotoxin. See, for example, Pastan et al., *Cell* 47:641 (1986), and Goldenberg, *CA—A Cancer Journal for Clinicians* 44:43 (1994). Additional toxins suitable for use in the present invention are known to those of skill in the art and are disclosed in U.S. Pat. No. 6,077,499, which is incorporated in its entirety by reference.

An immunomodulator, such as a cytokine may also be conjugated to, or form the therapeutic agent portion of an antibody fusion protein or be administered with the humanized anti-CD20 antibodies of the present invention. Suitable cytokines for the present invention include, but are not limited to, interferons and interleukins, as described below.

An oligonucleotide, such the antisense molecules inhibiting bcl-2 expression that are described in U.S. Pat. No. 5,734,033 (Reed) which is incorporated by reference in its entirety, may also be conjugated to, or form the therapeutic agent portion of an antibody fusion protein or be administered with the humanized anti-CD20 antibodies of the present invention.

9. Preparation of Immunoconjugates

Any of the antibodies or antibody fusion proteins of the present invention can be conjugated with one or more therapeutic or diagnostic agents. Generally, one therapeutic or diagnostic agent is attached to each antibody or antibody fragment but more than one therapeutic agent or diagnostic agent can be attached to the same antibody or antibody fragment. The antibody fusion proteins of the present invention comprise two or more antibodies or fragments thereof and each of the antibodies that composes this fusion protein can contain a therapeutic agent or diagnostic agent. Additionally, one or more of the antibodies of the antibody fusion protein can have more than one therapeutic of diagnostic agent attached. Further, the therapeutic agents do not need to be the same but can be different therapeutic agents. For example, one can attach a drug and a radioisotope to the same fusion protein. Particularly, an IgG can be radiolabeled with $^{131}$I and attached to a drug. The $^{131}$I, can be incorporated into the tyrosine of the IgG and the drug attached to the epsilon amino group of the IgG lysines. Both therapeutic and diagnostic agents also can be attached to reduced SH groups and to the carbohydrate side chains.

Radionuclides suitable for treating a disease tissue substantially decay by beta-particle emission and include, but are not limited to: $^{32}$P, $^{33}$P, $^{47}$Sc, $^{59}$Fe, $^{64}$Cu, $^{67}$Cu, $^{75}$Se, $^{77}$As, $^{89}$Sr, $^{90}$Y, $^{99}$Mo, $^{105}$Rh, $^{109}$Pd, $^{111}$Ag, $^{125}$I, $^{131}$I, $^{142}$Pr, $^{143}$Pr, $^{149}$Pm, $^{153}$Sm, $^{161}$Tb, $^{166}$Ho, $^{169}$Er, $^{177}$Lu, $^{186}$Re, $^{188}$Re, $^{189}$Re, $^{194}$Ir, $^{198}$Au, $^{199}$Au, $^{211}$Pb, $^{212}$Pb, and $^{213}$Bi. Maximum decay energies of useful beta-particle-emitting nuclides are preferably 20–5,000 keV, more preferably 100–4,000 keV, and most preferably 500–2,500 keV. Also preferred are radionuclides that substantially decay with Auger-emitting particles. For example, $^{58}$Co, $^{67}$Ga, $^{80m}$Br, $^{99m}$Tc, $^{103m}$Rh, $^{109}$Pt, $^{111}$In, $^{119}$Sb, $^{125}$I, $^{161}$Ho, $^{189m}$Os and $^{192}$Ir. Decay energies of useful Auger-particle-emitting nuclides are preferably <1,000 keV, more preferably <100 keV, and most preferably <70 keV. Also preferred are radionuclides that substantially decay with generation of alpha-particles. Such radionuclides include, but are not limited to: $^{152}$Dy, $^{211}$At, $^{212}$Bi, $^{22}$Ra, $^{219}$Rn, $^{215}$Po, $^{211}$Bi, $^{225}$Ac, $^{221}$Fr, $^{217}$At, $^{213}$Bi, and $^{255}$Fm. Decay energies of useful alpha-particle-emitting radionuclides are preferably 2,000–10,000 keV, more preferably 3,000–8,000 keV, and most preferably 4,000–7,000 keV.

Radionuclides useful as diagnostic agents utilizing gamma-ray detection include, but are not limited to: $^{51}$Cr, $^{57}$Co, $^{58}$Co, $^{59}$Fe, $^{67}$Cu, $^{67}$Ga, $^{75}$Se, $^{97}$Ru, $^{99m}$Tc, $^{111}$In, $^{114m}$In, $^{123}$I, 125I, $^{131}$I, $^{169}$Yb, $^{197}$Hg, and $^{201}$Tl, Decay energies of useful gamma-ray emitting radionuclides are preferably 20–2000 keV, more preferably 60–600 keV, and most preferably 100–300 keV.

Radionuclides useful for positron emission tomography include, but are not limited to: $^{18}$F, $^{51}$Mn, $^{52m}$Mn, $^{52}$Fe, $^{55}$Co, $^{62}$Cu, $^{64}$Cu, $^{68}$Ga, $^{72}$As, $^{75}$Br, $^{76}$Br, $^{82m}$Rb, $^{83}$Sr, $^{86}$Y, $^{89}$Zr, 94mTc, $^{110}$In, $^{120}$I, and $^{124}$I. Total decay energies of useful positron-emitting radionuclides are preferably <2,000 keV, more preferably under 1,000 keV, and most preferably <700 keV.

Bispecific antibodies of the present invention are useful in pretargeting methods and provide a preferred way to deliver two therapeutic agents or two diagnostic agents to a subject. U.S. Ser. Nos. 09/362,186 and 09/337,756 discloses a method of pretargeting using a bispecific antibody, in which the bispecific antibody is labeled with $^{251}$I and delivered to a subject, followed by a divalent peptide labeled with $^{99m}$Tc and are incorporated herein by reference in their entirety. Pretargeting methods are also described in U.S. Pat. No. 6,962,702 (Hansen et al.), U.S. Ser. Nos. 10/150,654 (Goldenberg et al.), and Ser. No. 10/768,707 (McBride et al.), which are all also incorporated herein by reference in their entirety. The delivery results in excellent tumor/normal tissue ratios for $^{125}$I and $^{99m}$Tc, thus showing the utility of two diagnostic radioisotopes. Any combination of known therapeutic agents or diagnostic agents can be used to label the antibodies and antibody fusion proteins. The binding specificity of the antibody component of the MAb conjugate, the efficacy of the therapeutic agent or diagnostic agent and the effector activity of the Fc portion of the antibody can be determined by standard testing of the conjugates.

The invention is directed to a method for pretargeting a cell in a patients suffering from a B-cell lymphoma or leukemia or an autoimmune disease comprising:

(i) administering an antibody fusion protein or fragment thereof that is multispecific having at least one arm that specifically binds the cell and at least one other arm that specifically binds a targetable conjugate; (ii) optionally, administering to the patient a clearing composition, and allowing the composition to clear non-antigen bound antibody fusion protein or fragment thereof from circulation; and (iii) administering to the patient a targetable conjugate comprising a carrier portion which comprises or bears at least one epitope recognizable by at least one other arm of the antibody fusion protein or fragment thereof, and is conjugated at least one first therapeutic or diagnostic agent. The antibody fusion protein of the present invention should be multispecific antibody. In a preferred embodiment the antibody is a bispecific antibody, and can be a diabody. The first therapeutic agent is selected from the group consisting of a radioactive label, an immunomodulator, a hormone, a photoactive therapeutic agent, a cytotoxic agent, an oligonucleotide and a combination thereof and wherein the first diagnostic agent is at least one of a radioactive label, a photoactive diagnostic agent or a non-radioactive label. The antibody fusion protein or fragment thereof also may be conjugated to a second therapeutic, such as at least one radioactive label, an immunomodulator, a hormone, a photoactive therapeutic agent, a cytotoxic agent, an oligonucleotide and a combination thereof or may be conjugated the second diagnostic agent, such as at least one of a radioactive label, a photoactive diagnostic agent or a non-radioactive label. In one embodiment, the first and second therapeutic agent or diagnostic agent are the same.

A therapeutic or diagnostic agent can be attached at the hinge region of a reduced antibody component via disulfide bond formation. As an alternative, such peptides can be attached to the antibody component using a heterobifunctional cross-linker, such as N-succinyl 3-(2-pyridyldithio) propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187–230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60–84 (Cambridge University Press 1995). Alternatively, the therapeutic or diagnostic agent can be conjugated via a carbohydrate moiety in the Fc region of the antibody. The carbohydrate group can be used to increase the loading of the same peptide that is bound to a thiol group, or the carbohydrate moiety can be used to bind a different peptide.

Methods for conjugating peptides to antibody components via an antibody carbohydrate moiety are well-known to those of skill in the art. See, for example, Shih et al., Int. J. Cancer 41: 832 (1988); Shih et al., Int. J. Cancer 46: 1101 (1990); and Shih et al., U.S. Pat. No. 5,057,313, all of which are incorporated in their entirety by reference. The general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

The Fc region is absent if the antibody used as the antibody component of the immunoconjugate is an antibody fragment. However, it is possible to introduce a carbohydrate moiety into the light chain variable region of a full length antibody or antibody fragment. See, for example, Leung et al., J. Immunol. 154: 5919 (1995); Hansen et al., U.S. Pat. No. 5,443,953 (1995), Leung et al, U.S. Pat. No. 6,254,868, all of which are incorporated in their entirety by reference. The engineered carbohydrate moiety is used to attach the therapeutic or diagnostic agent.

10. Pharmaceutically Acceptable Excipients

The humanized, chimeric and human anti-CD20 mAbs to be delivered to a subject can consist of the MAb alone, immunoconjugate, fusion protein, or can comprise one or more pharmaceutically suitable excipients, one or more additional ingredients, or some combination of these.

The immunoconjugate or naked antibody of the present invention can be formulated according to known methods to prepare pharmaceutically useful compositions, whereby the immunoconjugate or naked antibody are combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate or naked antibody of the present invention can be formulated for intravenous administration via, for example, bolus injection or continuous infusion. Preferably, the antibody of the present invention is infused over a period of less than about 4 hours, and more preferably, over a period of less than about 3 hours. For example, the first 25–50 mg could be infused within 30 minutes, preferably even 15 min, and the remainder infused over the next 2–3 hrs. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic or diagnostic conjugate or naked antibody. Control release preparations can be prepared through the use of polymers to complex or adsorb the immunoconjugate or naked antibody. For example, biocompatible polymers include matrices of poly (ethylene-co-vinyl acetate) and matrices of a polyanhydride copolymer of a stearic acid dimer and sebacic acid. Sherwood et al., Bio/Technology 10: 1446 (1992). The rate of release of an immunoconjugate or antibody from such a matrix depends upon the molecular weight of the immunoconjugate or antibody, the amount of immunoconjugate, antibody within the matrix, and the size of dispersed particles. Saltzman et al, Biophys. J. 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate, antibody fusion proteins, or naked antibody may also be administered to a mammal subcutaneously or even by other parenteral routes. Moreover, the administration may be by continuous infusion or by single or multiple boluses. Preferably, the antibody of the present invention us infused over a period of less than about 4 hours, and more preferably, over a period of less than about 3 hours. This is preferably performed by infusing slowly at first. For example, a dose of 25 to 50 mg is infused within 15–30 minutes and the remainder of the dose is infused over a period of up to 2–3 hrs. In general, the dosage of an administered immunoconjugate, fusion protein or naked antibody for humans will vary depending upon such factors as the patient's age, weight, height, sex, general medical condition and previous medical history. Typically, it is desirable to provide the recipient with a dosage of immunoconjugate, antibody fusion protein or naked antibody that is in the range of from about 1 mg/kg to 20 mg/kg as a single intravenous infusion, although a lower or higher dosage also may be administered as circumstances dictate. Therefore, 1–20 mg/kg for a 70 kg patient, for example, is a dose of 70–1,400 mg, or 41–824 mg/m$^2$ for a 1.7-m patient. This dosage may be repeated as needed, for example, once per week for 4–10 weeks, preferably once per week for 8 weeks, and more preferably, once per week for 4 weeks. It may also be given less frequently, such as every other week for several months. More specifically, an antibody of the present invention, such as naked anti-CD20, may be administered as one dosage every 2 or 3 weeks, repeated for a total of at least 3 dosages. Also preferred, the antibodies of the present invention may be administered once per week for 4–8 weeks. In other words, if the dosage is lowered to approximately 200–300 mg/m$^2$ (which is 340 mg per dosage for a 1.7-m patient, or 4.9 mg/kg for a 70 kg patient), it may be administered once weekly for 4 to 8 weeks. Alternatively, the dosage schedule may be decreased, namely every 2 or 3 weeks for 2–3 months; for example, if the dosage is 300–500 mg/m$^2$ (i.e., 510–850 mg for a 1.7-m patient, or 7.3–12 mg/kg for a 70 kg patient). The dosing schedule can optionally be repeated at other intervals and dosage may be given through various parenteral routes, with appropriate adjustment of the dose and schedule.

For purposes of therapy, the immunoconjugate, fusion protein, or naked antibody is administered to a mammal in a therapeutically effective amount. A suitable subject for the present invention are usually a human, although a non-human animal subject is also contemplated. An antibody preparation is said to be administered in a "therapeutically effective amount" if the amount administered is physiologically significant. An agent is physiologically significant if its presence results in a detectable change in the physiology of a recipient mammal. In particular, an antibody preparation of the present invention is physiologically significant if its presence invokes an antitumor response or mitigates the signs and symptoms of an autoimmune disease state. A physiologically significant effect could also be the evocation of a humoral and/or cellular immune response in the recipient mammal.

11. Methods of Treatment

The present invention contemplates the use of naked anti-CD20 antibodies of the present invention as the primary composition for treatment of B cell disorders and other diseases. In particular, the compositions described herein are particularly useful for treatment of various autoimmune as well as indolent forms of B-cell lymphomas, aggressive forms of B-cell lymphomas, chronic lymphatic leukemias, acute lymphatic leukemias, and Waldenstrom's macroglobulinemia. For example, the humanized anti-CD20 antibody components and immunoconjugates can be used to treat both indolent and aggressive forms of non-Hodgkin's lymphoma.

The compositions for treatment contain at least one humanized, chimeric or human monoclonal anti-CD20 antibody alone or in combination with other antibodies, such as other humanized, chimeric, or human antibodies, therapeutic agents or immunomodulators. In particular, combination therapy with a fully human antibody is also contemplated and is produced by the methods as set forth above.

Naked or conjugated antibodies to the same or different epitope or antigen may be also be combined with one or more of the antibodies of the present invention. For example, a humanized, chimeric or human naked anti-CD20 antibody may be combined with another naked humanized, naked chimeric or naked human anti-CD20, a humanized, chimeric or human naked anti-CD20 antibody may be combined with an anti-CD20 immunoconjugate, a naked anti-CD20 antibody may be combined with an anti-CD22 radioconjugate or an anti-CD22 naked antibody may be combined with a humanized, chimeric or human anti-CD20 antibody conjugated to an isotope, or one or more chemotherapeutic agents, cytokines, toxins or a combination thereof. A fusion protein of a humanized, chimeric or human CD20 antibody and a toxin or immunomodulator, or a fusion protein of at least two different B-cell antibodies (e.g., a CD20 and a CD22 MAb) may also be used in this invention. Many different antibody combinations, targeting at least two different antigens associated with B-cell disorders, as listed already above, may be constructed, either as naked antibodies or as partly naked and partly conjugated with a therapeutic agent or immunomodulator, or merely in combination with another therapeutic agents, such as a cytotoxic drug or with radiation.

As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12, IL-21 and IL-18), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor," erythropoietin and thrombopoietin. Examples of suitable immunomodulator moieties include IL-2, IL-6, IL-10, IL-12, IL-18, IL-21, interferon-γ, TNF-α, and the like. Alternatively, subjects can receive naked anti-CD20 antibodies and a separately administered cytokine, which can be administered before, concurrently or after administration of the naked anti-CD20 antibodies. As discussed supra, the anti-CD20 antibody may also be conjugated to the immunomodulator. The immunomodulator may also be conjugated to a hybrid antibody consisting of one or more antibodies binding to different antigens.

Multimodal therapies of the present invention further include immunotherapy with naked anti-CD20 antibodies supplemented with administration of anti-CD22, anti-CD19, anti-CD21, anti-CD74, anti-CD80, anti-CD23, anti-CD46 or HLA-DR (including the invariant chain) antibodies in the form of naked antibodies, fusion proteins, or as immunoconjugates. The naked anti-CD20 antibodies or fragments thereof may also be supplemented with naked antibodies against a MUC1 antigen that is expressed on certain B-cells. These antibodies include polyclonal, monoclonal, chimeric, human or humanized antibodies that recognize at least one epitope on these antigenic determinants. Anti-CD 19 and anti-CD22 antibodies are known to those of skill in the art. See, for example, Ghetie et al., *Cancer Res.* 48:2610 (1988); Hekman et al, *Cancer Immunol. Immunother.* 32:364 (1991); Longo, *Curr. Opin. Oncol.* 8:353 (1996) and U.S. Pat. Nos. 5,798,554 and 6,187,287, incorporated in their entirety by reference.

In another form of multimodal therapy, subjects receive naked anti-CD20 antibodies, and/or immunoconjugates, in conjunction with standard cancer chemotherapy. For example, "CVB" (1.5 g/m$^2$ cyclophosphamide, 200–400 mg/m$^2$ etoposide, and 150–200 mg/m$^2$ carmustine) is a regimen used to treat non-Hodgkin's lymphoma. Patti et al., *Eur. J. Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028–2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate and brostatin-1. In a preferred multimodal therapy, both chemotherapeutic drugs and cytokines are co-administered with an antibody, immunoconjugate or fusion protein according to the present invention. The cytokines, chemotherapeutic drugs and antibody or immunoconjugate can be administered in any order, or together.

In a preferred embodiment, NHL or the autoimmune disease is treated with 4 weekly infusions of the humanized anti-CD20 antibody at a does of 200–400 mg/m$^2$ weekly for 4 consecutive weeks (iv over 2–6 hours), repeated as needed over the next months/yrs. Preferably, the humanized anti-CD-20 antibody is administered at a dose of 200–300 mg/m$^2$ once every other week or every third week, for 4 to 8 injections. Also preferred, NHL is treated with 4 weekly infusions as above, or injections less frequently as above, but combined with epratuzumAb (anti-CD22 humanized antibody) on the same days, at a dose of 360 mg/m$^2$, given as iv infusion over 1 hour, either before, during or after the anti-CD20 monoclonal antibody infusion. Or, the antibodies used in combination therapy may also be infused in alternative sequences, such that they are alternated on different weeks, resulting in each being given every other week for a total injection sequence for each of 4 to 8 or more doses. These dosage schedules can then be repeated at different intervals, such as every 3–6 months, depending on the patient's clinical status and response to each therapy regimen. Still preferred, NHL is treated with 4 weekly infusions, or less frequent infusions, of the anti-CD20 antibody as above, combined with one or more injections of CD22 MAb radiolabeled with a therapeutic isotope such as yttrium-90 (at a total dose of Y-90 between 5 and 35 mCi/meter-square as one or more injections over a period of weeks or months). U.S. Ser. No. 09/590,284 (Goldenberg et al.) discloses immunotherapy of autoimmune disorders using an anti-CD22 antibody, which is incorporated herein by reference in its entirety.

In addition, a therapeutic composition of the present invention can contain a mixture or hybrid molecules of monoclonal naked anti-CD20 antibodies directed to different, non-blocking CD20 epitopes. Accordingly, the present invention contemplates therapeutic compositions comprising a mixture of monoclonal anti-CD20 antibodies that bind at least two CD20 epitopes. Additionally, the therapeutic composition described herein may contain a mixture of anti-CD20 antibodies with varying CDR sequences.

Although naked anti-CD20 antibodies are the primary therapeutic compositions for treatment of B cell lymphoma and autoimmune diseases, the efficacy of such antibody therapy can be enhanced by supplementing the naked antibodies, with supplemental agents, such as immunomodulators, like interferons. including IFNα, IFNβ and IFNγ, interleukins including IL-I, IL-2, IL-6, IL-12, IL-15, IL-18, IL-21, and cytokines including G-CSF and GM-CSF. Accordingly, the CD20 antibodies can be combined not only with antibodies and cytokines, either as mixtures (given separately or in some predetermined dosing regimen) or as conjugates or fusion proteins to the anti-CD20 antibody, but also can be given as a combination with drugs. For example, the anti-CD20 antibody may be combined with CHOP as a 4-drug chemotherapy regimen. Additionally, a naked anti-CD20 antibody may be combined with naked anti-CD22 antibodies and CHOP or fludarabine as a drug combination for NHL therapy. Immunotherapy of B-cell malignancies using an anti-CD22 antibody is described in U.S. Pat. No. 6,183,744 (Goldenberg et al.) and U.S. Pat. No. 6,306,393 (Goldenberg et al.), which are incorporated herein by reference in their entirety. The supplemental therapeutic compositions can be administered before, concurrently or after administration of the anti-CD20 antibodies.

As discussed supra, the antibodies of the present invention can be used for treating B cell lymphoma and leukemia, and other B cell diseases or disorders. For example, anti-CD20 antibodies can be used to treat B-cell related autoimmune diseases, including Class III autoimmune diseases such as immune-mediated thrombocytopenias, such as acute idiopathic thrombocytopenic purpura and chronic idiopathic thrombocytopenic purpura, dermatomyositis, Sjögren's syndrome, multiple sclerosis, Sydenham's chorea, myasthenia gravis, systemic lupus erythematosus, lupus nephritis, rheumatic fever, rheumatoid arthritis, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis ubiterans, , primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

Anti-CD20 antibodies may also induce apoptosis in cells expressing the CD20 antigen. Evidence of this induction is supported in the literature. For example, it was demonstrated that apoptosis could be induced using lymphoid cells that have Fc-receptors reactive with the IgG1-Fc of CD20 MAbs that crosslinked. See Shan et al., *Cancer Immunol. Immunother*. 48(12):673–683 (2000). Further, it was reported that aggregates of a chimeric CD20 MAb, i.e., homopolymers, induced apoptosis. See Ghetie et al., *Blood* 97(5): 1392–1398 (2000) and Ghetie et al., *Proc. Natl. Acad. Sci USA* 94(14): 7509–7514 (1997).

Antibodies specific to the CD20 surface antigen of B cells can be injected into a mammalian subject, which then bind to the CD20 cell surface antigen of both normal and malignant B cells. A mammalian subject includes humans and domestic animals, including pets, such as dogs and cats. The anti-CD20 mAbs of the present invention, i.e., humanized, chimeric, human, caninized and felinized, and even murine anti-CD20 mAbs, can be used to treat the non-human mammalian subjects when there is a species crossreactivity for the CD20 antigen. See Examples 10 and 11, below. The murine mAbs, which are immunogenic in humans, are usually less immunogenic in non-human mammalian subjects. The anti-CD20 antibody bound to the CD20 surface antigen leads to the destruction and depletion of neoplastic B cells. Because both normal and malignant B cells express the CD20 antigen, the anti-CD20 antibody will result in B cell death. However, only normal B cells will repopulate and the malignant B cells will be eradicated or significantly reduced. Additionally, chemical agents or radioactive labels having the potential to destroy the tumor can be conjugated to the anti-CD20 antibody such that the agent is specifically targeted to the neoplastic B cells.

12. Expression Vectors

The DNA sequence encoding a humanized, chimeric or human anti-CD20 MAb can be recombinantly engineered into a variety of known host vectors that provide for replication of the nucleic acid. These vectors can be designed, using known methods, to contain the elements necessary for directing transcription, translation, or both, of the nucleic acid in a cell to which it is delivered. Known methodology can be used to generate expression constructs the have a protein-coding sequence operably linked with appropriate transcriptional/translational control signals. These methods include in vitro recombinant DNA techniques and synthetic techniques. For example, see Sambrook et al., 1989, MOLECULAR CLONING: A LABORATORY MANUAL, Cold Spring Harbor Laboratory (New York); Ausubel et al., 1997, CURRENT PROTOCOLS IN MOLECULAR BIOLOGY, John Wiley & Sons (New York). Also provided for in this invention is the delivery of a polynucleotide not associated with a vector.

Vectors suitable for use in the instant invention can be viral or non-viral. Particular examples of viral vectors include adenovirus, AAV, herpes simplex virus, lentivirus, and retrovirus vectors. An example of a non-viral vector is a plasmid. In a preferred embodiment, the vector is a plasmid.

An expression vector, as described herein, is a polynucleotide comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

Preferably, the expression vector of the instant invention comprises the DNA sequence encoding a humanized, chimeric or human anti-CD20 MAb, which includes both the heavy and the light chain variable and constant regions. However, two expression vectors may be used, with one comprising the heavy chain variable and constant regions and the other comprising the light chain variable and constant regions. Still preferred, the expression vector further comprises a promoter. Because any strong promoter can be used, a DNA sequence encoding a secretion signal peptide, a genomic sequence encoding a human IgG1 heavy chain constant region, an Ig enhancer element and at least one DNA sequence encoding a selection marker.

Also contemplated herein is a method for expressing a humanized anti-CD20 MAb, comprising (i) linearizing at least one expression vector comprising a DNA sequence encoding a humanized, chimeric, or human anti-CD20 MAb, (ii) transfecting mammalian cells with at least one of said linearized vector, (iii) selecting transfected cells which express a marker gene, and (iv) identifying the cells secreting the humanized anti-CD20 MAb from the transfected cells.

13. Methods of Making Anti-CD20 Antibodies

In general, the Vκ (variable light chain) and $V_H$ (variable heavy chain) sequences for an anti-CD20 MAb can be obtained by a variety of molecular cloning procedures, such as RT-PCR, 5'-RACE, and cDNA library screening. Specifically, the V genes of an anti-CD20 MAb can be cloned by PCR amplification from a cell that expresses a murine or chimeric anti-CD20 MAb, sequenced. To confirm their authenticity, the cloned $V_L$ and $V_H$ genes can be expressed in cell culture as a chimeric Ab as described by Orlandi et al, (*Proc. Natl. Acad. Sci., USA*, 86: 3833 (1989)) which is incorporated by reference. Based on the V gene sequences, a humanized anti-CD20 MAb can then be designed and constructed as described by Leung et al. (*Mol. Immunol.*, 32: 1413 (1995)), which is incorporated by reference. cDNA can be prepared from any known hybridoma line or transfected cell line producing a murine or chimeric anti-CD20 MAb by general molecular cloning techniques (Sambrook et al., Molecular Cloning, A laboratory manual, $2^{nd}$ Ed (1989)). The Vκ sequence for the MAb may be amplified using the primers VK1BACK and VK1FOR (Orlandi et al, 1989) or the extended primer set described by Leung et al. (*BioTechniques*, 15: 286 (1993)), which is incorporated by reference, while $V_H$ sequences can be amplified using the primer pair VH1BACK/VH1FOR (Orlandi et al., 1989 above), or the primers annealing to the constant region of murine IgG described by Leung et al. (Hybridoma, 13:469 (1994)), which is incorporated by reference. The PCR reaction mixtures containing 10 µl of the first strand cDNA product, 10 µl of 10×PCR buffer [500 mM KCl, 100 mM Tris-HCl (pH 8.3), 15 mM MgCl$_2$, and 0.01% (w/v) gelatin] (Perkin Elmer Cetus, Norwalk, Conn.), 250 µM of each dNTP, 200 nM of the primers, and 5 units of Taq DNA polymerase (Perkin Elmer Cetus) can be subjected to 30 cycles of PCR. Each PCR cycle preferably consists of denaturation at 94° C. for 1 min, annealing at 50° C. for 1.5 min, and polymerization at 72° C. for 1.5 min. Amplified Vκ and VH fragments can be purified on 2% agarose (BioRad, Richmond, Calif.). Similarly, the humanized V genes can be constructed by a combination of long oligonucleotide template syntheses and PCR amplification as described by Leung et al. (*Mol. Immunol*, 32: 1413 (1995)). See Example 3 for a method for the synthesis of an oligo A and an oligo B on an automated RNA/DNA synthesizer (Applied Biosystems, foster City, Calif.) for use in constructing humanized V genes.

PCR products for Vκ can be subcloned into a staging vector, such as a pBR327-based staging vector, VKpBR, that contains an Ig promoter, a signal peptide sequence and convenient restriction sites to facilitate in-frame ligation of the Vκ PCR products. PCR products for V$_H$ can be subcloned into a similar staging vector, such as the pBluescript-based VHpBS. Individual clones containing the respective PCR products may be sequenced by, for example, the method of Sanger et al (*Proc. Natl. Acad. Sci.*, USA, 74: 5463 (1977)), which is incorporated by reference.

The DNA sequences described herein are to be taken as including all alleles, mutants and variants thereof, whether occurring naturally or induced.

The expression cassettes containing the Vκ and VH, together with the promoter and signal peptide sequences can be excised from VKpBR and VHpBS, respectively, by double restriction digestion as HindIII-BamHI fragments. The Vκ and VH expression cassettes can then be ligated into appropriate expression vectors, such as pKh and pG1 g, respectively (Leung et al., Hybridoma, 13:469 (1994)). The expression vectors can be co-transfected into an appropriate cell, e.g., myeloma Sp2/0-Ag14 (ATCC, VA), colonies selected for hygromycin resistance, and supernatant fluids monitored for production of a chimeric or humanized anti-CD20 MAb by, for example, an ELISA assay, as described below. Alternately, the Vκ and VH expression cassettes can be assembled in the modified staging vectors, VKpBR2 and VHpBS2, excised as XbaI/BamHI and XhoI/BamHI fragments, respectively, and subcloned into a single expression vector, such as pdHL2, as described by Gilles et al. (*J. Immunol. Methods* 125:191 (1989) and also shown in Losman et al., *Cancer*, 80:2660 (1997)) for the expression in Sp2/0-Ag14 cells. Another vector that is useful in the present invention is the GS vector, as described in Barnes et al., *Cytotechnology* 32:109–123 (2000), which is preferably expressed in the NS0 cell line and CHO cells. Other appropriate mammalian expression systems are described in Werner et al, Arzneim.-Forsch./Drug Res. 48(II), Nr. 8, 870–880 (1998).

Co-transfection and assay for antibody secreting clones by ELISA, can be carried out as follows. About 10 µg of VKpKh (light chain expression vector) and 20 µg of VHpG1g (heavy chain expression vector) can be used for the transfection of 5×10$^6$ SP2/0 myeloma cells by electroporation (BioRad, Richmond, Calif.) according to Co et al., *J. Immunol.*, 148: 1149 (1992) which is incorporated by reference. Following transfection, cells may be grown in 96-well microtiter plates in complete HSFM medium (Life Technologies, Inc., Grand Island, N.Y.) at 37° C., 5% CO$_2$. The selection process can be initiated after two days by the addition of hygromycin selection medium (Calbiochem, San Diego, Calif.) at a final concentration of 500 units/ml of hygromycin. Colonies typically emerge 2–3 weeks post-electroporation. The cultures can then be expanded for further analysis.

Transfectoma clones that are positive for the secretion of chimeric or humanized heavy chain can be identified by ELISA assay. Briefly, supernatant samples (~100 µl) from transfectoma cultures are added in triplicate to ELISA microtiter plates precoated with goat anti-human (GAH)-IgG, F(ab')$_2$ fragment-specific antibody (Jackson ImmunoResearch, West Grove, Pa.). Plates are incubated for 1 h at room temperature. Unbound proteins are removed by washing three times with wash buffer (PBS containing 0.05% polysorbate 20). Horseradish peroxidase (HRP) conjugated GAH-IgG, Fc fragment-specific antibodies (Jackson ImmunoResearch) are added to the wells, (100 µl of antibody stock diluted×10$^4$, supplemented with the unconjugated antibody to a final concentration of 1.0 µg/ml). Following an incubation of 1 h, the plates are washed, typically three times. A reaction solution, [100 µl, containing 167 µg of orthophenylene-diamine (OPD) (Sigma, St. Louis, Mo.), 0.025% hydrogen peroxide in PBS], is added to the wells. Color is allowed to develop in the dark for 30 minutes. The reaction is stopped by the addition of 50 µl of 4 N HCl solution into each well before measuring absorbance at 490 nm in an automated ELISA reader (Bio-Tek instruments, Winooski, Vt.). Bound chimeric antibodies are than determined relative to an irrelevant chimeric antibody standard (obtainable from Scotgen, Ltd., Edinburg, Scotland).

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2µ membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 µl of 3 M Tris (pH 8.6), and protein concentrations determined from the absorbance at 280/260 nm. Peak fractions are pooled, dialyzed against PBS, and the antibody concentrated, for example, with the Centricon 30 (Amicon, Beverly, Mass.). The antibody concentration is determined by ELISA, as before, and its concentration adjusted to about 1 mg/ml using PBS. Sodium azide, 0.01% (w/v), is conveniently added to the sample as preservative.

The following are the nucleotide sequences of the primers used to prepare the anti-CD20 antibodies:

```
hA20VKA                             (SEQ ID NO: 14)
5'-CATCTCTGAG CGCATCTGTT GGAGATAGGG TCACTATGAC
TTGTAGGGCC AGCTCAAGTG TAAGTTACAT CCACTGGTTC
CAGCAGAAAC CAGGGAAAGC ACCTAAACCC TGGATTTATG-3' hA20VKB                             (SEQ ID NO: 15)
5'-GGTGTCCCTG TCCGATTCTC TGGCAGCGGA TCTGGGACAG
ATTACACTTT CACCATCAGC TCTCTTCAAC CAGAAGACAT
TGCAACATAT TATTGTCAGC AGTGGACTAG TAACCCACCC
ACGTTCGGTG-3' hA20VKA-Backward                    (SEQ ID NO: 16)
5'-CAGCTGACCC AGTCTCCATC ATCTCTGAGC GCATCTGTTG-3' hA20VKA-Forward                     (SEQ ID NO: 17)
5'-AGGTTCGAAG TGGCATAAAT CCAGGGTTTA GGTGCT-3'
```

-continued

```
hA20VKB Backward                    (SEQ ID NO: 18)
5'-CACTTCGAAC CTGGCTTCTG GTGTCCCTGT CCGATTCTC-3' hA20VKB Forward                     (SEQ ID NO: 19)
5'-ACGTTAGATC TCCAGCTTGG TCCCTCCACC GAACGTGGGT
GGGTTA-3' hA20VHA                             (SEQ ID NO: 20)
5'-CTGAAGTCAA GAAACCTGGG TCATCGGTGA AGGTCTCCTG
CAAGGCTTCT GGCTACACCT TTACTAGTTA CAATATGCAC
TGGGTCAAGC AGGCACCTGG ACAGGGTCTG GAATGGATTG G-3' hA20VHB                             (SEQ ID NO: 21)
5'-ATCAGAAGTT CAAGGGTAAA GCCACACTGA CTGCCGACGA
ATCCACCAAT ACAGCCTACA TGGAGCTGAG CAGCCTGAGG
TCTGAGGACA CGGCATTTTA TTACTGTGCA AGATCGACTT
ACTACGGCGG TGACTGGTAC TTCGATGTCT G-3' hA20VHA Backward                    (SEQ ID NO: 22)
5'-CAGCTGCAGC AATCAGGGGC TGAAGTCAAG AAACCTGGG-3' hA20VHA Forward                     (SEQ ID NO: 23)
5'-TTCCGGGATA AATAGCTCCA ATCCATTCCA GACCCTG-3' hA20VHB Backward                    (SEQ ID NO: 24)
5'-ATCCCGGAAA TGGTGATACT TCCTACAATC AGAAGTTCAA
GGGTAAAGCC A-3' hA20VHB Forward                     (SEQ ID NO: 25)
5'-GGAGACGGTG ACCGTGGTGC CTTGGCCCCA GACATCGAAG
TACCAG-3' hA20VH2A                            (SEQ ID NO: 26)
5'-CTGAAGTCAA GAAACCTGGG TCATCAGTGA AGGTCTCCTG
CAAGGCTTCT GGCTACACCT TTAGTAGTTA CAATATGCAC
TGGGTCAGAC AGGCACCTGG ACAGGGTCTG GAATGGATGG G-3' hA20VH2B                            (SEQ ID NO: 27)
5'-ATCAGAAGTT CAAGGGTAGA GCCACAATAA CTGCCGACGA
ATCCACCAAT ACAGCCTACA TGGAGCTGAG CAGCCTGAGG
TCTGAGGACA CGGCATTTTA TTTTTGTGCA AGATCGACTT
ACTACGGCGG TGACTGGTAC TTCGATGTCT G-3' hA20VH2A Forward                    (SEQ ID NO: 28)
5'-TTCCGGGATA AATAGCTCCC ATCCATTCCA GACCCTG-3' hA20VH2B Backward                   (SEQ ID NO: 29)
5'-ATCCCGGAAA TGGTGATACT TCCTACAATC AGAAGTTCAA
GGGTAGAGCC A-3'
```

The invention is further described by reference to the following examples, which are provided for illustration only. The invention is not limited to the examples but rather includes all variations that are evident from the teachings provided herein.

EXAMPLES

Example 1

Construction of a Humanized Anti-CD20 Antibody

The $V_H$ and Vκ genes of A20, an anti-CD20 antibody, was obtained by RT-PCR using the primer pairs VH1BACK/VH1FOR and VK1BACK/VK1FOR, respectively Orlandi et al., (*Proc. Natl. Acad. Sci.*, USA, 86: 3833 (1989)). Multiple independent clones were sequenced to eliminate possible errors resulting from the PCR reaction. The cloned murine $V_H$ and Vκ sequences as the final PCR product were designated A20Vk (FIG. 1A) and A20VH (FIG. 1B), respectively. A chimeric A20 (cA20) antibody was constructed and expressed in Sp2/0 cell. The Vk and VH of sequences of cA20 are shown in FIG. 2. The cA20 antibody bound to Raji cell and competed with radiolabeled A20 purified from the hybridoma cell culture supernatant (FIG. 3). This result confirmed the authenticity of the cloned V genes.

A single light chain and two heavy chain variable region sequences encoding the humanized anti-hCD20 (hA20) antibody were designed and constructed. Human REI framework sequences were used for Vκ (FIG. 1A), and a combination of EU and NEWM framework sequences were used for $V_H$ (FIG. 1B). There are a number of amino acid changes in each chain outside of the CDR regions when compared to the starting human antibody frameworks. The heavy chain of hA20, hA20$V_H$1, contains nine changes, while hA20$V_H$2 contains three changes from the human EU frameworks (FIG. 4A). hA20$V_H$2 is preferred because it contains more amino acids from the human antibody framework region than hA20$V_H$1. The light chain of hA20, hA20Vκ, contains seven amino acid changes from the REI framework (FIG. 4B).

Example 2

Method of hA20 Antibody Construction

Each variable chain was constructed in two parts, a 5'- and 3'-half, designated as "A" and "B" respectively. Each half was produced by PCR amplification of a single strand synthetic oligonucleotide template with two short flanking primers, using Taq polymerase. The amplified fragments were first cloned into the pCR4 TA cloning vector from Invitrogen (Carlsbad, Calif.) and subjected to DNA sequencing. The templates and primer pairs are listed as follows:

| Template | Primers |
| --- | --- |
| VKA | VkA-Backward/VkA-Forward |
| VKB | VkB-Backward/VkB-Forward |
| VH1A | VHA-Backward/VH1A-Forward |
| VH1B | VH1B-Backward/VHB-Forward |
| VH2A | VHA-Backward/VH2A-Forward |
| VH2B | VH2B-Backward/VHB-Forward |

Light Chain

For constructing the full-length DNA of the humanized Vκ sequence, oligo hA20VKA (120 mer) and hA20VKB (130 mer) were synthesized on an automated RNA/DNA synthesizer (Applied Biosystems). hA20VKA and B represent the nt 26–145 and 166–195, respectively, of the hA20 Vκ. (See FIG. 5A) Oligo hA20VKA and B were cleaved from the support and deprotected by treatment with concentrated ammonium hydroxide. After samples were vacuum-tried and resuspended in 100 μl of water, incomplete oligomers (less than 100-mer) were removed by centrifugation through a ChormaSpin-100 column (Clontech, Palo Alto, Calif.). All flanking primers were prepared similarly, except ChromaSpin-30 columns were used to remove synthesis by-products. 1 μl of ChromaSpin column purified hA20VKA was PCR amplified in a reaction volume of 100 μl containing 10 μl of 10×PCR buffer [500 mM KCl, 100 mM Tris-HCl (pH 8.3), 15 mM MgCl$_2$, and 0.01% (w/v) gelatin] (Perkin Elmer Cetus, Norwalk, Conn.), 250 μM of each dNTP, 200 nM of VkA-Backward and VkA-Forward, and 5 units of Taq DNA polymerase (Perkin Elmer Cetus). This reaction mixture was subjected to 30 cycles of PCR reaction consisting of denaturation at 94° C. for 1 min, annealing at 50° C. for 1.5 min, and polymerization at 72° C. for 1.5 min. hA20VKB was PCR-amplified by the primer pair VkB-Backward and VkB-Forward under similar condition. The amplified VKA and VKA fragments were purified on 2% agarose (BioRad, Richmond, Calif.). Unique restriction sites were designed at the ends of each fragment to facilitate joining through DNA ligation. The amplified VKA fragment contained a PvuII restriction site, CAGCTG, at its 5'-end and a BstBI restriction site, TTCGAA, at the 3'-end. The amplified VKB fragment contained a BstBI restriction site at its 5'-end and a BglII restriction site, AGATCT, at the 3'-end. Assembly of the full-length Vκ chain was accomplished by restriction enzyme digestion of each fragment with the appropriate 5'- and 3'-enzymes and ligation into the VKpBR2 vector previously digested with PvuII and BclI (BclI digested end is compatible with that of BglII). The resulting ligated product contains the A fragment ligated to the PvuII site, the B fragment ligated to the BclI site, and the A and B fragments joined together at the BstBI site (FIG. 5A). VKpBR2 is a modified staging vector of VKpBR (Leung et al., Hybridoma, 13:469 (1994)), into which a XbaI restriction site was introduced at 14 bases upstream of the translation initiation codon. Upon confirmation of a correct open reading frame by DNA sequencing, the intact chain was removed from VKpBR2 as a XbaI to BamHI fragment and ligated into the pdHL2 expression vector. The vector containing only Vκ sequence was designated as hA20VκpdHL2. pdHL2 contains the expression cassettes for both human IgG1 C1, C2, C3, and hinge regions (FIG. 7A) and the human kappa chain Ck (FIG. 7B) under the control of IgH enhancer and $MT_I$ promoter, as well as a mouse dhfr gene, controlled by a weak SV40 promotor, as a marker for selection of transfectants and co-amplification of the trans-genes (Gillies et al., *J. Immunol. Methods* 125:191 (1989); Losman et al., *Cancer* 80:2660 (1997)). By replacing the Vκ and VH segments of pdHL2, different chimeric or humanized Abs can be expressed.

Heavy Chain

For the construction of hA20VH1, oligo VH1A (121 mer) and VH1B (151 mer), representing the nt 23–143 and 179–329, respectively, (See FIG. 5B) were synthesized as described above. Similarly, for hA20VH2, oligo VH2A and VH2B were prepared. These oligos were PCR-amplified by their respective primer pairs as listed in Example 2. The same construction method as done for V was carried out for both types of $V_H$, with the following modifications: the 5'-end restriction site of the A fragments was PstI (CTGCAG) and the 3'-end restriction site of B fragments was BstEII (GGTCACC). These fragments were joined together upon ligation into the VHpBS2 vector at a common NciI site (CCCGG), resulting in full-length $V_H$ sequences (FIGS. 5B and 5C) and confirmed by DNA sequencing. VHpBS2 is a modified staging vector of VHpBS (Leung et al., Hybridoma, 13:469 (1994)), into which a XhoI restriction site was introduced at 16 bases upstream of the translation initiation codon. The assembled $V_H$ genes were subcloned as XhoI-BamHI restriction fragments into the expression vector containing the V sequence, hA20V pdHL2. Since the heavy chain region of pdHL2 lacks a BamHI restriction site, this ligation required use of the HNB linker to provide a bridge between the BamHI site of the variable chain and the HindIII site present in the pdHL2 vector. The resulting expression vectors were designated as hA20-1pdHL2 and hA20-2pdHL2.

```
                     (SEQ ID NO: 30)
HNB linker    5'-AGCTTGCGGCCGC-3'
```

```
                     -continued
                     (SEQ ID NO: 31)
              3'-ACGCCGGCGCTAG-5'
```

Example 3

Transfection and Expression of hA20 Antibodies

Approximately 30 μg of the expression vectors for hA20 were linearized by digestion with SalI and transfected into Sp2/0-Ag14 cells by electroporation (450V and 25 μF). The transfected cells were plated into 96-well plates for 2 days and then selected for drug-resistance by adding MTX into the medium at a final concentration of 0.025 μM. MTX-resistant colonies emerged in the wells 2–3 weeks. Supernatants from colonies surviving selection were screened for human Ab secretion by ELISA assay. Briefly, 100 μl supernatants were added into the wells of a microtiter plate precoated with GAH-IgG, F(ab')$_2$ fragment-specific Ab and incubated for 1 h at room temperature. Unbound proteins were removed by washing three times with wash buffer (PBS containing 0.05% polysorbate 20). HRP-conjugated GAH-IgG, Fc fragment-specific Ab was added to the wells. Following an incubation of 1 h, the plate was washed. The bound HRP-conjugated Ab was revealed by reading A490 nm after the addition of a substrate solution containing 4 mM OPD and 0.04% $H_2O_2$. Positive cell clones were expanded and hA20-1 and hA20-2 were purified from cell culture supernatant by affinity chromatography on a Protein A column.

Example 4

Binding Activity of Anti-CD20 Antibodies

Figure 6A:
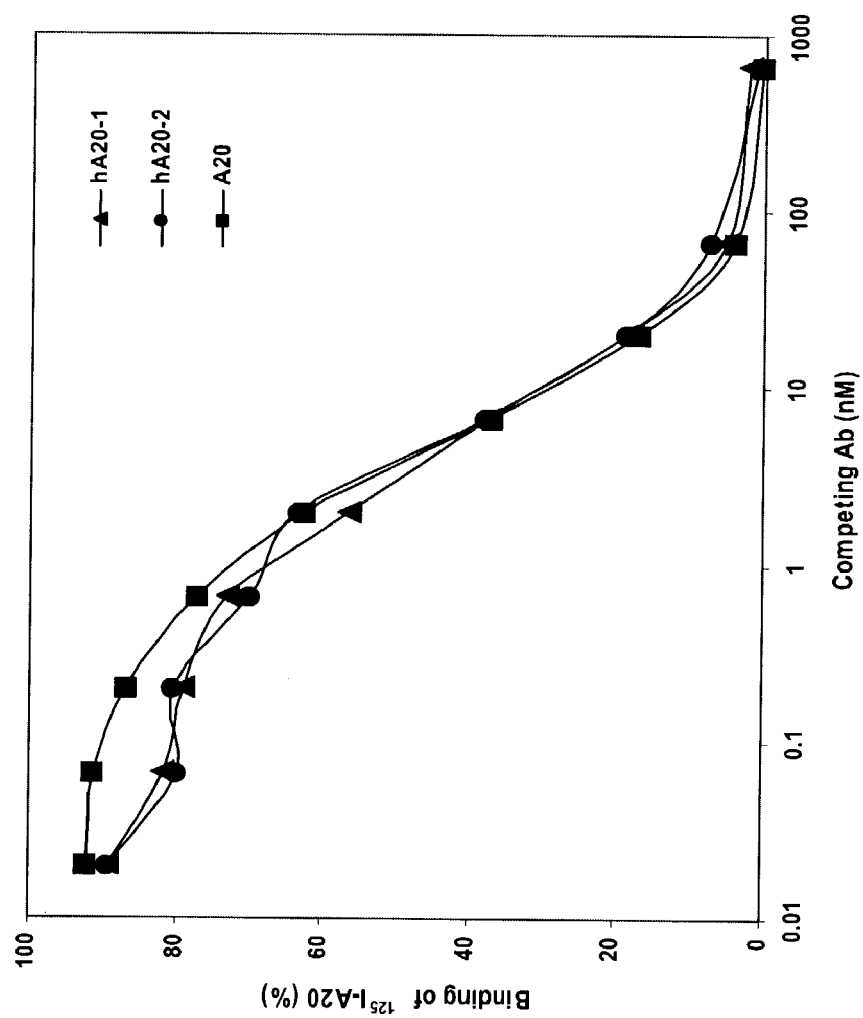
FIG. 6A shows hA20-1 (closed triangles) and hA20-2 (closed circles) and the murine anti-CD20 antibody, A20 (closed squares) competed equally well for the binding of $^{125}$I-A20 to Raji cells.
Figure 6B:
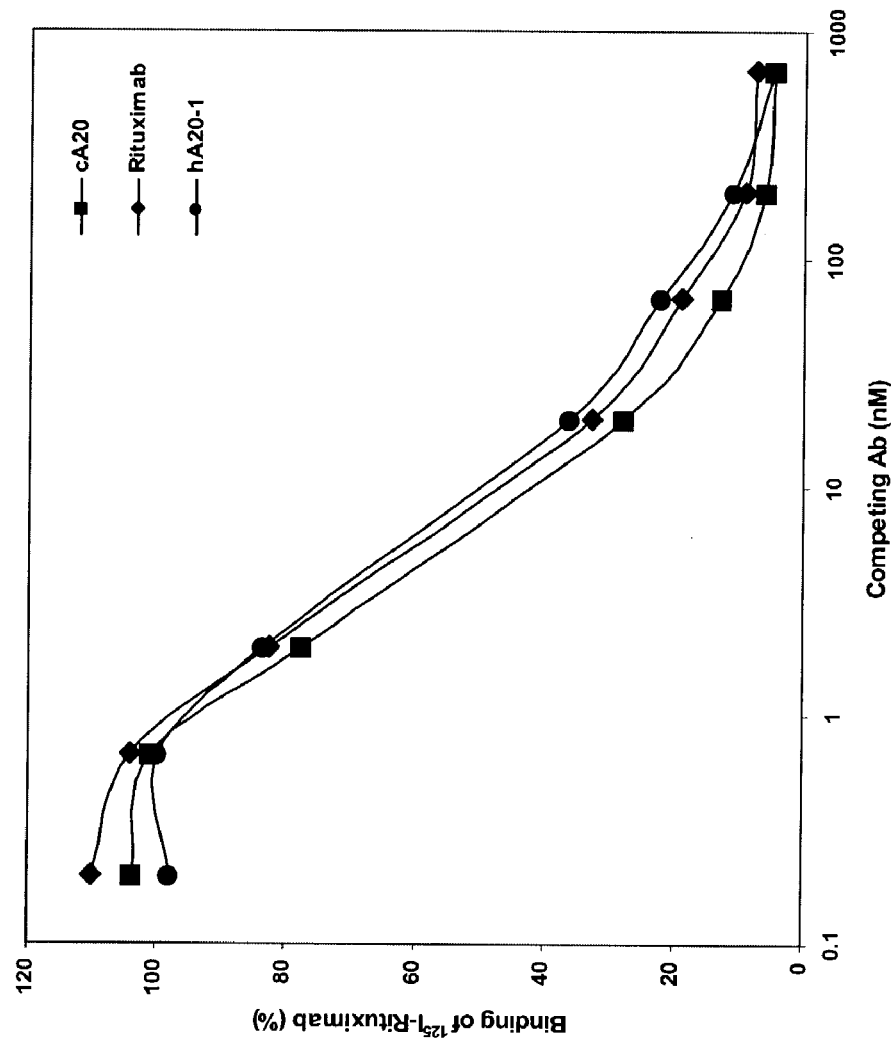
FIG. 6B shows hA20-1 (closed circles), cA20 (closed squares) and c2B8 (closed diamonds) competed equally well for the binding of $^{125}$I-c2B8 to Raji cells.

A competition cell-binding assay was carried out to assess the immunoreactivity of hA20 relative to the parent cA20 and the anti-CD20 Ab c2B8. A constant amount of $^{125}$I-labeled murine A20 or c2B8 (100,000 cpm, ~10 μCi/μg) was incubated with Raji cell in the presence of varying concentrations (0.2–700 nM) of hA20-1, -2, murine A20, cA20, or c2B8 at 4° C. for 1–2 h. Unbound Abs were removed by washing the cells in PBS. The radioactivity associated with cells was determined after washing. As shown in FIG. 6, both humanized A20 mAbs, hA20-1 and hA20-2, exhibited comparable binding activities as A20, the murine anti-CD20 MAb, cA20, and c2B8, a chimeric anti-CD20 MAb, when competing with binding of $^{125}$I-A20 or $^{125}$I-c2B8 to Raji cells.

By direct binding of radiolabeled Mabs to Raji cells and Scatchard plot anlaysis, the dissociation constants were measured to be 2.9 and 4.2 nm for cA20 and hA20, respectively, in comparison to 3.9 nM for C2B8. In vitro crosslinking experiments, using a goat anti-human IgG, Fc fragment specific antibody to complex with the antibodies showed similar killing of Raji NHL cells between cA20 and hA20, as well as C2B8.

Example 5

Treatment of a Patient with Relapsed Intermediate-Grade Non-Hodgkin's Lymphoma

A patient with intermediate grade non-Hodgkin's lymphoma has failed prior aggressive chemotherapy, consisting of CHOP×6, which led to a complete remission for four months, another course of CHOP×6, resulting in progression, D-MOPP×2, resulting in stable disease for three months, and CVB with peripheral stem cell transplantation, which led to a partial remission for five months. The patient presents with recurrent lymphoma in a neck lymph node, measurable by computerized tomography and palpation.

The patient is infused within 3 hrs with 450 mg of humanized CD20 monoclonal antibody A20 on days 0, 14, 28, and 42 with no serious adverse effects noted either during or immediately after the infusions. Eight weeks later, palpation of the neck node enlargement shows a measurable decrease of about 50%. Follow-up measurements made at twenty weeks post therapy show no evidence of the disease in the neck, and nowhere else, as confirmed by computed tomography studies of the body. Since new disease is not detected elsewhere, the patient is considered to be in complete remission. Follow-up studies every 10–12 weeks confirms a complete remission for at least ten months post therapy.

Example 6

Treatment of a Patient with Chronic Idiopathic Thrombocytopenia Purpura

A 45-year-old female with chronic idiopathic thrombocytopenia purpura has been treated with prednisone, gamma globulins, and high dose dexamethasone, but the disease progresses. She undergoes splenectomy, which fails to stabilize the disease. Her platelet count falls to less than 30,000/microliter, and hemorrhagic events increase in frequency. The patient is then treated with the humanized CD20 A20 MAb, 500 mg intravenously on the first week, followed by a dose of 250 mg given once every other week for a total of 4 injections. Ten weeks after the last dose of A20 a marked increase in platelet number is observed, to 150,000/microliter, and the hemorrhagic events disappear. Five months after the last antibody infusion the disease is in remission.

Example 7

Treatment of a Patient with Progressive Rheumatoid Arthritis

A 70 year old female, with severe progressive rheumatoid arthritis of the finger joints, wrists, and elbows, has failed therapy with methotrexate, and obtains only minor relief when placed on Enbrel therapy. The patient is then treated with A20 humanized CD20 MAb, 300 mg intravenously each week, for a period of four weeks. After 3 months, a 40% improvement in measures of disease activity is observed, which is maintained for 5 months. The patient is again treated with A20, at the same dose and frequency. The patient continues to improve, and 6 months after the second A20 MAb therapy, a 60% improvement is observed. No human anti-A20 antibodies are observed at any time during, or after the A20 therapy. Although normal B-cells are depleted from the blood, no infectious complications, or other drug-related severe toxicity is observed.

Example 8

Treatment of a Patient with Myasthenia Gravis

A 65 year old male has failed all conventional therapy for myasthenia gravis, and is admitted to a neurological intensive therapy unit. The patient was stabilized by plasma exchange, and given intravenous immunoglobulin to reduce the titer of antiacetylcholine receptor antibody. The patient remained bedridden, and was then treated with A20 humanized CD20 MAb, 400 mg intravenously once every other week, for a period of ten weeks. One week after the last dose of A20, no blood B-cells were detectable, and a significant drop in the titer of the anti-acetylcholine antibody was observed. Four months after the last A20 MAb dose the patient was mobile, and was released from the hospital.

Example 9

Treatment of a Dog with Aggressive Non-Hodgkin's B-cell Lymphoma in Lymph Nodes and Bone Marrow A 65-pound, 7-year old male Golden Retriever is diagnosed with diffuse large cell aggressive lymphoma. The dog is placed on combination chemotherapy with vincristine, cyclophosphamide, prednisolone, and doxorubicin, with good response. However, the dog subsequently is characterized as having progressive lymphadenopathy, and seven months after this is found to have extensive lymphoma infiltration of bone marrow, extensive lymphoadenopathy of neck, chest, abdomen, pelvis, and hepatosplenomegaly.

The dog is given therapy with 1F5 chimeric monoclonal antibody. The dog is infused intravenously with 120 mg of 1F5 antibody, and the treatment is repeated weekly for 4 weeks following this initial treatment. Four months after the final dose of 1F5, a computerized tomography scan of the patient shows no evidence of lymphoma, and all signs and symptoms of the disease were not evident.

Example 10

Treatment of a Dog with Relapsed Intermediate-Grade Non-Hodgkin's Lymphoma

A 78-pound, 9-year old, German Shepherd dog with intermediate grade non-Hodgkin's lymphoma receives chemotherapy, which initially leads to a complete remission for five months, followed by another course of chemotherapy which results in stable disease for six months. The dog then presents with recurrent lymphoma in the chest and in a neck lymph node, both measurable by computerized tomography and palpation, respectively.

The patient is infused with a $^{90}$Y-labeled immunoconjugate of L243 (HLA-DR) monoclonal antibody weekly for two weeks, at a radiation dose of 8 mCi in 50 mg of antibody protein, in combination with the A20 humanized CD20 antibody at a dose of 100 mg per each weekly infusion. Three weeks later, palpation of the neck node enlargement shows a measurable decrease, while a repeat computerized tomography scan of the chest shows a marked reduction in tumor. Follow-up measurements made at ten weeks post therapy show evidence of the disease in the neck or the chest being reduced by a about 60 percent. Since new disease is not detected elsewhere, the patient is considered to be in partial remission. Follow-up studies every 10–12 weeks confirms a partial remission for at least 7 months post therapy.

Example 11

Treatment of a Cat with Relapsed Lymphoma

A 10-pound, 12-year-old, domestic short hair presents with enlargement of a single submandibular lymph node. After excision, there is recurrence of the lesion at 6 months. The lesion is again excised, but then reappears 6 months later. The cat is then given weekly treatments for 4 weeks with an $^{131}$I-labeled immunoconjugate of anti-CD20 B1 monoclonal antibody, at a radiation dose of 15 mCi in 45 mg antibody protein. The treatment is repeated 3 months later. When examined 3 months after the last treatment, a marked decrease can be palpated. No recurrence of the disease is observed for over one year.

Example 12

Evalulation of Chimeric and Humanized Anti-CD20 Mabs in Human NHL Cells in Culture or Xenografted in SCID Mice The properties of a chimeric (cA20) and humanized (hA20) CD20 antibody was assessed in NHL cell lines. The results demonstrate that cA20 and hA20 behave similarly to Rituximab, staining more than 99% of Raji, Ramos, RL, Daudi and Su-DHL-6 cells and reacting with approximately 5% of lymphocytes (expected % B-cells). In all B-cell lines, specific growth inhibition was seen with the Mabs, but the level o f inhibition varied between the cell lines, with Su-DHL being the most sensitive. In the absence of cross-linking, murine anti-CD20, cA20, hA20 and rituximab all yielded between 77 and 90% inhibition. With cross-linking, inhibition of proliferation ranged from 94–98%. Rituximab, cA20, and hA20 were also similar in their ability to induce apoptosis in Raji cells in the presence of a cross-linking second monoclonal antibody.

Figure 11:
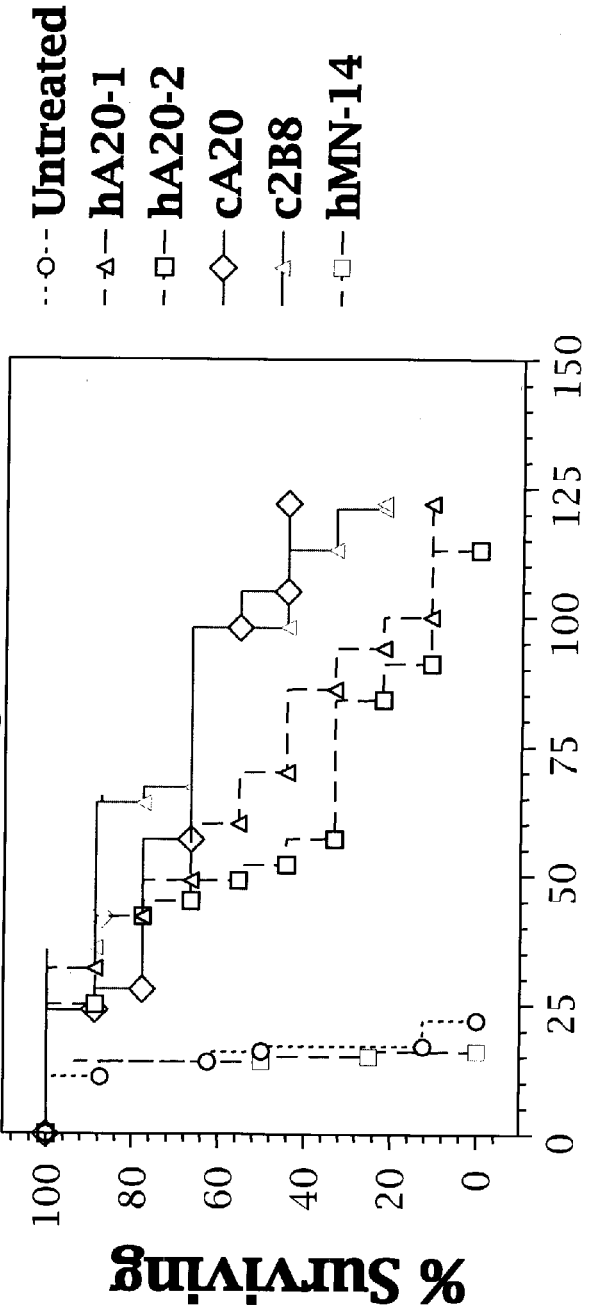
FIG. 11 is a graph of in vivo therapy studies with various anti-CD20 and other Abs. Raji cells administered i.v. to SCID mice, to create a Raji lymphoma model of disseminated disease.

Also, SCID mice were injected intravenously with $2.5 \times 10^6$ Raji cells on day 0. Injections of murine, chimeric and humanized anti-CD20 antibodies, and the cA20 F(ab')$_2$ fragment were initiated on day-1 with 100 μg/injection of intact antibody, or 67 μg/injection F(ab')$_2$ fragment, five times per week for two weeks, the twice weekly for three weeks. In one study, control mice died of disseminated disease with a median survival time of 15 days post tumor innoculation, but median survival was extended to 38 days for cA20, 22.5 days for hA20, and 21 days for murine anti-CD20 treated mice (all statistically significant by log-rank analysis ($p<0.005$)). In another study, control mice died of disseminated disease manifested with CNS paralysis with a median survival time of 16.5 days post tumor innoculation, but median survival was extended to 105 days for cA20, 70 days for hA20, and 98 days for rituximab treated mice (all statistically significant extensions by log-rank analysis ($p<0.0001$), FIG. 11).

Example 13

Competitive Cell Surface Binding Assay

Figures 8, 8A, 8B:
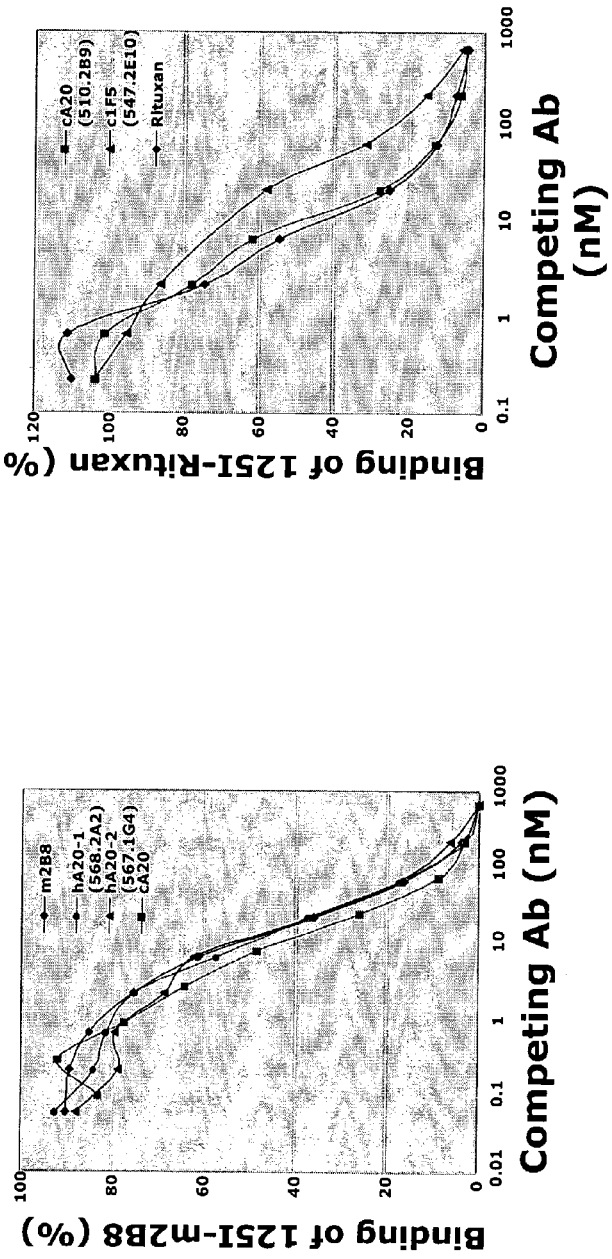
FIG. 8 is a competitive cell surface binding assay. Ag-binding specificity and affinity studies of humanized anti-CD20 Abs (cA20, hA20, and c1F5, purified by affinity chromatography on a Protein A column) were evaluated by a cell surface competitive binding assay with murine 2B8 and rituximab (IDEC Pharmaceuticals Corp., San Diego, Calif.).
FIG. 8(A) is a comparison of the binding activities of cA20 (square), hA20-1 (triangle) and hA20-1 (circle) with that of m2B8 (diamond)
FIG. 8(B) compares of the binding activities of cA20 (square), c1F5 (triangle) and rituximab (diamond).

Ag-binding specificity and affinity studies of humanized anti-CD20 Abs (cA20, hA20, and c1F5), purified by affinity chromatography on a Protein A column) were evaluated by a cell surface competitive binding assay with murine 2B8 and rituximab (IDEC Pharmaceuticals Corp., San Diego, Calif.) (FIG. 8). Briefly, a constant amount (100,000 cpm, ~10 iCi/ig) of $^{125}$I-labeled (A) m2B8 or (B) rituximab was incubated with Raji cells in the presence of varying concentrations (0.2–700 nM) of competing Abs (cA20, hA20, m2B8, c1F5, or rituximab) at 4° C. for 1–2 h. Unbound Abs were removed by washing the cells with PBS. Radioactivity associated with the cells was determined after washing. FIG. 8(A) is a comparison of the binding activities of cA20 (square), hA20-1 (triangle) and hA20-1 (circle) with that of m2B8 (diamond); FIG. 8(B) Compares the binding activities of cA20 (square), c1F5 (triangle) and rituximab (diamond).

Figure 9:
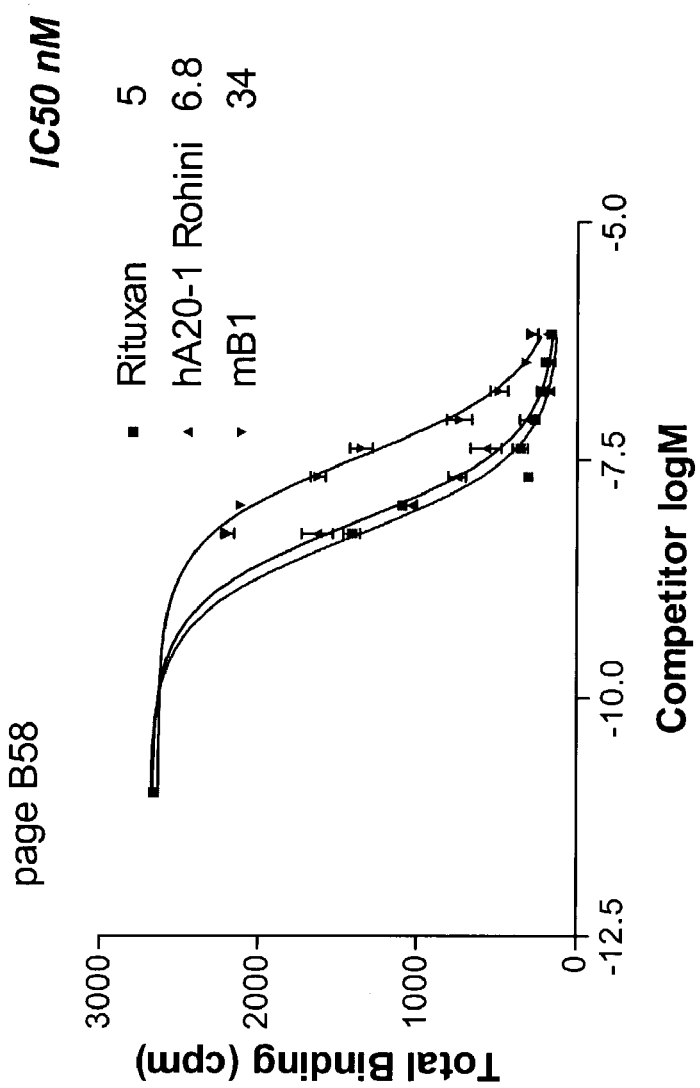
FIG. 9 is a study comparing the binding activities of hA20 with other anti-CD20 Abs, including rituximab and murine B1, by a cell surface competitive binding assay. A constant amount (100,000 cpm, ~10 iCi/ig) of $^{125}$I-labeled rituximab was incubated with Raji cells in the presence of varying concentrations (0.2–700 nM) of competing Abs, hA20 (triangle), mB1 (Downward triangle) or rituximab (square) at 4° C. for 1–2 h.

In another study, the binding activities of hA20 with other anti-CD20 Abs, rituximab and murine B1 were compared by a cell surface competitive binding assay (FIG. 9). Briefly, a constant amount (100,000 cpm, ~10 iCi/ig) of $^{125}$I-labeled rituximab was incubated with Raji cells in the presence of varying concentrations (0.2–700 nM) of competing Abs, hA20 (triangle), mB 1 (Downward triangle) or rituximab (square) at 4° C. for 1–2 h. Unbound Abs were removed by washing the cells with PBS. Radioactivity associated with the cells was determined after washing. The IC$_{50}$ values for these three Abs were calculated to be 6.8, 34, and 5, respectively.

Example 14

Cytotoxic Effect of Crosslinked hA20 and other CD20 Abs on Cultured Lymphoma Cells.

Figure 10:
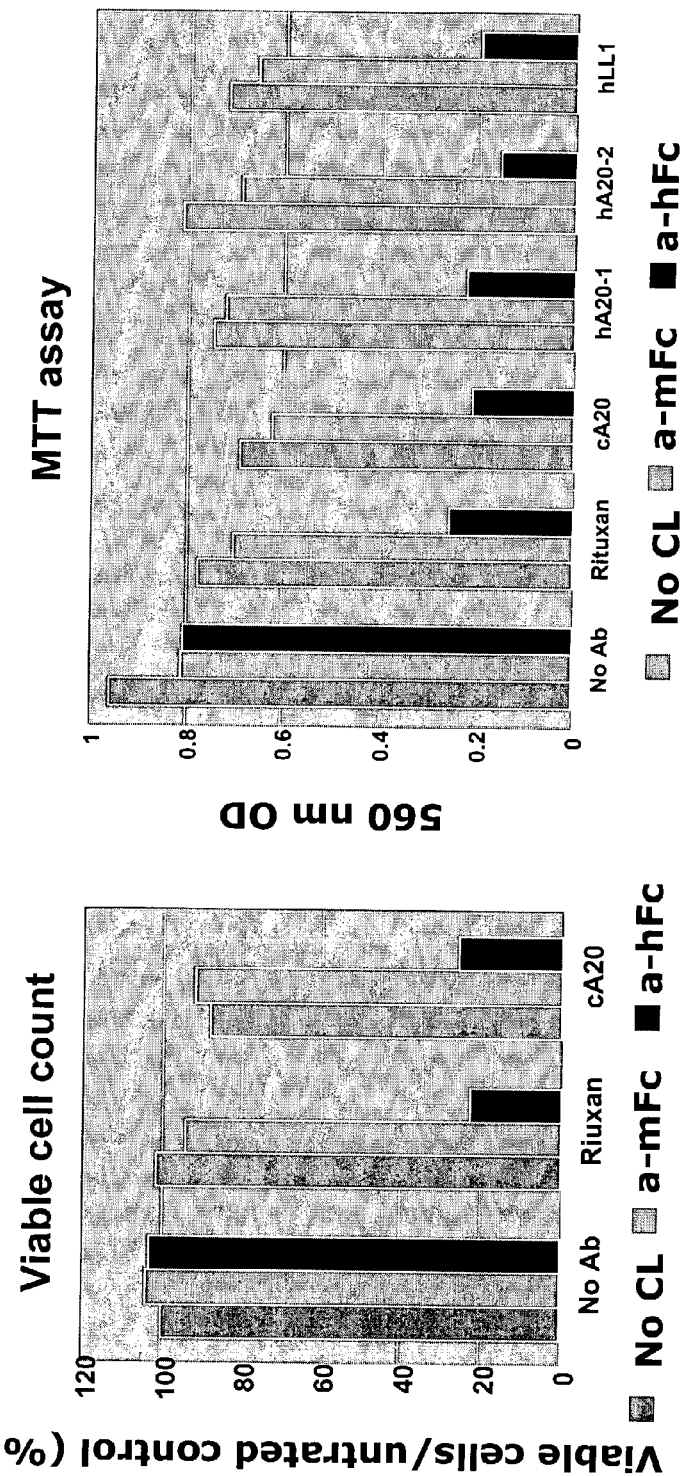
FIG. 10 depicts the cytotoxic effect of crosslinked hA20 and other CD20 Abs on cultured lymphoma cells. Total cell and viable cell cell populations were measured by (A) trypan blue staining and cell counting or (B) MTT assay.

Raji cells were treated with various CD20 Abs in the presence of a crosslinker (an anti-human IgG, Fc fragment specific antibody) to complex the CD20 antibodies (FIG. 10). A final concentration of 5 ig/ml of hA20, cA20, rituximab, or a positive control Ab, hLL1, was incubated with Raji cells, with 20 ig/ml of the crosslinker (red), without the crosslinker (orange), or with an anti-mouse IgG, Fc fragment specific antibody (blue) for 48 h. Total cell and viable cell populations were measured by (A) trypan blue staining and cell counting or (B) MTT assay (B). The data show a similar effect of hA20 and rituximab on Raji NHL cell survival, and that the cytotoxic effect is dependent on the specific crosslinking of the antibodies.

Example 15

In Vivo Therapy with hA20 and hLL2

Figure 12:
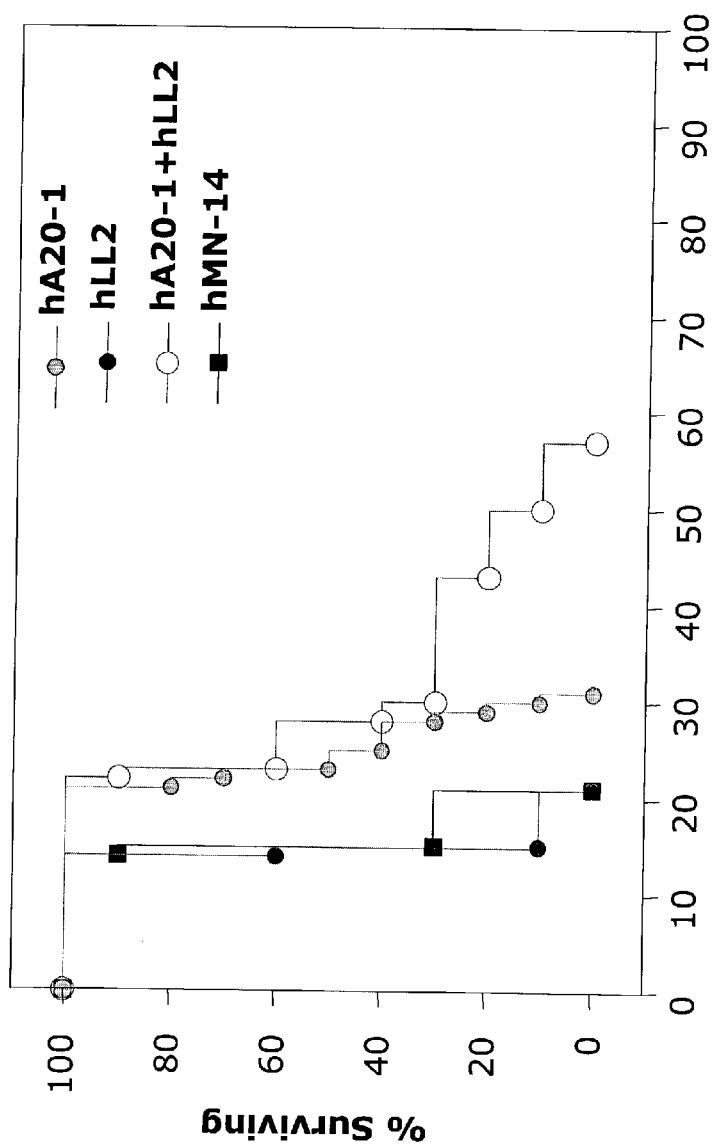
FIG. 12 is a graph depicting in vivo therapy with hA20 and hLL2. Raji cells administered i.v. to SCID mice, to create a Raji lymphoma model of disseminated disease.

Raji cells were administered i.v. to 60 SCID mice, at $2.5 \times 10^6$ cells/100 μl/mouse (FIG. 12). MAbs were administered i.p. on days 1 to 11, followed by MAb injections twice per week, for approximately 3 weeks. The body weight of the animals was measured weekly until the study was terminated. The animals were examined daily for paralysis of the hind legs. When paralysis occured, the animals were sacrificed and necropsied for visual inspection of disseminated tumor nodules (specifically in lungs, kidneys, and ovaries). Control mice treated with a control humanized IgG1 Ab, hMN-14 (an anti-CEA antibody), died of disseminated disease manifested with CNS paralysis. The median survival time was 13 days post tumor i.v. inoculation. Median survival in the group treated with hA20 was extended to about 25 days. This value represents median survival increase of approximately 2 fold for hA20. Although the group treated with hLL2 alone showed the same median survival time compared to the control mice, treatment with combination of hA20 and hLL2 increased the median survival time of the mice to approximately 30 days.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All of the publications and patent applications and patents cited in this specification are herein incorporated in their entirety by reference.

We claim:

1. A humanized antibody or antigen-binding antibody fragment thereof that binds CD20 comprising hA20Vk (residues 20–125 of SEQ ID NO: 46) and hA20VH1 (SEQ ID NO: 41).

2. A humanized antibody or antigen-binding antibody fragment thereof that binds CD20 comprising hA20Vk (residues 20–125 of SEQ ID NO: 46) and hA20VH2 (SEQ ID NO: 42).

3. The humanized antibody and antigen-binding fragments of claim 1, wherein said antigen-binding fragments are selected from the group consisting of F(ab')$_2$, Fab', Fab, Fv and sFv.

4. An isolated DNA sequence comprising a nucleic acid encoding hA20Vk (residues 20–125 of SEQ ID NO: 46) and hA20VH1 (SEQ ID NO: 41).

5. An expression vector comprising the DNA sequence of claim 4.

6. An isolated host cell comprising the DNA sequence of claim 4.

7. A method for expression of an antibody or antigen-binding fragment thereof comprising hA20Vk (residues 20–125 of SEQ ID NO: 46) and hA20VH1 (SEQ ID NO: 41), comprising:
   (a) transfecting a mammalian cell with a DNA sequence comprising a nucleic acid that encodes hA20Vk (residues 20–125 of SEQ ID NO: 46) and hA20VH1 (SEQ ID NO: 41); and
   (b) culturing said cell secreting said antibody or antigen-binding fragment thereof.

8. A method of treating a B-cell lymphoma or leukemia in a subject comprising administering to said subject a therapeutically effective amount of an antibody or an antigen-binding fragment thereof as claimed in claim 1.

9. A method of treating an autoimmune disease in a subject, wherein said autoimmune disease is mediated by B-cells, comprising administering to said subject a therapeutically effective amount of an antibody or antigen-binding fragment thereof as claimed in claim 1.

10. The humanized antibody and antigen-binding fragments of claim 2, wherein said antigen-binding fragments are selected from the group consisting of F(ab')$_2$, Fab', Fab, Fv and sFv.

11. An isolated DNA sequence comprising a nucleic acid encoding hA20Vk (residues 20–125 of SEQ ID NO: 46) and hA20VH2 (SEQ ID NO: 42).

12. An expression vector comprising the DNA sequence of claim 11.

13. An isolated host cell comprising the DNA sequence of claim 11.

14. A method for expression of an antibody or antigen-binding fragment thereof comprising hA20Vk (residues 20–125 of SEQ ID NO: 46) and hA20VH2 (SEQ ID NO: 42), comprising:
   (a) transfecting a mammalian cell with a DNA sequence comprising a nucleic acid that encodes hA20Vk (residues 20–125of SEQ ID NO: 46) and hA20VH2 (SEQ ID NO: 42); and
   (b) culturing said cell secreting said antibody or antigen-binding fragment thereof.

15. A method of treating a B-cell lymphoma or leukemia in a subject comprising administering to said subject a therapeutically effective amount of an antibody or antigen-binding fragment thereof as claimed in claim 2.

16. A method of treating an autoimmune disease in a subject, wherein said autoimmune disease is mediated by B-cells, comprising administering to said subject a therapeutically effective amount of an antibody or antigen-binding fragment thereof as claimed in claim 2.

* * * * *